US005672334A

United States Patent [19]
Ranney

[11] Patent Number: 5,672,334
[45] Date of Patent: Sep. 30, 1997

[54] INVIVO AGENTS COMPRISING CATIONIC METAL CHELATORS WITH ACIDIC SACCHARIDES AND GLYCOSAMINOGLYCANS

[75] Inventor: David F. Ranney, Dallas, Tex.

[73] Assignee: Access Pharmaceuticals, Inc., Dallas, Tex.

[21] Appl. No.: 160,085

[22] Filed: Nov. 29, 1993

Related U.S. Application Data

[63] Continuation-in-part of Ser. No. 880,660, May 8, 1992, abandoned, Ser. No. 863,595, Dec. 9, 1991, Pat. No. 5,214,661, and a continuation-in-part of Ser. No. 642,033, Jan. 16, 1991, Pat. No. 5,336,762.

[51] Int. Cl.$^6$ ............................. A61B 5/055
[52] U.S. Cl. ............ 424/9.34; 424/6; 424/450; 424/85.1; 424/85.2; 436/173; 436/806
[58] Field of Search ............... 424/9.34, 9.35, 424/1.73, 85.1, 85.2, 450; 436/173, 806; 514/54, 6, 56, 59, 836; 536/21, 15; 128/653.4, 654

[56] References Cited

U.S. PATENT DOCUMENTS

| | | | |
|---|---|---|---|
| 3,158,552 | 11/1964 | Gaeumann et al. | 195/80 |
| 3,957,435 | 5/1976 | Adams et al. | 23/230 B |
| 3,961,038 | 6/1976 | Benes | 424/1 |
| 4,024,073 | 5/1977 | Shimizu et al. | 252/316 |
| 4,115,534 | 9/1978 | Ithakissios | 424/1.1 |
| 4,182,330 | 1/1980 | Michaels | 128/260 |
| 4,385,046 | 5/1983 | Milbrath et al. | 424/9 |
| 4,397,867 | 8/1983 | Blake | 424/320 |
| 4,419,365 | 12/1983 | McLachlan | 424/320 |
| 4,427,808 | 1/1984 | Stol et al. | 524/24 |
| 4,432,802 | 2/1984 | Harata et al. | 106/163 R |
| 4,446,126 | 5/1984 | Jordan | 424/183 |
| 4,454,106 | 6/1984 | Gansow et al. | 424/1.1 |
| 4,568,536 | 2/1986 | Kronenthal et al. | 424/22 |
| 4,577,636 | 3/1986 | Spears | 128/654 |
| 4,613,616 | 9/1986 | Winston et al. | 514/507 |
| 4,619,913 | 10/1986 | Luck et al. | 514/2 |
| 4,624,846 | 11/1986 | Goldenberg | 424/1.1 |
| 4,647,447 | 3/1987 | Gries et al. | 424/9 |
| 4,671,958 | 6/1987 | Rodwell et al. | 424/85 |
| 4,678,667 | 7/1987 | Meares et al. | 424/85 |
| 4,683,142 | 7/1987 | Zimmerman et al. | 427/2 |
| 4,689,323 | 8/1987 | Mitra et al. | 514/56 |
| 4,703,108 | 10/1987 | Silver et al. | 530/356 |
| 4,710,493 | 12/1987 | Landsberger | 514/56 |
| 4,732,864 | 3/1988 | Tolman | 436/547 |
| 4,738,955 | 4/1988 | Landsberger | 514/56 |
| 4,745,180 | 5/1988 | Moreland et al. | 530/351 |
| 4,804,529 | 2/1989 | Bardy et al. | 424/9 |
| 4,863,964 | 9/1989 | Hedlund et al. | 514/575 |
| 4,880,008 | 11/1989 | Lauffer | 128/654 |
| 4,904,479 | 2/1990 | Illum | 424/490 |
| 4,925,678 | 5/1990 | Ranney | 424/493 |
| 4,957,939 | 9/1990 | Gries et al. | 514/492 |
| 4,963,344 | 10/1990 | Gries et al. | 424/9 |
| 4,986,980 | 1/1991 | Jacobsen | 424/9 |
| 5,021,236 | 6/1991 | Gries et al. | 424/9 |
| 5,021,404 | 6/1991 | Folkman et al. | 514/26 |
| 5,023,078 | 6/1991 | Halluin | 424/94.64 |
| 5,039,529 | 8/1991 | Bergendal et al. | 424/630 |
| 5,108,759 | 4/1992 | Ranney | 424/493 |
| 5,155,215 | 10/1992 | Ranney | 534/16 |
| 5,288,704 | 2/1994 | Ungheri et al. | 514/12 |
| 5,308,617 | 5/1994 | Halluin | 424/94.64 |
| 5,427,767 | 6/1995 | Kresse et al. | 424/9.32 |

FOREIGN PATENT DOCUMENTS

| | | |
|---|---|---|
| 1168150 | 5/1994 | Canada . |
| 0087786 | 9/1983 | European Pat. Off. . |
| WO83/03426 | 10/1983 | European Pat. Off. . |
| WO84/00294 | 2/1984 | European Pat. Off. . |
| 0137356 | 4/1985 | European Pat. Off. . |
| PCT/US88/01096 | 10/1988 | European Pat. Off. . |
| WO88/07365 | 10/1988 | European Pat. Off. . |
| 1516348 | 7/1978 | United Kingdom . |
| 2041517 | 9/1980 | United Kingdom . |
| 2185397 | 7/1987 | United Kingdom . |

OTHER PUBLICATIONS

Ranney, "Drug Targeting to the Lungs" *Biochemical Pharmacology*, vol. 35, No. 7, pp. 1063–1069, 1986, published in Europe.

(List continued on next page.)

*Primary Examiner*—Gary E. Hollinden
*Attorney, Agent, or Firm*—Arnold, White & Durkee

[57] ABSTRACT

This application concerns novel agents comprising cationic or chemically basic metal chelators in association with hydrophilic carriers of anionic or chemically acidic saccharides, sulfatoids and glycosaminoglycans. In certain embodiments, the agents comprise metals and metal ions. Covalent and non-covalent chemical and physical means are described for stabilizing the binding of the metal chelators to the carriers. Novel non-covalently bound compositions are described which give uniquely high payloads and ratio of metal chelator to carrier, ranging from a low of about 15% metal chelator by weight, to a characteristic range of 70% to 90% metal chelator by weight. Specific embodiments are described comprising deferoxamine, ferrioxamine, iron-basic porphine, iron-triethylenetetraamine, gadolinium DTPA-lysine, gadolinium DOTA-lysine and gadolinium with basic derivatives of porphyrins, porphines, expanded porphyrins, Texaphyrins and sapphyrins as the basic or cationic metal chelators, which are in turn, bound to acidic or anionic carriers, including one or more of acidic or anionic saccharides, and including sulfated sucrose, pentosan polysulfate, dermatan sulfate, oversulfated dermatan sulfate, chondroitin sulfate, oversulfated chondroitin sulfate, heparan sulfate, beef heparin, porcine heparin, non-anticoagulant heparins, and other native and modified acidic saccharides and glycosaminoglycans.

Also disclosed are methods of enhancing in vivo imgages arising from induced magnetic resonance signals, methods of enhancing in vivo images in conjunction with ultrasound or X-rays and methods of obtaining in vivo body images utilizing radioisotope containing agents. Methods of treating vasular disease are also disclosed.

33 Claims, 53 Drawing Sheets

OTHER PUBLICATIONS

Lambe, et al., "Morphological stabilization of the glycocalyces of 23 strains of five *Bacteroides* species using specific antisera" *Can. J. Microbiol.*, vol. 30, pp. 809–819, 1984, published in Canada.

Costerton, et al., "How Bacterial Stick" *Scientific American*, vol. 238:86, Jan. 1978, published in U.S.A.

Epenetos et al., "Monoclonal antibodies for imaging and therapy" *Br. J. Cancer*, 59:152–155, 1989, published in Europe.

Mayberry–Carson et al., "Bacterial Adherence and Glycocalyx Formation in Osteomyelitis Experimentally Induced with *Staphylococcus aureus*" *Infection and Immunity*, 43:825–833, Mar., 1984, published in U.S.A.

Jain, "Delivery of Novel Therapeutic Agents in Tumors: Physiological Barriers and Strategies" *Journal of the National Cancer Institute*, 81:570–576, 1989, published in U.S.A.

Henneberry et al., "Immunocytochemical Localization of VP16–213 In Normal and Malignant Tissues" *Cancer Letters*, 37, 1987, pp. 225–233, published in Ireland.

Henneberry et al., "Light Microscope Visualization of Tissue and Tumour Distributions of Anti–Cancer Drugs Using Immunocytochemistry". Abstract #1931, *Seventy–Ninth annual meeting of the American Association for Cancer Research May 25–28, 1988 Proceedings, Proceedings of AACR*, vol. 29, Mar. 1988, p. 486, published in U.S.A.

Dvorak et al., "Identification and Characterization of the Blood Vessels of Solid Tumors That Are Leaky to Circulating Macromolecules" *American Journal of Pathology*, vol. 133, No. 1, Oct. 1988, published in U.S.A.

Weinstein et al., "Selected Issues in the Pharmacology of Monoclonal Antibodies" *Site–Specific Drug Delivery*, 1986:pp. 81–91, published in U.S.A.

Mahadoo et al., "Vascular Sequestration of Heparin" *Thrombosis Research*, vol. 12, pp. 79–90, 1977, published in Europe.

Engel et al., "Intestinal Absorption of Heparin Facilitated by Sulfated of Sulfonated Surfactants" *Journal of Pharmaceutical Sciences*, vol. 58, No. 6, Jun. 1969, pp. 706–710, published in U.S.A.

Smirnov et al., "Carrier–directed targeting of liposomes and erythrocytes to denuded areas of vessel wall" *Proc. Natl. Acad. Sci. USA*, vol. 83, pp. 6603–6607, Sep. 1986, published in U.S.A.

Ghitescu et al., "Specific Binding Sites for Albumin Restricted to Plasmalemmal Vesicles of Continuous Capillary Endothelium: Receptor–mediated Transcytosis" *The Journal of Cell Biology*, vol. 102, Apr. 1986, pp. 1304–1311, published in U.S.A.

Laurie et al., "Localization of Binding Sites for Laminin, Heparan Sulfate Proteoglycan and Fibronectin on Basement Membrane (Type IV) Collagen" *J. Mol. Biol.*, 1986:189, pp. 205–216, published in Europe.

Williams et al., "Micropinocytic ingestion of glycosylated albumin by isolated microvessels: Possible role in pathogenesis of diabetic microangiopathy" *Proc. Natl. Acad. Sci, USA*, vol. 78, No. 4, pp. 2393–2397, Apr. 1981, published in U.S.A.

Glimelius et al., "Binding of Heparin on the Surface of Cultured Human Endothelial Cells" *Thrombosis Research*, 1978, vol. 12, No., 5, pp. 773–782, published in Europe.

Jaques, "Drug Prophylaxis in Atherosclerosis" *Artery*, 14(4):209–215, 1987, place of publication is uncertain, possibly Canada.

Parsons et al., "Antibacterial Activity of Bladder Surface Mucin Duplicated in the Rabbit Bladder by Exogenous Glycosaminoglycan (Sodium Pentosanpolysulfate)" *Infection and Immunity*. vol. 27, No. 3., Mar. 1980, pp. 876–881, published in U.S.A.

Ryan et al., "New Substrates for the Radioassay of Angiotensin Converting Enzyme of Endothelial Cells in Culture" *Tissue & Cell*, 1978 10(3):555–562, publised in Europe.

Fransson, "Self–Association of Bovine Lung Heparan Sulphates Indentification and Characterization of Contact Zones" *Eur. J. Biochem.* 120, 251–255, 1981, published in Europe.

Jaques et al., "Intrapulmonary Heparin A New Procedure for Anticoagulant Therapy" *The Lancet*, Nov. 27, 1976, pp. 1157–1161, published in Europe.

Wick et al., "In Vivo Localization and Pathological Effects of Passively Transferred Antibodies to Type IV Collagen and Laminin in Mice" *Clinical Immunology and Immunopathology*, 23:656–665, 1982, published in U.S.A.

Lopes et al., "Presence of Laminin Receptors in *Staphylococcus aureus*" *Science*, vol. 229, Jul. 1985, pp. 275–277, published in U.S.A.

Holthofer et al., "*Ulex europaeus* I Lectin as a Marker for Vascular Endothelium in Human Tissues" *Laboratory Investigation*, vol. 47, No. 1, pp. 60–65, 1982, published in U.S.A.

Loesberg et al., "The Effect of Calcium on the Secretion of Factor VIII–Related Antigen by Cultured Human Endothelial Cells," *Biochimica et Biophysica Acta*, 763:160–167, 1983, published in Europe.

Widder et al., "Magnetically Responsive Microspheres as a Carrier for Site–Specific Delivery of Adriamycin," *Proc. Am. Assn. Cancer Res.*, 19:17, 1978, published in USA.

Libby et al., "Inducible Interleukin–1 Gene Expression in Adult Human Vascular Endothelial Cells," *Proc. Fed. Am. Soc. for Exp. Biol.*, 45:1074, 1986, published in USA.

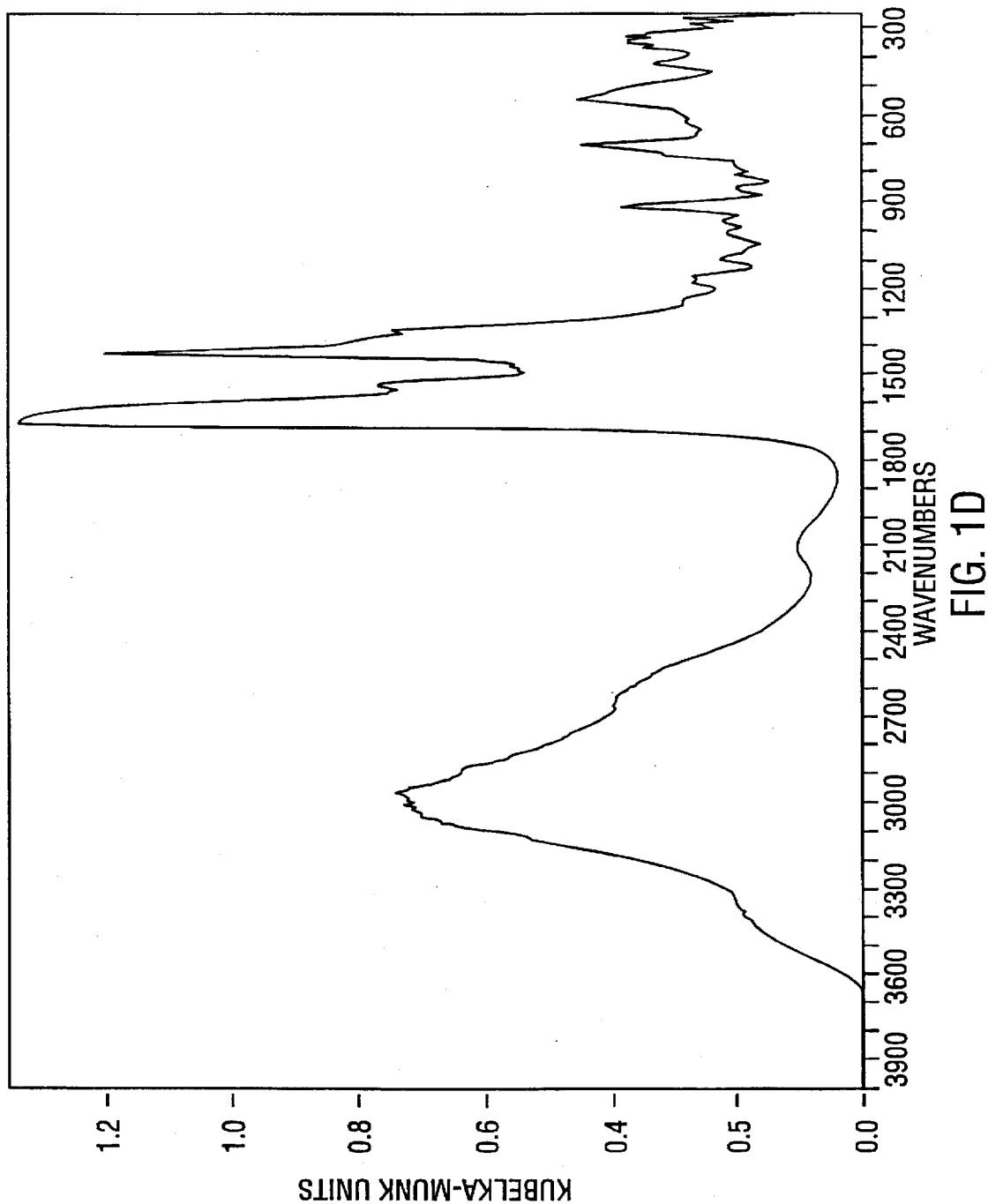

INVIVO AGENTS COMPRISING CATIONIC METAL CHELATORS WITH ACIDIC SACCHARIDES AND GLYCOSAMINOGLYCANS

This is a continuation-in-part of U.S. Ser. No. 07/880,660 filed May 8, 1992 abandoned, U.S. Ser. No. 07/863,595 filed Apr. 3, 1992, now U.S. Pat. No. 5,214,661 and U.S. Ser. No. 07/642,033 filed Jan. 1, 1991, now U.S. Pat. No. 5,336,762, all of which are incorporated by reference herein.

The present invention describes novel compositions, agents and methods of in vivo use which give improved selectivity, efficacy, uptake mechanism and kinetic-spatial profiles at sites of disease. It further describes compositions, agents and methods of use for improved selectivity, sensitivity, uptake mechanism and kinetic-spatial profiles of biomedical imaging, image contrast and spectral enhancement at sites of disease, including but not limited to magnetic resonance image (MRI) contrast enhancement. Novel compositions are prepared by (a) unique non-covalent chemical binding, further enhanced by (b) physical stabilization. Other compositions are prepared by covalent chemical binding. Binding is of cationic or chemically basic metal chelators to carriers comprising anionic or chemically acidic saccharides, sulfatoids and glycosaminoglycans, typically and advantageously of a hydrophilic or essentially completely hydrophilic nature. Binding of the active and carrier may also be by a combination of non-covalent, physical, and covalent means. Non-covalent binding can be carried out by means including but not limited to admixing cationic or basic metal chelators at appropriate ratios with anionic or acidic saccharide carriers, thereby forming solution-state and dry-state paired-ion salts, based principally on electrostatic binding of cationic (basic) group or groups of the metal chelator to anionic (acidic) group or groups of the acidic carrier. Such binding may be further stabilized by hydrogen bonds and physical factors, including but not limited to concentration, viscosity, and various means of drying, including lyophilization.

Carrier substances useful in this invention may include, but are not limited to natural and synthetic, native and modified, anionic or acidic saccharides, disaccharides, oligosaccharides, polysaccharides and glycosaminoglycans (GAGs). It will be apparent to those skilled in the art that a wide variety of additional biologically compatible, water-soluble and water dispersable, anionic carrier substances can also be used. Due to an absence of water-diffusion barriers, favorable initial biodistribution and multivalent site-binding properties, oligomeric and polymeric, hydrophilic and substantially completely hydrophilic carrier substances are included among the preferred carriers for agents to be used for paramagnetic, T1-Type, selective MRI contrast of tumors, cardiovascular infarcts and other T1-Type MRI contrast uses. However, it will be apparent to those skilled in the art that amphoteric and hydrophobic carriers may be favored for certain biomedical imaging applications and therapeutic applications. Metal chelators useful in this invention include those which contain cationic, basic and basic-amine groups and which chelate metals and metal ions, transition elements and ions, and lanthanide series elements and ions. It will be apparent to those skilled in the art that essentially any single atomic element or ion amenable to chelation by a cationic, basic and amine-containing chelator, may also be useful in this invention.

For purposes of this invention, a cationic or basic metal chelator is defined and further distinguished from a metal-ion complex as follows: a cationic or basic metal chelator comprises an organic, covalent, bridge-ligand molecule, capable of partly or entirely surrounding a single metal atom or ion, wherein the resulting formation constant of chelator for appropriate metal or ion is at least about $10^{14}$. A chelator is further defined as cationic or basic if it or its functional group or groups which confer the cationic or basic property, and which include but are not limited to an amine or amines, is (are) completely or essentially completely electrophilic, positively charged or protonated at a typical pH employed for formulation. A formulation pH is characteristically selected to closely bracket the range of physiologic pH present in mammalian vertebrates. This typically includes, but is not limited to a pH in the range of pH 5 to 8. Amines may include primary, secondary, tertiary or quaternary amines or combinations thereof on the metal chelator. Herein, and as specified, a hydrophilic carrier is defined as a substance which is water soluble, partitions into the water phase of aqueous-organic solvent mixtures, or forms a translucent aqueous solution, complex, aggregate, or particulate dispersion under the conditions employed for formulation. A carrier is further defined as being anionic or acidic if it is completely or nearly completely nucleophilic, or if its functional group or groups capable of interacting with cationic, basic or amine metal chelators, is (are) completely or nearly completely negatively charged, anionic or ionized at the pH employed for formulation. Such anionic and acidic groups include, but are not limited to sulfates, phosphates and carboxylates, or combinations thereof on the carrier.

Novel agent compositions include, but are not limited to the classes of cationic or basic, typically basic-amine metal chelator actives, or metal chelator actives including the chelated metal or metal ion, wherein these actives are further bound to anionic and acidic carriers comprising natural, synthetic or synthetic carriers, including but not limited to hydrophilic anionic or acidic, natural or synthetic, native, modified, derivatized and fragmented, anionic or acidic saccharides, oligosaccharides, polysaccharides, sulfatoids, and glycosaminoglycans (GAGs).

Anionic and acidic saccharide and glycosaminoglycan carriers may contain monomeric units comprising glucose, glucuronic acid, iduronic acid, glucosamine, galactose, galactosamine, xylose, mannose, fucose, sialic acid, pentose, and other naturally occurring, semi-synthetic or synthetic monosaccharides or chemical derivatives thereof, comprising amine, sulfate, carboxylate, sialyl, phosphate, hydroxyl or other side groups. Glycosaminoglycans (GAGs) comprise essentially the carbohydrate portions of cell-surface and tissue matrix proteoglycans. They are derived from naturally occurring proteoglycans by chemical separation and extraction; and in certain instances, by enzymatic means [Lindahl et al. (1978), incorporated herein by reference]. They include, but are not limited to those of the following types: heparin, heparan sulfate, dermatan sulfate, chondroitin-4-sulfate, chondroitin-6-sulfate, keratan sulfate, syndecan, and hyaluronate, and over-sulfated, hyper-sulfated, and other chemical derivatives thereof, as described further below.

Strongly acidic glycosaminoglycans include all of those classes listed just above, except for hyaluronate, which contains only the more weakly acidic carboxylate groups and not sulfate groups. Natural sources of glycosaminoglycans include, but are not limited to: pig and beef intestinal mucosa, lung, spleen, pancreas, and a variety of other solid and parenchymal organs and tissues.

Sulfatoids comprise a second class of sulfated saccharide substances which are derived principally but not exclusively from bacterial and non-mammalian sources. Sulfatoids are typically of shorter chain length and lower molecular weight than glycosaminoglycans, but may be synthetically modified to give (a) longer chain lengths, (b) increased sulfation per unit saccharide, (c) various other chemical side groups, or (c) other properties favorable to the desired ligand-binding property and site-selective binding, uptake and accumulation property (or properties) in vivo. Sucrose and other short-chain oligosaccharides may be obtained from natural and synthetic sources.

These oligosaccharides can be rendered anionic or acidic by chemical or enzymatic derivatization with carboxylate, phosphate, sulfate or silyl side groups, or combinations thereof, at substitution ratios of up to about eight anionic or acidic substituent groups per disaccharide unit. Modified glycosaminoglycans may be derived from any of the types and sources of native glycosaminoglycans described above, and include: (1) glycosaminoglycan fragments, further defined as glycosaminoglycans with chain lengths made shorter than the parental material as isolated directly from natural sources by standard ion-exchange separation and solvent fractionation methods; (2) glycosaminoglycans chemically modified to decrease their anticoagulant activities, thereby giving "non-anticoagulant" (NAC) GAGs, prepared typically but not exclusively by (a) periodate oxidation followed by borohydride reduction; (b) partial or complete desulfation; and (c) formation of non-covalent divalent or trivalent counterion salts, principally including but not limited to salts of the more highly acidic sulfate functional groups, with principally but not exclusively: calcium, magnesium, manganese, iron, gadolinium and aluminum ions.

For purposes of this invention, a special class of such salts includes those salts formed by electrostatic or paired-ion association between the acidic or sulfate groups of acidic saccharide or glycosaminoglycan carrier, and the basic or cationic group or groups of the metal chelator or metal chelator including metal, as described above. Derivatized acidic saccharides and glycosaminoglycans are typically prepared by derivatization of various chemical side groups to various sites on the saccharide units. This may be performed by chemical or enzymatic means.

Enzymatic means are used in certain instances where highly selective derivatization is desired. Resulting chemical and enzymatic derivatives include, but are not limited to acidic saccharides and glycosaminoglycans derivatized by: (1) esterification of (a) carboxylate groups, (b) hydroxyl groups, and (c) sulfate groups; (2) oversulfation by nonselective chemical or selective enzymatic means; (3) acetylation, and (4) formation of various other ligand derivatives, including but not limited to (a) addition of sialyl side groups, (b) addition of fucosyl side groups, and (c) treatment with various carbodiimide, anhydride and isothiocyanate linking groups, and (d) addition of various other ligands.

If and when present, sulfate and sialyl side groups may be present at any compatible position of saccharide monomer, and on any compatible position of glycosaminoglycan monomers [Lindahl et al. (1978), incorporated herein by reference]. Certain of the resulting derivatized acidic saccharides and glycosaminoglycans may have desired alterations of anticoagulant activities, site-localization patterns, clearance and other biological properties. As one example of this relationship between certain classes of glycosaminoglycans and biological properties, dermatan sulfates with a native sulfate/carboxylate ratio of 1:1, are reported to have relatively low binding to normal endothelial cells, avoid displacement of endogenous heparan sulfate from endothelial-cell surfaces, have relatively high selectivity to induced endothelia at sites of disease, including thrombus, and have rapid plasma clearance, principally by the renal route; whereas heparins and oversulfated dermatan sulfates with higher sulfate/carboxylate ratios of between 2:1 and 3.7:1, are reported to have relatively higher binding for both normal and induced endothelia, to displace relatively more endogenous endothelial heparan sulfate, and to clear more slowly than dermatans [Boneu et al. (1992), incorporated herein by reference].

In a special case unique to the present invention, derivatization of the acidic saccharide and glycosaminoglycan carriers may be accompanied by the basic metal chelator itself. Although the general classes of carriers described above are particularly suitable to the present invention, it will be apparent to those skilled in the art that a wide variety of additional native, derivatized and otherwise modified carriers and physical formulations thereof, may be particularly suitable for various applications of this invention. As one representative example, the source and type of glycosaminoglycans, its chain length and sulfate/carboxylate ratio can be optimized to (1) provide optimal formulation characteristics in combination with different small and macromolecular diagnostic agents and drugs; (2) modulate carrier localization on diseased versus normal endothelium; (3) minimize dose-related side effects; (4) optimize clearance rates and routes of the carrier and bound diagnostic and therapeutic actives.

Non-covalent formulations of active and carrier afford markedly higher active-to-carrier ratios than those possible for covalent chemical conjugates. In the present invention, non-covalent binding affords a minimum of 15% active to total agent by weight [active/(active+carrier), w/w]; typically greater than about 30% (w/w); preferably at least about 50% (w/w); and frequently between about 70–99% (w/w). Covalent binding characteristically limits the percent active to (a) less than about 12% for non-protein small and polymeric carriers, (b) less than about 7% for peptide and protein carriers, including antibodies, and (c) less than about 0.5–2.0% for antibody fragments. This limitation is based on the number of functional groups available on carrier molecules which are useful in agent formulation and in vivo site localization.

It will be apparent to those skilled in the art that covalent active-carrier agent compositions of low substitution ratio may be useful for certain in vivo applications of typically narrow range, and that non-covalent active-carrier agent compositions of high substitution ratio may be useful for other in vivo applications of typically broader range. Generally, but not exclusively, covalent agents may be useful for radionuclide imaging or therapeutic applications in which only low total-body doses are needed, clearance of the non-targeted dose fraction does not cause undue toxicity, and high conjugate stability is required. Generally, but not exclusively, non-covalent agents may be particularly useful for the majority of diagnostic imaging applications and certain high-dose therapeutic applications, for which high total-body and site-localized doses are needed, and rapid clearance of the non-localized fraction of administered agent is desired in order to accelerate plasma clearance and to achieve low background levels for purposes of maximizing image contrast and minimizing systemic toxicity.

Rapid clearance is preferentially conferred by non-covalent physical formulations due to their capacity to give controlled dissociation or release of the active from the carrier. Such controlled release allows the diagnostic or therapeutic active, to dissociate from its carrier at a programmed rate which is consistent with rapid site localization of a significant fraction of the total administered dose. In instances where the carrier is polymeric and hence clears more slowly, this selectively accelerates clearance of the active.

It will be apparent to those skilled in the art that such controlled release can also be achieved for actives which are chemically conjugated to their carriers via chemical linkers, including peptide linkers, which are susceptible to cleavage by body enzymes. However, this latter means of facilitated clearance: (a) gives much longer clearance times than do physical formulations, (b) depends on endogenous enzyme levels and inhibitors which typically differ from subject to subject, from health to disease, and from one stage of disease to another. Hence, physical formulations have substantial advantages over chemical conjugates from the standpoints of both (a) high payload, and (b) accelerated clearance.

These properties of the present formulations represent additional substantial improvements over prior, non-selective and covalently conjugated active-carrier agents. The resulting agents are broadly useful for: (a) MRI contrast and spectral enhancement, Ultrasound contrast enhancement, and X-Ray contrast enhancement, where relatively high administered doses may be favored or required; (b) Nuclear Medical or Radionuclide imaging and therapy, where enhanced clearance of the non-targeted dose may be favored or required: and (c) certain high-dose, extended-release or sustained-effect therapy may be favored or required. Such therapeutic agents include but are not limited to those useful at a broad variety of organ sites and medical indications, for the treatment of: (a) acute vascular ischemia, acute infarct, acute vascular damage, shock, hypotension, restenosis, proliferation of neo-vessel, parenchymal cells or other pathological proliferations; and (b) the following classes of disease: vascular, parenchymal, mesenchymal, endothelial, smooth muscle, striated muscle, adventitial, immune, inflammatory, bacterial, fungal, viral, degenerative, neoplastic, genetic and enzymatic.

MRI contrast enhancement is one important indication for which high payload and controlled release of active are important unique advantages in addition to site selective localization (see below). A still further advantage is the hydrophilic form of carrier, which maximizes proximal water diffusion and binding of the paramagnetic active. This last property is required for optimal efficacy and minimal toxicity, because MRI paramagnetic T1-Type contrast agents require unimpeded water diffusion to within a very short distance of the localized metal ion in order to achieve effective paramagnetic relaxation and T1 contrast. Additionally, MRI image instrumentation and image acquisition are inherently both of low sensitivity; and these limitations remain even at the highest clinically acceptable field strengths and gradients and at the optimal radiofrequency pulse sequences.

MRI paramagnetic agents have been prepared as stabilized liposomes, which contain up to about 22% of active (w/w). However, their hydrophobic lipid bilayers markedly impede water diffusion into the liposome core active. This decreases their efficacy per unit dose relative to the hydrophilic controlled-release carriers of the present invention. There is an additional disadvantage of the reported MRI liposome formulations as follows: aside from localization in normal liver and reticuloendothelial-phagocytic organs, they have not demonstrated effective site-localization at sites of tumors, infarcts and other focal pathology within tissue sites.

For purposes of this invention, metal ions generally useful for chelation in paramagnetic T1-Type MRI contrast agent compositions and uses may include divalent and trivalent cations selected from the group consisting of: iron, manganese, chromium, copper, nickel, gadolinium, erbium, europium, dysprosium and holmium. Chelated metal ions generally useful for radionuclide imaging and compositions and uses, and in radiotherapeutic compositions and uses, may include metals selected from the group of: gallium, germanium, cobalt, calcium, rubidium, yttrium, technetium, ruthenium, rhenium, indium, iridium, platinum, thallium and samarium. Metal ions useful in neutron-capture radiation therapy may include boron and others with large nuclear cross sections. Metal ions useful in Ultrasound contrast and X-Ray contrast compositions and uses may, provided they achieve adequate site concentrations, include any of the metal ions listed above, and in particular, may include metal ions of atomic number at least equal to that of iron.

For purposes of this invention, agents for therapeutic composition and uses in chelating internal body iron, copper or both, in order to make these metals unavailable locally (1) which are typically required for neovascularization, or (2) which cause and amplify local tissue injury [Levine (1993), incorporated herein by reference], include the carrier with basic metal chelator in one or both of the following forms: (a) carrier plus chelator without metal ion; and (b) carrier plus chelator with metal ion added and chelated in the composition at a formation constant lower or equal to that of the internal body metal which is to be chelated by metal ion exchange into the respective basic metal chelator of the composition (see below). Such weakly chelated metal ions of the composition may include one selected from the group of: calcium, manganese, magnesium, chromium, copper, zinc, nickel, iron, aluminum, cobalt, gadolinium or other exchangeable ion. Metal ions useful for inclusion in compositions for other therapeutic uses may include the divalent and trivalent cations selected from the group of magnesium, manganese, chromium, zinc and calcium, iron, copper and aluminum. It will be obvious to those skilled in the art that various one of the preceding metal ions can be used in combination with basic metal chelators, for alternative indications than those specified above, and that metal ions other than those listed above may, under certain conditions, be useful in the uses and indications listed above.

The compositions described in this invention give surprising and unexpected improvements of performance and use which include:

(1) retained high association of active plus carrier during in vitro dialysis and in vivo targeting;

(2) selective binding of the active plus carrier to induced endothelia at sites of disease;

(3) following intravenous administration, very rapid (2–7 min) localization at the diseased site, due to rapid selective endothelial binding, envelopment and extravasation of the carrier plus metal chelator across disease-induced endothelia (including histologically non-porous endothelia);

(4) widespread uptake throughout the diseased tissue site;

(5) sustained retention (multiple hours to days) within the diseased site in combination with (6) rapid plasma clearance (minutes) of the non-targeted fraction;

(7) moderately slow, polymeric diffusion rates within the diseased tissue matrix, allowing differentiation of functional tissue subregions based on differences in perfusion of viable and non-viable subregions;

(8) capacity to selectively image solid tumors or acute vascular and myocardial infarcts at body sites, as well as at brain and central nervous system sites, with substantially improved selectivity, sensitivity, improved delineation of tumor and infarct boundaries at both very short and prolonged post-injection intervals, and improved detection of small tumor metastases, including those at liver and lung sites.

Diagnostic and drug enhancement can be made to occur by a number of mechanisms, the principal ones being:
1. Effective TARGETING to tissue sites of disease;
2. STABILIZATION during both storage and plasma transit;
3. Prolonged RETENTION at the site of disease, giving a markedly increased area under the curve at the tissue site;
4. RAPID CLEARANCE of the non-TARGETED fraction, thereby reducing background signal in imaging applications and reducing normal organ exposure and systemic toxicity in therapeutic applications.

Five further significant advantages of the present compositions and uses are:
1. Simple formulations of active and carrier;
2. Stabilization of diagnostic and therapeutic actives on the shelf and during plasma transit;
3. Rapid site localization and sustained site retention;
4. Rapid clearance of the non-targeted fraction;
5. Availability of low toxicity carbohydrate carriers from natural sources and, where needed, modification or derivatization by straightforward synthetic means.

Acidic or anionic saccharides and glycosaminoglycans have unique mechanisms of site localization and retention in vivo. They bind to the body's endothelial determinants which are selectively induced on the microvascular barrier by underlying tissue disease. Previous approaches to site targeting were directed at antigenic determinants. However, because these determinants are typically located in sequestered sites within the tissues, in other words at sites across the endothelial barrier and not within the bloodstream and not on its endothelial surface, carriers and agents injected into the bloodstream had no effective means to recognize and localize in the region of these target antigens. Stated another way, previous approaches ignored the major problem of inappropriate carrier distribution which resulted from its failure to recognize the vascular access codes required for efficient extravasation at disease sites. Hence, these carriers failed to effectively load the relevant tissue sites with effective concentrations of their bound actives.

The biological address of a disease site can be viewed in a fashion similar to that of a postal address, wherein effective carrier substances must (1) first recognize the "state" address of the signal endothelium induced by proximal tissue disease; (2) next extravasate and load the "city" address of the extracellular tissue matrix with locally effective doses of the diagnostic and therapeutic actives; and (3) finally bind and load the "street" address of the target cells and antigens. Previous approaches to site delivery have attempted to recognize the "street" address without first recognizing the "state" and "city" addresses.

The reason that acidic saccharide and glycosaminoglycan systems work substantially better than previous antigen-recognition approaches, is that they recognize the newly induced signals which the body uses to attract and target white blood cells into sites of tissue disease. When disease strikes at a local site, it initiates a cascade of local mediators within the tissue matrix and at the endothelial-blood interface which signal the blood cells and central body systems that inflammatory and immune cells are required within the tissue site. These mediators include cytokines, chemoattractants, cytotaxins, induced cell-surface adhesions, selectins and integrins, and various tissue-derived and blood-borne, soluble and cell-surface procoagulants. White cell accumulation begins within minutes and continues over days to weeks, depending on the nature, severity and persistence of local disease and the continued generation of tissue mediators and trans-endothelial signals.

As has now been reported and reviewed in detail [Ranney (1990); Ranney (1992); Bevilaqua et al. (1993); Bevilacqua et al. (1993); Travis (1993); Sharon et al. (1993), all incorporated herein by reference], tumors, infarcts, infections, inflammatory diseases, vascular disorders, and other focal diseases, characteristically induce the release of such host mediators, or cytokines, from resident macrophages and local tissue matrix. In certain diseases, alien mediators such as bacterial lipopolysaccharides (LPS), viral RNA, and tumor-derived inducers, including EMAP II, and chemoattractants may also be released. Although additional mediators remain to be elucidated, the principal ones have now been defined and include: interleukin 1 (IL-1), tumor necrosis factor (TNF), transforming growth factor beta (TGF-beta), Lipopolysaccharide (LPS), single and double stranded nucleotides, various interferons, monocyte chemoattractant protein (MCP), interleukin 8 (IL-8), interleukin 3 (IL-3), interleukin 6 (IL-6), tumor-derived inducers and chemoattractant peptides (as above), various prostaglandins and thromboxanes. Certain ones of the preceding mediators induce the local generation and release of metalloproteinases, and these in turn, expose latent tissue binding sites, including intact and partially cleaved integrins, RDGS peptides, laminin, collagen, fibronectin, and cell-surface core-protein components of glycosaminoglycans.

Cytokines, monocyte chemoattractant protein (MCP), tissue metalloproteinases, and proteolytic tissue matrix fragments directly induce the local endothelium to become adhesive for circulating white blood cells, including neutrophils, monocytes and lymphocytes. The induced endothelial adhesive molecules (adhesins) include: P-selectin (gmp-140), E-selectin (ELAM-1), intercellular cell adhesion molecule (ICAM-1), vascular cell adhesion molecule (VCAM-1), inducible cell adhesion molecule, (INCAM-110), von Willebrand's factor (vWF, Factor VIII antigen) (see below for disease states which activate these respective types of endothelial adhesins). Additional cascades become activated which indirectly amplify endothelial adhesiveness. These include (1) coagulation factors, especially fibronectin, tissue factor, thrombin, fibrinogen, fibrin, and their split products, especially fibronectin split products and fibrinopeptide A; (2) platelet-derived factors: platelet activating factor (PAF), glycoprotein IIb/IIIa complex; (3) white-cell (a) L-selecting, and (b) integrins, including VLA-4 (very late antigen 4); and (4) numerous complement factors.

The preceding pathologic processes and signals are involved, directly or indirectly as follows, in the binding and site localization of acidic carriers, including acidic saccharides (AC) and glycosaminoglycans (GAGs) (Note that in the following outline, potential tissue binding sites are designated as "GAGs" and "ACs").

1. Local tissue diseases induce local cytokines and mediators, as described above.
2. These cytokines and mediators induce tissue chemoattractants, including MCP and IL-8, which comprise a family of arginine-rich, 8 Kd, heparin-binding proteins reported to bind GAGs/ACs [Huber et al. (1991), incorporated by reference herein];
3. The cytokines and mediators of No. 1, above, induce the local endothelium to express P-selectin, the vascular cell adhesion molecular (VCAM-1), inducible cell adhesion molecule (INCAM-110), and von Willebrand's factor (vWF, Factor VIII antigen), which are reported binding determinants for GAGs/ACs [Bevilaqua et al. (1993); Bevilacqua et al. (1993)]; P-selectin is reported to bind GAGs [Bevilacqua et al. (1993)];

4. Integrins, including but not limited to VLA-4, are induced on circulating white blood cells, including lymphocytes, during various disease processes (see below); VLA-4 has a distinct binding site on the (induced) endothelial selectin, VCAM-1 (see No. 3, above); fibronectin, which is abundantly present in plasma and also available from tissue sites, has a distinct and separate binding site on VLA-4 [Elices et al. (1990)]; since fibronectin has specific binding sites for GAGs/ACs [Bevilaqua et al. (1993)], these amplification steps provide a strong additional mechanism for site localization of GAGs/ACs;

5. The chemoattractants, MCP and IL-8, lymphocyte integrin, VLA-4, platelet factor, PAF, and coagulation factors, thrombin, fibronectin and others, diffuse from local tissue and blood, respectively, bind to the induced endothelial selectins, and amplify adhesiveness and activation at the initial endothelial P-selectin sites for GAGs/ACs [Elices et al. (1990); Lorant et al. (1993) ];

6. Tissue metalloproteinases become activated and expose new binding sites for GAGs/ACs in the tissues which underlie the activated endothelia. These new tissue binding sites include as follows [Ranney (1990); Ranney (1992); Travis (1993); Bevilaqua et al. (1993)]:
   a. fibronectin fragments;
   b. collagen fragments;
   c. laminin fragments;
   d. RGDS peptides;
   e. Exposed core proteins of GAGs;

7. White blood cells are attracted to the site, become activated and release additional proteolytic enzymes, thereby amplifying No. 6 and increasing the exposure of binding sites for GAGs/ACs in the tissue matrix.

8. GAG/AC carriers selectively bind the induced and exposed determinants listed in Nos. 1–7, above, giving immune-type localization which is specific for induced binding sites (lectins) at the lectin-carbohydrate level characteristic of white-cell adhesion;

9. In cases where the carrier substance has multivalent binding to the target binding substance, including for example, cases in which the carrier is an acidic oligosaccharide or polysaccharide or an acidic glycosaminoglycan, multivalent binding of the endothelial surface induces rapid extravasation of the carrier and bound active, and results in substantially increased loading of the underlying tissue matrix, relative to that achieved by antibodies, liposomes, and monovalent binding substances, such as hormones and monovalent-binding sugars;
10. Adhesion of GAGs/ACs to induced and exposed tissue binding sites, reduces plasma backdiffusion of GAGs/ACs and their bound actives, thereby giving sustained retention within the tissue site;
11. Controlled release of the diagnostic or drug active from carriers comprising GAGs/ACs occurs gradually within the diseased site, thereby resulting in targeted controlled release;
12. Tumor cells, microbial targets and damaged cellular targets within the tissue site, may selectively take up the GAG/AC plus bound diagnostic or drug active, based respectively, on: induced tumor anion transport pathways, microbial binding sites for GAGs/ACs, and proteolytically exposed cell-surface core proteins [Ranney 07/880,660, 07/803,595 and 07/642,033]- - - Fe uptake by hepatomas, Cr4S uptake by - - - ); [Kjellen et al. (1977)]
13. In cases where the carriers are hydrophilic or essentially completely hydrophilic, these carriers cause their bound actives to migrate out (permeate) into a small rim of normal tissue around each focus of disease, typically comprising a rim about 30–75 um thick; however, such carriers undergo selective uptake by abnormal cells within tissue site and preferentially avoid uptake by normal cells within the site, thereby giving:
    a. In cases of diagnostic imaging applications: very sharp definition of the boundary between tumors or infarcts and the surrounding normal tissues;
    b. In cases of therapeutic applications:
       (1) protection against spread of disease at the rim;
       (2) relative protection of normal cells within and adjacent to the site of disease, from uptake of cytotoxic drugs.
14. In the case of hydrophilic carriers, including but not limited to GAGs/ACs, the non-targeted fraction of active is cleared rapidly and non-toxically, thereby minimizing:
    a. in imaging uses, background signal intensity;
    b. in all uses:
       (1) normal organ exposure; and
       (2) systemic side effects.

Regarding the above outline, the following A. cytokines and mediators; and B. selectins, integrins and adhesins are reported to be induced by various disease states in addition to that reported for tumors, above [Bevilaqua et al. (1993)]. Representative non-oncologic induction also occurs as follows.

A. Cytokines and mediators.
   1. MCP: Experimental autoimmune encephalomyelitis in mice [Ransohoff et al. (1993)];
   2. IL-8: Neovascularization: [Strieter et al. (1992)];
   3. PAF: Reperfused ischemic heart [Montrucchio et al. (1993)].

B. Selectins, Integrins and Adhesins.
   1. ELAM-1:
      a. Liver portal tract endothelia in acute and chronic inflammation and allograft rejection [Steinhoff et al. (1993)];
      b. Active inflammatory processes, including acute appendicitis [Rice et al. (1992)].
   2. VCAM-1:
      a. Simian AIDS encephalitis [Sasseville et al. (1992) ].
      b. Liver and pancreas allograft rejection [Bacchi et al. (1993)].
   3. INCAM-110: Chronic inflammatory diseases, including sarcoidosis [Rice et al. (1991)].
   4. Integrin, beta 1 subunit cell adhesion receptor: inflammatory joint synovium [Nikkari et al. (1993)].

It is apparent from the above, that broad categories and many specific types of focal tissue disease may be addressed by the carriers and actives of the present invention, both for diagnostic and therapeutic uses, including tumors, cardiovascular disease, inflammatory disease, bacterial and viral (AIDS) infections, central nervous system degenerative disorders, and allograft rejection. It will also be obvious to those skilled in the art, that numerous additional disease states may be selectively addressed by the carriers disclosed in this invention.

The site selectivity of glycosaminoglycans (GAGs) appears to mimic an immune mechanism at the level of white-cell targeting rather than antibody targeting. Because antibodies have extremely high specificities, they characteristically miss major subregions of disease foci (typically as great as 60% of tumor cells are nonbinding). Recently, one of the GAG-binding determinants of endothelial P-selectin has been identified as sialyl Lewis x. Others are in the process of identification. Notably, the available nonvalent oligosaccharides specific for sialyl Lewis x suffer from two critical problems:

1. They are exceedingly expensive materials, available only by synthetic or semi-synthetic means, and hence, are not cost effective;

2. They do not bind effectively at diseased sites under in vivo conditions, apparently due to the inability as monomeric binding substances to displace endogenous interfering substances which are pre-bound at these sites.

There are two apparent benefits of the relatively broader range of GAG specificities and redundancy of GAG binding sites present on diseased endothelium and tissue matrix:

1. GAGs allow a broader range of tumors and diseases to be targeted than that possible with antibodies (which typically target only a subset of histologic types — — — even within a given class of tumor, and hence, are typically ineffective from both a medical and cost/development standpoint);

2. GAGs are projected to be effective over a greater time interval, from early onset of disease to progression and regression.

Despite the broader targeting specificity of GAGs over antibodies, their favorable clearance and avoidance of uptake by normal cells reduce systemic and local toxicities, even though more than one type of disease site may undergo targeted accumulation of the diagnostic/drug within its extracellular matrix.

The polymeric and multivalent binding properties of GAGs both are very important for optimal site localization of the attached diagnostic/drug. GAG molecular weights of ca. 8,000 to 45,000 MW are important in order to:

1. Restrict initial biodistribution of the diagnostic/drug to the plasma compartment and thereby maximize the quantity of agent available for site targeting;

2. Displace endogenous interfering substances which are pre-bound to diseased endothelium;

3. Induce active endothelial translocation of the GAG-diagnostic/drug into the underlying tissue matrix;

4. Afford rapid clearance and markedly reduced side effects of the attached actives.

SUMMARY OF THE INVENTION

The present invention encompasses novel agents comprising cationic or chemically basic metal chelators in association with hydrophilic carriers of anionic or chemically acidic saccharides, sulfatoids and glycosaminoglycans. In certain embodiments of the invention, the agents also comprise chelated metals and metal ions. The binding of the metal chelators to the carriers is stabilized by covalent or non-covalent chemical and physical means. In some embodiments, novel non-covalently bound compositions give uniquely high payloads and ratio of metal chelator to carrier, ranging from a low of about 15% metal chelator by weight, to a characteristic range of 70% to 90% metal chelator by weight. Specific embodiments comprise deferoxamine, ferrioxamine, iron-basic porphine, iron-triethylenetetraamine, gadolinium DTPA-lysine, gadolinium DOTA-lysine and gadolinium with basic derivatives of porphyrins, porphines, expanded porphyrins, Texaphyrins and sapphyrins as the basic or cationic metal chelators, which are in turn, bound to acidic or anionic carriers, including one or more of acidic or anionic saccharides, and including sulfated sucrose, pentosan polysulfate, dermatan sulfate, oversulfated dermatan sulfate, chondroitin sulfate, oversulfated chondroitin sulfate, heparan sulfate, beef heparin, porcine heparin, non-anticoagulant heparins, and other native and modified acidic saccharides and glycosaminoglycans.

Methods of magnetic resonance image (MRI) contrast enhancement are a particular embodiment of the present invention which confirm very rapid, carrier-mediated, site-selective in vivo localization and sustained site retention of metal-chelator compositions, based on stable binding of the metal chelator and carrier during in vivo plasma transit, allowing site localization following intravenous administration. Rapid and selective endothelial-site binding, facilitated rapid extravasation into underlying tissue sites, site accumulation, sustained site retention, together with rapid clearance of the non-site-localized fraction are also demonstrated by the use of the compositions of the present invention in the selective MRI contrast enhancement of tumors and cardiovascular infarcts.

Surprising and unexpected improvements of selectivity, mechanism of localization and cellular uptake, and MRI contrast sensitivity are shown for metal chelates having standard paramagnetic potencies. Further advantages of the use of the compositions and methods of the present invention are delineated in the examples (infra) including special histologic staining evidence which confirms the site-selective endothelial binding, extravasation, tissue matrix accumulation and cellular uptake mechanism. Selective localization and MRI imaging efficacy are also shown to occur when paramagnetic metal chelator actives are administered in carrier-bound form but not in free form.

In its most general embodiment, the present invention is an agent comprising a chelator for metal ions, said chelator having a cationic group and being bound to an anionic, hydrophilic carrier. In alternate embodiments, the chelator for metal ions which has a cationic group is bound to an anionic, hydrophilic carrier by non-covalent electrostatic binding. And, in certain alternate embodiments the invention comprises an agent comprising a basic chelator for metal ions, said chelator having a cationic group and being covalently bound to an anionic, hydrophilic carrier. In the particular embodiments of the invention in which the chelator is not covalently bound to the carrier, the said chelator may be basic.

In certain embodiments of the present invention, the agent which comprises a chelator for metal ions and having a cationic group bound to an anionic hydrophilic carrier may further comprise a chelated metal ion, and in particular it may further comprise a paramagnetic metal ion. The agents of the present invention, in particular those which comprise the chelator for metal ions non-covalently bound to the carrier may be further defined as being at least about 15 weight percent chelator. Preferably, the chelator has a formation constant for paramagnetic metal ions of at least about $10^{14}$.

Those agents of the present invention which comprise a metal ion will preferably comprise a metal ion selected from the group consisting of iron, manganese, chromium, copper, nickel, gadolinium, erbium, europium, dysprosium and holmium. In certain embodiments, the agents of the present invention may even comprise a metal ion selected from the group consisting of boron, magnesium, aluminum, gallium, germanium, zinc, cobalt, calcium, rubidium, yttrium, technetium, ruthenium, rhenium, indium, iridium, platinum, thallium and samarium. It is understood that other metal ions which are functionally equivalent to the listed metal ions are also included and would fall within the scope and spirit of the presently claimed invention.

In certain preferred embodiments of the invention, the agents comprise a carrier wherein said carrier is an acidic saccharide, oligosaccharide, polysaccharide or glycosaminoglycan. The carrier may also be an acidic glycosaminoglycan or sulfatoid. In particular, the carrier may be, but is not limited to heparin, desulfated heparin, glycine-conjugated heparin, heparan sulfate, dermatan sulfate, chondroitin sulfate, hyaluronic acid, pentosan polysulfate, dextran sulfate, sulfated cyclodextrin or sulfated sucrose.

In certain embodiments of the invention, the chelator is a chelator of iron ions. Preferably the chelator is a hydroxamate, and more preferably it is deferoxamine. In certain preferred embodiments the chelator together with the metal ion is ferrichrome, ferrioxamine, enterobactin, ferrimycobactin or ferrichrysin. In a particularly preferred embodiment, the chelator is deferoxamine, the carrier is heparin, or a heparin fragment and the agent further comprises iron(III). In an alternate embodiment, the chelator is deferoxamine and the carrier is dermatan sulfate or a dermatan sulfate fragment and the agent may further comprise chelated iron(III).

In a certain embodiment, the invention may also comprise deferoxamine bound to a carrier selected from the group consisting of heparin, heparan sulfate, dermatan sulfate or chondroitin sulfate, and may further comprise a metal ion. The agents of the present invention may also comprise a chelator which is a porphine, porphyrin, sapphyrin or texaphyrin and which may further comprise a metal ion, and preferably an iron ion or a gadolinium ion.

In a particularly preferred embodiment the agent of the present invention may comprise a chelator which is 5,10,15,20-Tetrakis(1-methyl-4-pyridyl)-21H,23-porphine, a carrier which is heparin and a chelated iron ion. In certain embodiments, the chelator may also be a polyaminocarboxylate or macrocyclic, and preferably a basic or amine derivative of diethylenetriaminetetraacetate, or more preferably a basic or amine derivative of 1,4,7,10-tetraazacyclododecane-N,N',N",'"-tetraacetate (DOTA). In the agents of the present invention, the carrier may also be defined further as being complementary to endothelial determinants selectively induced at disease sites.

In a certain embodiment, the present invention is an image-enhancing agent or spectral-enhancing agent to enhance images arising from induced magnetic resonance signals, the agent comprising ferrioxamine covalently conjugated to heparin by 1-ethyl-3-(3-dimethylaminopropyl) carbodiimide, N-ethoxycarbonyl-2-ethoxy-1,2-dihydroquinoline, or carbonyldiimidazole. Alternatively, the invention is a spectral-enhancing agent to enhance images arising from induced magnetic resonance signals, the agent comprising Gd(III)diethylenetriaminepentaacetate covalently conjugated to one of heparin, dermatan sulfate or chondroitin sulfate. In another alternative, the invention is an agent for in vivo imaging, the agent comprising a basic chelator for metal ions and chelated metal ion, said chelator being bound by non-covalent electrostatic binding to a hydrophilic carrier selected from the group consisting of heparin, desulfated heparin, glycine-conjugated heparin, heparan sulfate, dermatan sulfate, chondroitin sulfate, hyaluronic acid, pentosan polysulfate, dextran sulfate, sulfated cyclodextrin or sulfated sucrose. The agent for enhancing body imaging preferably comprises deferoxamine, chelated Fe(III) and a glycosaminoglycan carrier bound to said deferoxamine and more preferably the glycosaminoglycan carrier is dermatan sulfate, and/or the Fe(III) is a radiopharmaceutical metal ion, and most preferably the radiopharmaceutical metal ion is $^{59}$iron or $^{67}$gallium.

In an alternate embodiment, the invention is an agent for enhancing body imaging, the agent comprising diethylenetriaminepentaacetate-lysine, chelated Gd(III) and a glycosaminoglycan carrier bound to said diethylenetriaminepentaacetate-lysine. Alternatively, the invention is an agent for enhancing body imaging, the agent comprising DOTA-lysine, chelated Gd(III) and a glycosaminoglycan carrier bound to said 1,4,7,10-tetraazacyclododecane-N,N',N",N"'-tetraacetate-lysine (DOTA-lysine). In a particular embodiment, the invention is an agent comprising ferrioxamine bound by non-covalent electrostatic binding to dermatan sulfate.

It is understood that any of the agents of the present invention as described in the above paragraphs or in the appended claims may be defined further as being in a combination with at least one of a buffer, saccharide, sulfated saccharide, or salt, to produce an osmotic strength suitable for parenteral administration, and as being an aqueous solution or a lyophilized or dry preparation suitable for aqueous reconstitution having the desired osmotic strength, and wherein said agent is aseptic or sterile.

Another embodiment of the invention is a method of enhancing magnetic resonance images or spectra in vertebrate animals comprising administering to said animal an effective amount of an agent of the invention which comprises the metal ion chelator, the carrier as described and a paramagnetic ion. In particular, the invention is a method of enhancing in vivo images arising from induced magnetic resonance signals, comprising the steps of administering to a subject an effective amount of an agent of the present invention which comprises a paramagnetic ion, exposing the subject to a magnetic field and radiofrequency pulse and acquiring an induced magnetic resonance signal to obtain a contrast effect.

In an alternative embodiment, the invention is a method of enhancing in vivo images, comprising the steps of administering to a subject an effective amount of an agent of the present invention which comprises a chelated metal ion, exposing the body to ultrasound or X-rays and measuring signal modulation to obtain a contrast effect.

In another embodiment, the invention is a method of obtaining in vivo body images comprising administering to a subject an effective amount of an agent of the invention which comprises a metal ion wherein the metal ion is a radioisotope and measuring scintigraphic signals to obtain an image.

In another embodiment, the invention is a method of treating vascular disease, comprising administering to a subject a therapeutically effective amount of an agent of the present invention, and preferably an agent which comprises a metal ion.

BRIEF DESCRIPTION OF THE DRAWINGS

The following drawings and figures are presented to illustrate preferred embodiments of the present invention and their uses in MRI contrast enhancement. These examples are purely illustrative, and do not in any way delimit the full scope of the present invention.

FIG. 1D is the experimental infrared spectrum of L-lysine covalently conjugated to DTPA by 1-ethyl-3-(3dimethylaminopropyl) carbodiimide (EDC) linkage (see Example 3). Note the changes (height, width and loss of splitting) in signature peaks in the range of 1250–1700 wavenumbers, which indicate covalent conjugate formation.

FIGS. 2A–4D and 8A–C show T1-weighted MRI images (TR/TE=800/45, 550/23 and 600/45) performed at 1.0 and 1.5 Tesla, before (Pre) and after (Post) intravenous (i.v.) injection of Ferrioxamine:Dermatan Sulfate Selective Paramagnetic Contrast Agent, prepared as in Examples 2 and 5, and injected i.v. at a Ferrioxamine dose of 0.155 mmol/Kg into Fisher 344 female rats, with syngeneic breast adenocarcinoma inoculated previously into the liver, such that tumor diameters at the time of imaging are between 1.0 cm and 2.5 cm.

FIG. 2A Precontrast image of liver (tumor not conspicuous).

FIG. 4D Liver image at 42 MPI of Ferrioxamine:Dermatan Sulfate Selective MRI Contrast Agent. Note: continued strong enhancement of main tumor and metastasis at prolonged postcontrast interval, at high, sustained sensitivity, and with continued delineation of tumor boundaries in both nodules (selectivity), plus delineation of the very small non-perfused region centrally within the 2-mm liver metastasis.

FIG. 8A T1-weighted (TR/TE=600/45) image of Lung Field in rat with primary liver breast tumor. Note that the lung metastases (2-mm to 3-mm nodules) are only faintly conspicuous Precontrast.

FIG. 8B Lung Field of same rat at 12 MPI. Note the marked improvement in sensitivity of tumor detection (conspicuity) due to selective, bright enhancement of the lung metastases. Also note the sharpness of tumor boundaries.

FIG. 8C Same Lung Field at 17 MPI—showing sustained enhancement and sustained sharpness of tumor boundaries. By comparison, the rapid diffusion rates of Gd:DTPA lead to rapidly fuzzy boundaries at early times; and thereby also decrease the sensitivity of detecting pulmonary metastases.

FIG. 9A Precontrast image for Ferrioxamine:Dermatan Sulfate Selective Contrast Agent.

FIG. 9B 7 MPI of Ferrioxamine:Dermatan Sulfate, liquid form at a ferrioxamine concentration of 0.166 mmol/mL. Note the strong enhancement of Outer Rim and Vascular array which fans out from the tumor pedicle.

FIG. 9C Same as 9B, except 20 MPI. Note the sustained, discrete enhancement of elements in FIG. 9B FIG. 9D Same as 9C, except 40 MPI. Note the sustained contrast and delineation of Outer Rim.

FIG. 9E Same as 9D, except 60 MPI. Note the onset of contrast fading.

FIG. 10A Precontrast image for Gd:DTPA dimeglumine Nonselective Contrast Agent.

FIG. 10B 7 MPI of Gd:DTPA dimeglumine. Note that the Outer Rim is not well delineated, even at this very early post-contrast interval.

FIG. 10C Same as 10B, except 20 MPI. Note the marked early contrast fading overall, with some agent sequestration seen at the central, poorly perfused (cystic) regions of tumor (as is typically reported for Gd:DTPA when used for imaging at body sites).

FIG. 10D Same as 10C, except 40 MPI. Note that enhancement is nearly reverted to background levels.

FIG. 10E Same as 10D, except 60 MPI. No residual contrast, except for central cystic regions.

FIG. 11A Precontrast image.

FIG. 11B 7 MPI, showing strong enhancement of infarct by Ferrioxamine:Dermatan Sulfate Agent, and in particular delineating the boundary of the infarct—putatively the boundary of the marginal zone. Note the central darker region—putatively the irreversible central infarct zone.

FIG. 11C 20 MPI, showing sustained strong enhancement and zones as above.

FIG. 11D 40 MPI, same as 11C, except filling in of central zone; absence of significant overall contrast fading. NOTES: (1) injection of Ferrioxamine Agent Alone at 0.155 mmol/Kg, gives no detectable enhancement (images not shown); (2) infarct sizes and positions are documented by double dye infusion methods immediately after imaging.

FIG. 12A Precontrast image for Ferrioxamine:Dermatan Sulfate Selective Contrast Agent.

FIG. 12B 7 MPI of Ferrioxamine:Dermatan Sulfate, lyophilized reconstituted to a Fe(III) concentration of 0.415 mmol/mL. Note the very strong enhancement of the entire Outer Rim of tumor.

FIG. 12C Same as 12B, except 20 MPI. Note the sustained, very strong enhancement and delineation of Outer Rim.

FIG. 12D Same as 12C, except 40 MPI. Note the sustained very strong enhancement of Outer Rim with the Central Tumor now also starting to enhance brightly. Also note there is virtually no contrast fading at 40 minutes.

FIG. 13A Precontrast image for Gd(III):DTPA-Lys:Dermatan Sulfate Selective Contrast Agent.

FIG. 13B 7 MPI of Gd(III):DTPA-Lys:Dermatan Sulfate, at 0.415 mmol/mL. Note the exceedingly strong enhancement of the entire Outer Rim as well as Central Tumor. This is consistent with the higher paramagnetic potency of Gd:DTPA chelate, R1=4.3 [mmol.sec]-1, relative to ferrioxamine chelate, R1=1.5–1.8 [mmol.sec]-1.

FIG. 13C Same as 13B, except 20 MPI. Note the sustained, very strong absolute enhancement Outer Rim. Also note additionally strong enhancement of the central vascular array (as differentiated from cystic sequestration).

FIG. 13D Same as 13C, except 40 MPI. Note sustained enhancement of Outer Rim, with overall enhancement just beginning to fade at 40 minutes, but absolute enhancement remaining as bright or brighter in all regions relative to Ferrioxamine:Dermatan Sulfate.

FIG. 14A Precontrast.

FIG. 14B 7 MPI.

FIG. 14C 20 MPI.

FIG. 14D 40 MPI. Note the slightly greater enhancement of Tumor Rim and greater definition of the vascular array at all times, in relation to Ferrioxamine bound to Native Dermatan Sulfate (above)

FIG. 15A Precontrast.

FIG. 15B 7 MPI.

FIG. 15C 20 MPI.

FIG. 15D 40 MPI. Note the moderately greater enhancement of Tumor Rim and greater definition of the vascular array at all times, in relation Ferrioxamine bound to Native Dermatan Sulfate (above).

FIG. 16A Precontrast.

FIG. 16B 7 MPL.

FIG. 16C 20 MPI.

FIG. 16D 40 MPI. Note the very homogeneous enhancement of Outer Rim and Central Tumor at virtually all post-contrast times, in relation to the differential Rim enhancement achieved by essentially all of the other GAG carriers. This property may be useful in certain therapeutic applications.

DETAILED DESCRIPTION OF THE PREFERRED EMBODIMENTS

Figure 1A:
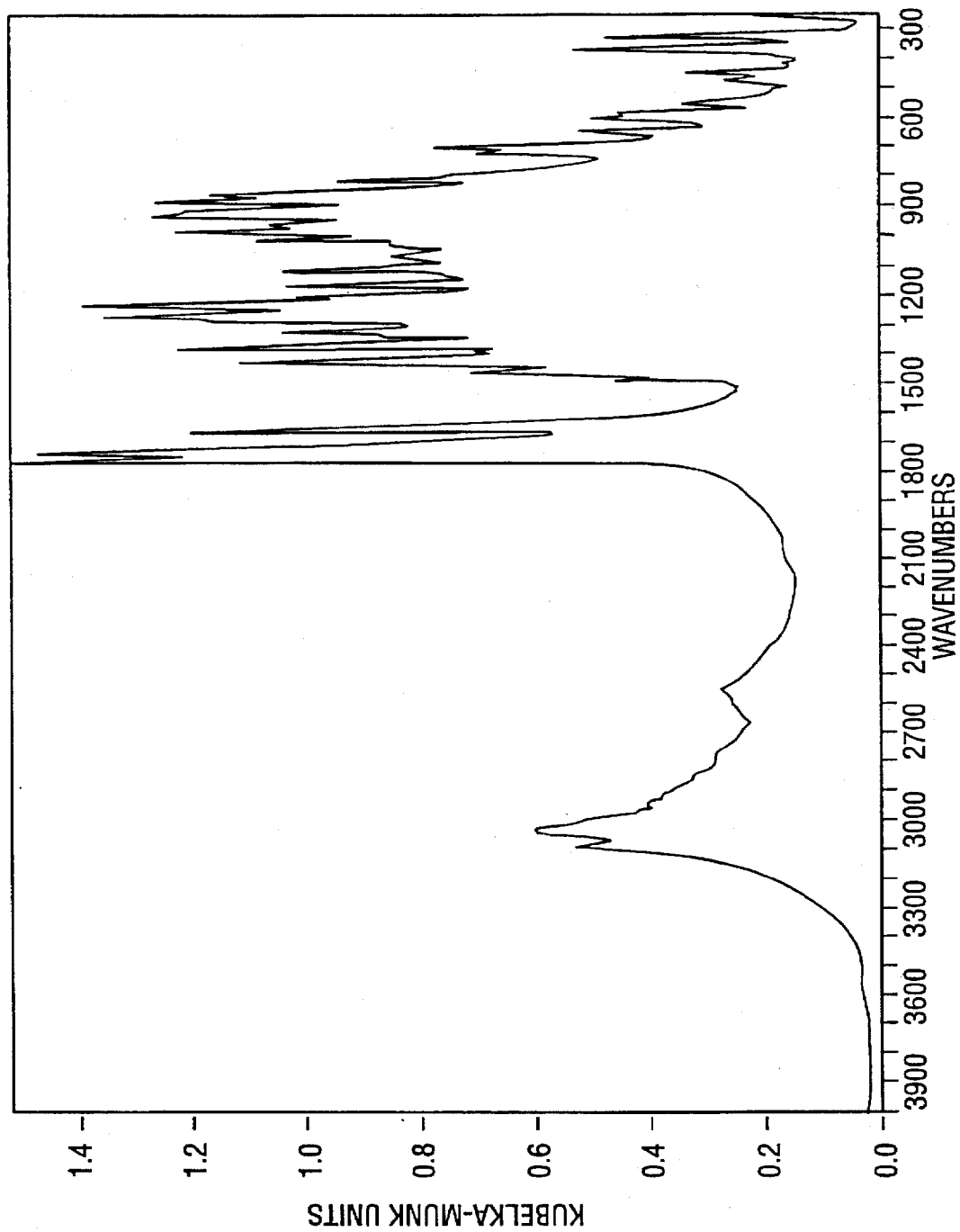
FIG. 1A is a control infrared spectrum of diethylenetriaminetetraacetate (DTPA) substrate (see Example 3).
Figure 1B:
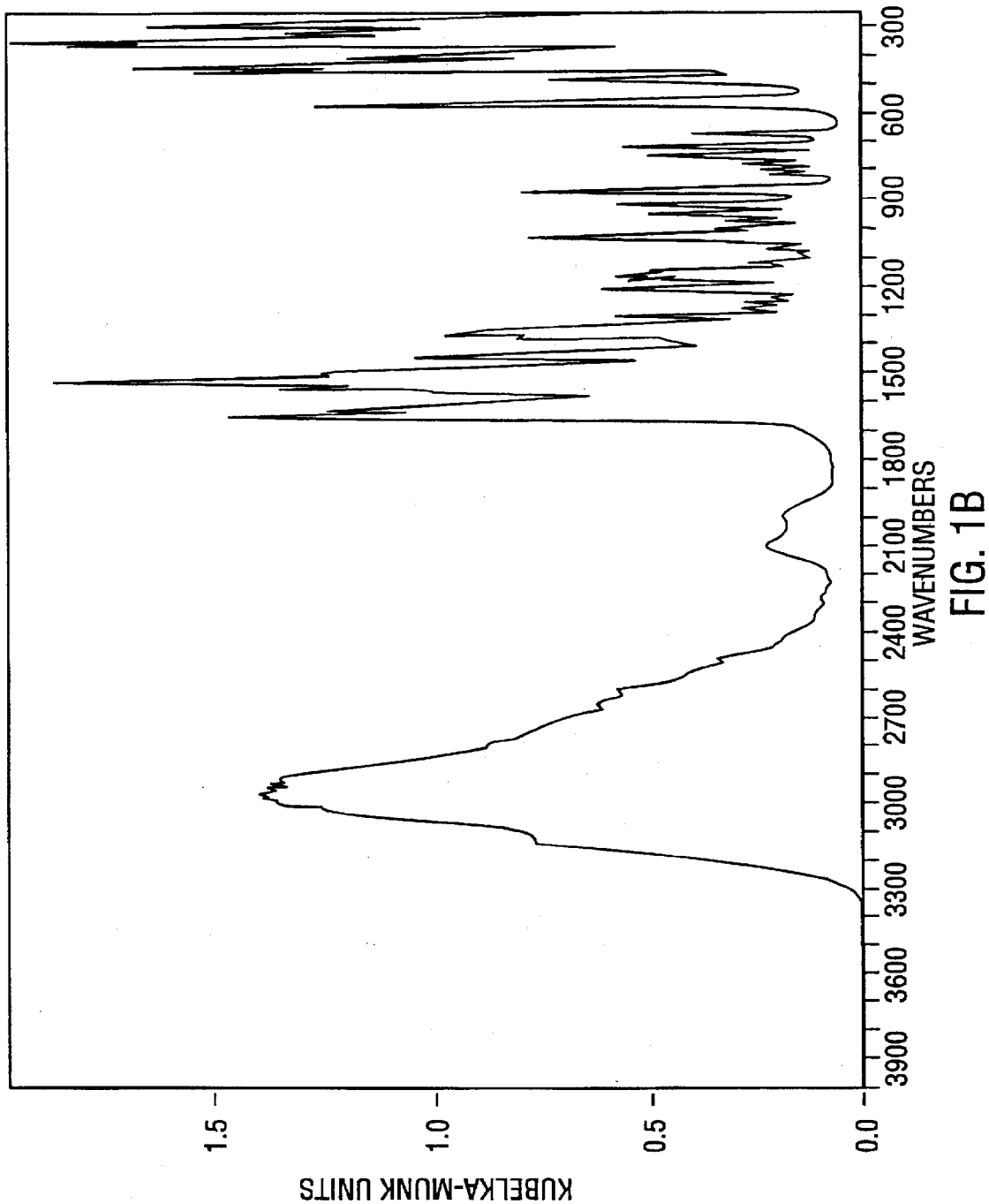
FIG. 1B is a control infrared spectrum of L-lysine.HCl substrate (see Example 3).
Figure 1C:
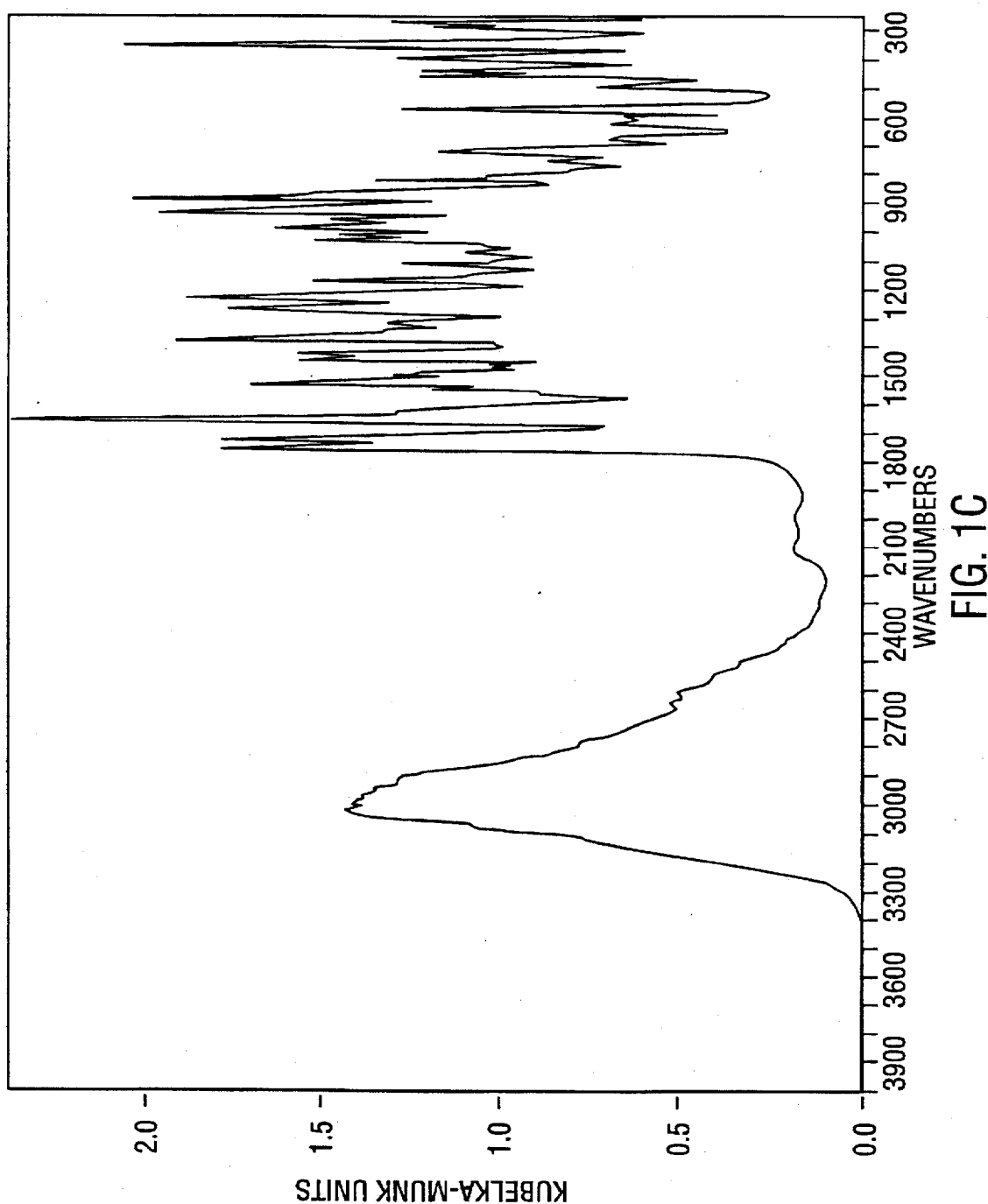
FIG. 1C is a control infrared spectrum of a physical mixture of these DTPA and L-lysine.HCl substrates without any chemical covalent linkage of the two substrates (see Example 3).

The many innovative teachings of the present invention will be described with particular reference to the presently preferred embodiments, wherein these innovative teachings are advantageously applied to the particular issues of in vivo T1-Type MRI image contrast enhancement by site-selective localization and sustained site retention of paramagnetic metal chelates according to optimal spatial and kinetic profiles at the site, while simultaneously enhancing clearance and minimizing toxicity of the non-localized dose fraction. However, it should be understood that this principal embodiment is only one example of the many advantageous uses of the innovative teachings herein. For example, the various types of innovative compositions and methods disclosed herein can alternatively be used to selectively localize and enhance clearance of radionuclide imaging agents, X-ray contrast agents, ultrasound-acoustic image enhancing agents and a wide spectrum of therapeutic agents which are based on site delivery of metal chelates and in situ chelation of endogenous body metals. Of special interest to the therapeutic agents and uses embodied herein, are actives and indications useful in oncotherapy, cardiovascular infarcts, restenosis, atherosclerosis, acute thrombosis, microvascular disease, inflammation, and any other tissue diseases which have as part of their development or progression, a vascular component amenable to modulation by the novel teachings, compositions and uses described herein. Hence, it will be obvious to those skilled in the art, that numerous additional compositions and uses are uniquely enabled by the present invention. The following examples are presented to illustrate preferred embodiments of the present invention, their uses in MRI contrast enhancement. These examples are purely illustrative, and do not in any way delimit the full scope of the present invention.

The present invention specifically describes the preparation and utilization of novel contrast agents for magnetic resonance imaging. These novel contrast agents consist of paramagnetic metal chelates, as distinguished from metal-atom complexes, wherein the presently disclosed chelates are bound to glycosaminoglycans (GAG). Binding of the metal complex to the GAG may take the form of, but is not limited to, electrostatic interactions (ion-paired), hydrogen-bonding, Van der Waals interactions, covalent linkages, or any combination of these interactions. Following parenteral administration of these metal complex-glycosaminoglycan formulations, the technology described herein utilizes a biocompatible carrier molecule to deliver an associated biologically active substance to sites of vascular injury.

The present invention provides substantially improved MRI image and spectral enhancement compositions and methods, whereby the capacity of MRI hardware systems to detect tumors, cardiovascular diseases, and other diseases with a vascular or endothelial adhesive component are greatly enhanced. These improvements are presently accomplished by introducing a chelated paramagnetic metal ion selectively into tissue sites of interest, inducing selective (local) modulation of T1-Type, paramagnetic relaxation of water protons or other diffusible nuclei present within the site which are susceptible to orientation by fixed and gradient magnetic fields and to pulsed re-orientation by radiofrequency fields of appropriate resonant frequencies, thereby giving rise to detectable modulations of induced magnetic resonance signals, in the forms of either image contrast enhancement or spectral enhancement.

Past disclosures (Ranney: U.S. Ser. No. 07/880,660, filed May 8, 1992, U.S. Ser. No. 07/863,595 filed Apr. 3, 1992, now U.S. Pat. No. 5,214,661 and U.S. Ser. No.07/642,033 filed Jan. 1, 1991] have dealt with the binding of magnetic agents which required: (a) magnetic potencies greater than that of the most potent single metal ion, gadolinium(III); (b) intramolecularly coupled, polyatomic metal-atom complexes stabilized by non-bridged ligands which have a stronger potential for chemical and physical instability than the stably, bridged-ligand chelated metal ions disclosed herein; and (c) divalent cationic charge on the "superparamagnetic" active for binding to anionic carriers, versus the presently disclosed requirement for only a monovalent cationic charge on paramagnetic metal chelator actives. It is understood, that for MRI uses, the metal chelator will also comprise an appropriate paramagnetic metal ion, for example, preferably iron(III) or gadolinium (III), however, for certain other diagnostic and therapeutic compositions and uses, the presently disclosed metal chelators may either comprise or avoid an appropriate metal ion. For the presently preferred MRI applications, basic metal chelators and metal chelators with electrophilic properties at formulation pH's are preferred, for example, ferrioxamine [Crumbliss, 1991], basic or amine derivatives of the polyaminocarboxylate chelator, diethylenetriaminepentaacetate (DTPA), and basic or amine derivatives of the macrocyclic chelator, 1,4,7,10-tetraazacyclododecane-N,N',N'',N'''-tetraacetate (DOTA) [Li et al. 1993; Brechbiel et al. 1986]. In certain instances and with certain potent carriers bound to these and related actives, site localization may be so pronounced that the inherent potency (in vitro paramagnetic R1) of the paramagnetic metal ion may not be crucial to obtaining optimal site-localized image contrast or spectral enhancement effects. Hence, the present invention discloses pronounced T1 image contrast effects for the basic metal chelate, ferrioxamine, which by virtue of chelated Fe(III) ions, has a potency, or R1 relaxivity, of about 1.6–1.8 [mmol.sec]-1. Alternatively, basic metal chelates of Gd(III) maybe expected under certain but not all in vivo conditions, to have a potentially greater relaxivity, due to its greater in vitro R1 of about 4.0–4.3 [mmol.sec]-1 when chelated by DTPA, and potentially moderately higher when chelated by DOTA [Geraldes et al. 1985]. Alternative metal ions may preferably include the divalent or trivalent cations, manganese, chromium and dysprosium; and less preferably, those ions of copper, nickel, erbium, europium, and holmium.

Preferred chelators of the present invention include those with a formation constant of at least about $10^{14}$ for strongly paramagnetic metal ions disclosed above, and including a basic or cationic group. These chelators preferably include ferrioxamine, basic or amine derivatives of DOTA, DTPA, porphines, porphyrins, sapphyrins or texaphyrins, which can preferably chelate Fe(III) and most preferably chelate Gd(III), as well as bind by principally paired-ion (electrostatic) means to the acidic groups of acidic carriers. For example, certain texaphyrins have an expanded macrocyclic ring which may, in certain instances, stably chelate Gd(III) [Sessler et al. '065; Sessler et al. '720; Sessler et al.

'498, incorporated by reference herein]. Whereas texaphyrins and sapphyrins are not exemplified in the present invention, it will be obvious to those skilled in the art, from the references cited just above, and from the presently disclosed and exemplified Fe(III) chelator, 5,10,15,20-Tetrakis(1-methyl-4-pyridyl)-21-23-porphine, that the related texaphyrins and sapphyrins and their basic, cationic and amine derivatives, as well as the presently disclosed porphine derivative and its analogues and basic, cationic and amine derivatives, would be included under the disclosures and teachings of the present invention, and may be used in combination with the presently disclosed acidic carriers. There are hybrid considerations of, among others: (a) paramagnetic potency of the metal chelate; (b) binding stability to the acidic carrier; and (c) formulation compatibility; and (d) biocompatibility and clearance in vivo. Hydrophilic chelators and carriers are usually, but not always preferred, due to their typically favorable formulation properties (absence of aggregation), biodistribution properties (absence of generalized binding to hydrophobic plasma and cell-membrane constituents during the process of localization); and clearance plus toxicity advantages. Alternative chelators may include the hydroxamates, ferrichrome, enterobactin, ferrimycobactin, ferrichrysin, and their basic or amine derivatives, all derivatives being defined as subsumed under the parent chelators listed above.

Preferred carriers include monomeric, oligomeric and polymeric substances which contain or comprise anionic or acidic groups defined at the pH's used for formulation. These typically contain or comprise groups of carboxylate, and more preferably, the even more strongly acidic groups of phosphate, and most preferably, sulfate. Preferred carriers include, but are not limited to an acidic saccharide, oligosaccharide, polysaccharide, glycosaminoglycan or sulfatoid, typically of bacterial or semi-synthetic origin, or derivatives or modifications or fragments of the preceding substances, all defined herein as being subsumed under the names of the parent substances and categories. Hence, preferred carriers include the following: heparin, desulfated heparin, glycine-conjugated heparin, heparin sulfate, dermatan sulfate, chondroitin sulfate, pentosan polysulfate, and sulfated sucrose, including sucrose octasulfate, and any derivative, modification or modified form thereof. Less preferably for typical MRI formulations and uses, are include the carriers of sulfated cyclodextrin, dextran sulfate and hyaluronic acid, although any of these may be particularly suitable for certain specific diagnostic or therapeutic formulations and uses.

In all cases reported and tested, non-covalent binding of the basic amine chelator to the acidic carrier gives payloads of active agent which are markedly higher than those afforded by covalent conjugation. For example, and preferably, ferrioxamine and Gd(III) DTPA-lysine are bound to their acidic glycosaminoglycan carriers at weight ratios of ≧70%. Alternative covalent active-carrier conjugates may be preferred in certain instances, and preferred examples thereof are shown for MRI applications.

Specific embodiments of the present invention which have been tested in vivo, include, but are not limited to the presently exemplified preferred embodiments of: (a) deferoxamine, (b) ferrioxamine and (c) Gd(III):DTPA-lysine basic metal chelates bound by most preferably non-covalent means, and also preferably by covalent means, as exemplified below, to acidic glycosaminoglycans, including preferably, dermatan sulfate, chondroitin sulfate, heparan sulfate, and heparin, which include by definition, any derivative or modification thereof, including oversulfation and modification undertaken to reduce anticoagulant activities or provide improved site binding, enhanced clearance or other desired formulation or in vivo properties. Alternative preferred Agents obvious from the present disclosures, to those skilled in the art, may induce arginine and histidine basic derivatives of DTPA and DOTA, and also of the various texaphyrins, sapphyrins, porphines, porphyrins, EHPG, and by definition, most preferably for MRI applications, comprising their Gd(III) and Fe(III) metal-ions, an also preferably comprising their alternative paramagnetic metal ion chelates, as disclosed above.

The present invention describes the preparation and utilization of a novel MRI contrast agent for enhancement of solid tumors and cardiovascular infarcts. The contrast agents consist of cationic or basic paramagnetic metal complexes in association with strongly acidic, including polysulfated carriers, and including preferably glycosaminoglycans. It would be obvious to those skilled in the art that any acidic glycosaminoglycan can be used. Of the paired-ion systems described below, most notably are those consisting of ferrioxamine with glycosaminoglycans and DTPA-lysine with glycosaminoglycans.

It is envisioned that alternative diagnostic and therapeutic compositions and applications may be carried out using compositions substantially similar to those disclosed above. For example, alternative metal ions may be chelated for purposes of metal-ion exchange at the site. Hence, the present formulations may contain or comprise metal ions of manganese, aluminum, germanium, zinc, cobalt, calcium, platinum, or others. Alternatively, for purposes of radiation and radionuclide therapy, such compositions may contain or comprise metal ions of boron, cobalt, rubidium, yttrium, technetium, ruthenium, rhenium, indium, iridium, thallium, samarium or others. Specifically, and in some cases preferably, $^{59}$Fe and $^{67}$Ga [Hashimoto et al. 1983; Janoki et al. 1983] may be substituted as radionuclide forms of the non-radioactive metal ions, for purposes of nuclear medical imaging of tumors, thrombi, and other biomedical imaging purposes.

The preceding discussion is presented to specify major aspects of the invention and their use in in vivo diagnostic and therapeutic applications, however, to those skilled in the art many additional and related compositions and methods of use will be obvious from this preceding discussion and are encompassed by the present invention.

TABLE 1

Advantages of Metal Ion Chelator and Anionic, Hydrophilic Carrier

| Technology | Selective MRI Agent | Antibodies | PEG | Liposomes |
| --- | --- | --- | --- | --- |
| Property | | | | |
| Drug Payload | High 77.5% | Very Low 5% | Low 10–30% | Low 15–20% |
| Localization In Tissue Sites | Yes | Very Low | No | No |
| Selectivity | Broad Immune (CHO-lectin) | Narrow Immune (Ab-antigen) | None | None |
| Time to Target | Very Rapid (several mins) | Slow (several hrs) | Slow (many hrs) | Very Slow (hrs–days) |
| Time to Clear Plasma & Body | Rapid | Very Slow | Very Slow | Extremely Slow (RES) |

TABLE 1-continued

Advantages of Metal Ion Chelator and Anionic, Hydrophilic Carrier

| Technology | Selective MRI Agent | Antibodies | PEG | Liposomes |
|---|---|---|---|---|
| Applications | Broad (Tissue Sites) | Narrow (Intravascular) | Narrow (Enzymes) | Narrow (RES) |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Deferoxamine Free Base and Use in Formulation of Ferrioxamine

The free base of deferoxamine is used in certain instances, in order to minimize the residual salt content present in final formulations which utilize deferoxamine as a basic metal chelator. In these instances, deferoxamine is precipitated out of aqueous salt solutions by the addition of 2 N $KHCO_3$, as previously reported [Ramirez et al. (1973), incorporated by reference herein]. A saturated solution of deferoxamine (320 mg/mL at 25° C.) is prepared by dissolving 4.0 g of deferoxamine mesylate salt in 12.5 mL of pharmaceutical-grade water. The solution is cooled to 4° C. in an ice bath and 2.5 mL of 2.0N $KHCO_3$ added. The glass container is scratched with a stainless steel spatula to initiate precipitation. The precipitate is collected by centrifugation, washed repeatedly with ice cold water, and filtered. The crude deferoxamine free base is purified by sequential recrystallization from hot methanol. The resulting pure deferoxamine free base is dried under a stream of nitrogen. The infrared spectrum of the deferoxamine as prepared is consistent with that referenced above.

Ferrioxamine is formulated from the deferoxamine free base by addition of ferric chloride at stoichiometric molar ratios of Fe(III) to deferoxamine free base. This results in chelated iron and minimizes residual mesylate and chloride ions.

EXAMPLE 2

Preparation of Ferrioxamine-Iron (III) Chelate

Batch quantities of the Fe(III) chelate of deferoxamine are prepared as follows. Deferoxamine mesylate (methanesulfonate) (Ciba-Geigy Limited, Basel, Switzerland), 390 g, is dissolved in pharmaceutical-grade water. Alternatively, the chloride salt of deferoxamine may be used. A highly purified slurry of ferric iron in the form of Fe(O)OH (13.44% w/v of Fe(O)OH particles, Noah Technologies Corporation, San Antonio, Tex.), 372.9 g is suspended in 1899 mL of water and added to the deferoxamine with constant stirring. The resulting suspension is heated to 60° C. for between 1 and 24 hours and the pH adjusted periodically to between 6.5 and 7.9 by addition of 0.10N NaOH. Formation the ferrioxamine complex is evidenced by development of an intense deep reddish-brown color to the solution. Stoichiometric chelation of Fe(III) with deferoxamine is confirmed by in-process UV-Visible absorbance spectroscopy at 430 nm, against stoichiometrically chelated ferrioxamine standards. The batch solution is cooled to room temperature and centrifuged at 4500 rpm (≈2500 g) for 15 minutes to remove any unreacted or aggregated Fe(O)OH. This final batch volume is adjusted as desired, typically to a final volume of 2600 mL. Any remaining trace amounts of unreacted Fe(O)OH are removed and the solution also made aseptic, by passing the supernatant through a 0.22 μm Millipore GV-type filter in a Class 100 laminar flow hood. The resulting batch is stored at 4° C. in an autoclaved, sealed glass container until further use (see Examples below). The final concentration of ferrioxamine (DFe) is determined once again by UV-Visible absorbance spectrophotometry at 430 nm.

EXAMPLE 3

Preparation of the Basic Amine Chelator: Diethylenetriaminepentaacetate-Lysine (DTPA-Lys)

DTPA, 500 mg, is dissolved in 20 mL of pharmaceutical-grade water and heated to 60° C. L-Lysine hydrochloride powder, 931 mg, is added with constant stirring until dissolved. Alternatively, N-epsilon-t-BOC-L-lysine can be used to prevent reaction of the carbodiimide intermediate at the lysine epsilon amino group (see below), and when used, is dissolved in dimethylformamide:water (50:50, w/v). The solution pH is adjusted to 4.75 by addition of 0.1N HCl. The water-soluble carbodiimide, 1-ethyl-3-(3-dimethylaminopropyl)carbodiimide HCl (EDC), 732.5 g, is dissolved in 2 mL water and its pH also adjusted as above. This EDC solution is added dropwise to the DTPA+lysine solution mixture (above) over 1 hour at 22° C. with constant stirring and periodic adjustment of pH to 4.75, and the reaction allowed to proceed to completion over 2 more hours. When N-epsilon-t-BOC-L-lysine is used (see above), the N-epsilon-t-BOC group is hydrolyzed at this step, by acidification with hydrochloric acid to a pH of between 1.0 and 2.0, and stirring for 30–60 min. The pH is readjusted to 4.75 as needed, and the reaction solution is concentrated down to 5 mL by rotary evaporation at 60° C., and the DTPA-lysine (DTPA-Lys) derivative is precipitated by addition of 3 volumes of ethanol. Note: under these conditions, the ethanol:water ratio used, maintains the solubility of all individual substrates (above). The resulting precipitate is harvested by centrifugation at 2,500×g, washed with ethanol, re-centrifuged, and dried over a stream of dry nitrogen. Covalent conjugation of lysine to DTPA is confirmed by infrared (IR) spectroscopy. The resulting reaction product has a faint yellow color.

EXAMPLE 4

Preparation of the Gadolinium(III) Metal Chelate of DTPA-Lys: gadolinium:DTPA-Lys [Gd(III):DTPA-Lys]

The gadolinium(III) chelate of DTPA-Lys, namely Gd(III):DTPA-Lys, is prepared by dissolving a known quantity of DTPA-Lys in water and adding a stock solution of gadolinium chloride, prepared at 0.1–1.0M, as needed, until a stoichiometric quantity of Gd(III) has been added. The pH is adjusted to 7.0 by addition of 1.0N NaOH. Alternatively, gadolinium oxide can be added and the reaction mixture stirred for 24 hours. In the case of gadolinium oxide, neutralization with 1.0N NaOH is not needed. Each batch of Lys-DTPA conjugate is pre-titrated and the final chelation product checked for stoichiometric addition of Gd(III), using a standard xylenol orange titration method [Lyle et al. (1963)], and further confirmed by quantitative ICP atomic absorption spectroscopy for gadolinium. The resulting Gd(III):DTPA-Lys is precipitated by addition of ethanol (3 volumes per volume of water), and the precipitate collected by centrifugation. This precipitate is rewashed with ethanol and centrifuged (as above), washed with acetone plus centrifuged, and the collected precipitate dried over a stream of dry nitrogen. The resulting product continues to have the same faint yellow color as noted in Example 3.

EXAMPLE 5

Preparation of Paired-ion Agents of Ferrioxamine Bound to Dermatan Sulfate Carriers; and Ferrioxamine to Depolymerized Dermatan Sulfate Carrier Ferrioxamine:dermatan sulfate paired-ion agents are prepared by mixing appropriate ratios of the water solutions of ferrioxamine (see Example 2, above) with either: (a) dermatan sulfate of modal MW between approximately 5,000 daltons and 45,000 daltons (Opocrin, S.p.A., Modena, Italy; and Scientific Protein Laboratories, Waunake, Wis.); or (b) depolymerized dermatan sulfate of modal MW between approximately 2,000 daltons and 5,000 daltons (Opocrin S.p.A., Modena, Italy). A range of ratios of ferrioxamine to dermatan sulfate are prepared between a low of 1:99 (wt %) of ferrioxamine:dermatan sulfate or depolymerized dermatan sulfate; and a high of 30:70 (wt %) of ferrioxamine: dermatan sulfate or depolymerized dermatan sulfate). Using 0.1 to 1.0N NaOH, the pH of the mixture is adjusted to between 5.5 and 8, the mixture is stirred continuously for 0.5 to 72 hours and the pH re-adjusted between 5.5 and 8, and typically to 7.5. This ferrioxamine:dermatan mixture is passed through a 0.22 µm filter to remove any residual insoluble iron oxides and hydroxides, and to render the liquid agent aseptic. The aseptic agent is stored either as a liquid at 4° C., or as a lyophilized powder (see below). Further processing is carried out on the liquid, by filling into glass vials and autoclaving at 120° C. for 15 minutes. Alternatively, further processing is carried out on the liquid by filling into glass vials, freezing at −50° C., and lyophilization to give an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and dermatan sulfate are measured and vial quantities confirmed by standard reverse-phase HPLC and macromolecular size exclusion HPLC methods, respectively.

Multiple batches of Ferrioxamine:Dermatan Sulfate Agent have been prepared. In vitro test results for a representative batch are as follows: ferrioxamine:dermatan sulfate ratio: 77.5:22.5 (w/w); solubility of agent, 550 mg/mL; water:octanol partition, 17,600 (±2,750):1; concentration of ferrioxamine, 0.166 mmol/mL; concentration of dermatan sulfate, 32 mg/mL; molecular weight of dermatan sulfate, MN=18,000 daltons; sulfate/carboxylate ratio of dermatan sulfate, 1.0±0.15; ferrioxamine and dermatan purities, nominal ±10%; pH, 6.5–7.9; viscosity, 3.8–4.2 centipoise; osmolality, 475–525 mOsm/Kg; R1, 1.5–1.8 [mmol.sec]-1; oversized particles, within USP guidelines for small-volume parenterals; Anticoagulant activity, less than 4.5 U.S.P. Units/mg (modified USP XXII assay); binding of ferrioxamine active to dermatan carrier, at least 92% retained (dialysis for 3 hours against 200 volumes, 500 daltons molecular weight cutoff).

In vitro stability of Ferrioxamine:Dermatan Sulfate Agent under accelerated conditions, indicate the following. (a) The liquid form is stable, by the preceding physicochemical and HPLC parameters for longer than 6 months at 4° C., 22° C. and 40° C.; is slightly unstable at 2 to 6 months at 60° C., and degrades significantly within 1 to 3 days at 80° C. (b) The liquid form can be autoclaved as above, with less than 3% degradation of ferrioxamine. (c) The lyophilized form is stable with respect to all parameters (above), including oversized particles; and is projected to be stable over storage periods of multiple years.

EXAMPLE 6

Preparation of Paired-ion Agents of Ferrioxamine Bound to Heparin

Ferrioxamine:dermatan sulfate paired-ion agents are prepared by mixing appropriate ratios of water solutions of ferrioxamine (as in Example 5, above) with (a) beef lung heparin of modal MW between approximately 8,000 daltons; and (b) porcine heparin of modal MW between approximately 10,000 daltons and 20,000 daltons. A range of ratios of ferrioxamine to heparin or heparin fragment are prepared between a low of 1:99 (wt/wt) of ferrioxamine:heparin or heparin fragment; and a high of 30:70 (wt of ferrioxamine:fragment. Using 0.1 to 1.0N NaOH, the pH of the mixture is adjusted to between 5.5 and 8, the mixture is stirred continuously for 0.5 to 72 hours and the pH re-adjusted between 5.5 and 8. This ferrioxamine:heparin mixture is passed through a 0.22 µm filter to remove any residual insoluble iron oxides-hydroxides and render the liquid agent aseptic. The aseptic agent is stored at 4° C. As indicated, further processing is carried out by filling aseptic liquid in glass vials, followed by freezing and lyophilizing, to render the agent as an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and heparin are measured and vial quantities confirmed by standard reverse-phase HPLC and macromolecular size exclusion HPLC methods, respectively.

EXAMPLE 7

Preparation of Non-anticoagulant Heparin Carrier By Glycine Derivatization

The anticoagulant activity of heparin can be reduced to almost negligible activity by derivatizing its carboxylate groups with glycine residues as reported [Danishefsky et al. (1971); Danishefsky et al. (1972)]. This non-anticoagulant heparin (Nac-heparin) can then be utilized as a modified glycosaminoglycan carrier. According to one present method of glycine conjugation, 0.75 g of heparin is weighed into a 100 mL beaker and dissolved in 25 mL of pharmaceutical-grade water. Glycine, 0.75 g, is added and the pH of the resulting solution adjusted to 4.75 with 0.10N HCl. 1-ethyl-3-(3-dimethylaminopropyl)carbodiimide HCl (EDC), 0.75 g, is weighed into a separate vial, solubilized by adding a minimum amount of water, and the pH adjusted to 4.75 with 0.10M HCl. Aliquots of the EDC solution are added to the mixture of glycine-glycosaminoglycan over a one hour period. After each addition of EDC, the pH is adjusted to maintained it at 4.75. After addition of all EDC, the reaction is allowed to proceed for an additional two hours with constant stirring and periodic pH adjustment. The glycine-heparin conjugate (Gly-HEP) is then precipitated by addition of 3 volumes of absolute ethanol. The precipitate is collected by centrifugation at 4500 rpm (≈2500×g) for 15 minutes; and washed three times with 20-mL aliquots of ethanol with re-centrifugation.

EXAMPLE 8

Preparation of Paired-ion Agents of Ferrioxamine Bound To Glycosaminoglycans, Modified and Derivatized Glycosaminoglycans of: heparan sulfate, non-anticoagulant heparin oversulfated dermatan sulfate chondroitin sulfate, oversulfated chondroitin sulfate and the bacterial Sulfatoid, pentosan polysulfate Ferrioxamine paired-ion agents are prepared with various glycosaminoglycan carriers by mixing appropriate ratios of water solutions of ferrioxamine (as in Example 5, above) with the following glycosaminoglycans: (a) heparan sulfate of MN=8,500 daltons; (b) non-anticoagulant heparin SPL, ++ of MN=10,500 daltons; (c) oversulfated dermatan sulfate of MN=19,000 daltons; (d) chondroitin sulfate of MN=23, 400 daltons; (e) oversulfated chondroitin sulfate of MN=14, 000 daltons; and (f) pentosan polysulfate of MN=2,000 daltons. The ratios of ferrioxamine to glycosaminoglycan and sulfatoid carriers are prepared to give a payload of [77.5:22.5% (w/w) of ferrioxamine to carrier] (adjusted) by a scaling factor of [(mEq sulfates/mg of carrier as above)/(mEq sulfates/mg of beef lung heparin*)]. Using 0.1 to 1.0N NaOH, the pH of the mixture is adjusted to between 5.5 and 8, the mixture is stirred continuously for 0.5 to 72 hours and the pH re-adjusted between 5.5 and 8. This ferrioxamine:heparin mixture is passed through a 0.22 μm filter to remove any residual insoluble iron oxides-hydroxides and render the liquid agent aseptic. The aseptic agent is stored at 4° C. As indicated, further processing is carried out by filling the aseptic liquid in glass vials, followed by freezing and lyophilizing, to render the agent as an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and heparin are measured and vial quantities confirmed by standard reverse-phase HPLC and macromolecular size exclusion HPLC methods, respectively.

* For beef lung heparin, mEq $SO_3^-$/g carrier=4.4.

Although not prepared in the present application, it is apparent that by combining the teaching of the present Example with those of previous disclosures 07/880,660, 07/803,595, and 07/642,033, ferrioxamine complexes can be similarly prepared with additional acidic saccharides, including sucrose octasulfate and sulfated cyclodextrins; with additional glycosaminoglycans, including keratan sulfate and hyaluronate; and with additional sulfatoids, including the bacterial sulfatoid, dextran sulfate.

EXAMPLE 9

Preparation of Paired-ion Agents of Gd(III):DTPA-Lys Bound to Dermatan Sulfate Carrier Gd(III):DTPA-Lys:Dermatan Sulfate paired-ion agents are prepared by mixing the water solutions of Gd(III):DTPA-Lys with dermatan sulfate of modal MW between approximately 5,000 daltons and 45,000 daltons (as in Example 5, above), and in particular, dermatan sulfate of MN=18,000 (Opocrin, S.p.A., Modena, Italy), to form a final solution ratio of 77:30% (w/w) of the Gd(III):DTPA-Lys active to the Dermatan Sulfate carrier. Several stable Agent variations of the resulting liquid have been prepared, wherein the concentration of Gd(III):DTPA-Lys ranges from 0.166 to 0.415 mmol/mL, and the respective concentration of dermatan sulfate ranges from 35 to 87.5 mg/ml.

EXAMPLE 10

Preparation of a Basic Iron-porphine Chelate; and Paired-ion Binding to Heparin

The soluble, tetra-basic porphine, 5,10,15,20-tetrakis(1-methyl-4-pyridyl)-21H-23-Hporphine, 40 mg as the tetra-p-tosylate salt, is refluxed with Fe(II) chloride, 30 mg, for 2 hours in 20 mL of dimethylformamide. Evidence of iron complexation is observed in the form of a red to dark green color. Solvent was removed by evaporation, the solid product dissolved in water. The pH is adjusted to 7.5 to insolubilize excess ferric iron, followed by filtration of the iron-porphine product. A 2 mg/mL solution of iron-porphine complex and ca. 100% product yield is confirmed by inductively coupled plasma atomic absorption. A comparable reaction in water gives ca. 70% yield.

This iron-porphine complex is added to beef lung heparin dissolved in water, ca. 8 Kd, at ratios ranging from 1:20 to 20:1 (iron-porphine:heparin). This resulted in clear solutions without precipitates. Binding of iron-porphine to heparin is nearly 100% as evaluated by dialysis against water for 16 hours, using bags with molecular weight cutoffs of 3.5 Kd and 12 Kd. Iron-porphine alone is nearly completely dialyzed. UV-Visible spectrophotometric titration indicates maximum binding occurs at a molar ratio of 18:1 (iron-porphine:heparin). Since the beef lung heparin used is known to have approximately 18 available strongly acidic (sulfate) groups per mole (and per heparin chain), these results indicate strong ionic interaction and stable (to dialysis) binding of the basic tetraamine porphine complex to the sulfate groups of heparin.

EXAMPLE 11

Preparation of a Basic Triethylenetetraamine-iron Chelate; and Paired-ion Binding to Heparin and Sucrose Octasulfate Soluble complexes of triethylenetetraamine and iron(III) are formed by dissolving 1.0 g of triethylenetetraamine.2HCl (Syprine™) (Merck, West Point, Pa.) in water and adding a 1:1 mole ratio of iron chloride under acidic conditions (pH=2) to give a clear yellow solution. Using 0.1N NaOH, the pH is adjusted to 6.8, giving a red solution indicative of iron complexation. This solution develops a feathery red precipitate, indicative of intermolecular aggregation of the iron-triethylenetetraamine complex.

(a) To this resulting aqueous dispersion of complex is added beef lung heparin, to give final complex-to-heparin ratios of between 95:5 and 5:95 (by weight). At a ratio of 65:35 (complex:heparin) and higher ratios of heparin, heparin completely solubilizes the complex. This apparent solubilization is indicative of paired-ion binding between triethylenetetraamine-iron and heparin.

(b) To the aqueous dispersion of triethylenetetraamine-iron complex is added sucrose octasulfate (SOS), to give final complex-to-SOS ratios of between 95:5 and 5:95 (by weight). At a ratio of 65:35 (complex:SOS) and higher ratios of SOS, SOS causes the dispersion to become very much finer, indicative of paired-ion binding between triethylenetetraamine-iron complex and SOS. The absence of complete clarification of this SOS paired-ion system relative to that with heparin (above), is due to the much higher density of sulfates on SOS relative to heparin, which confers substantially increased intermolecular hydrogen bonding on the SOS system.

Although not directly exemplified, it will be apparent that polyamines with the homologous series $C_xH_{x+y}N_{x-z}$, which also form stable complexes with Iron(III), can also be used in place of triethylenetetraamine-iron complex and SOS in the present invention.

Preparation of Covalent Conjugates of Deferoxamine Glycosaminoglycan Carriers Substrates with electrophilic amine groups may be covalently conjugated reagents to nucleophilic carboxylate groups of acidic carriers, acidic saccharides and acidic glycosaminoglycans as reported [Danishefsky et al. (1971); Danishefsky et al. (1972); Janoki et al. 1983); Axen (1974); Bartling et al. (1974); Lin et al. (1975)]. The coupling reagents described in these references activate carboxylate groups toward nucleophilic attack. The mechanism involves formation of an activated intermediate resulting from reaction of the coupling reagent with the carboxylate residues on the carrier. The intermediate undergoes nucleophilic attack, typically by an amine functional group. This results in formation of a stable covalent conjugate, typically via an amide bond between the active and the carrier. Examples 12, 13, and 14 (below) describe the synthesis of ferrioxamine-heparin covalent conjugates, wherein the ferrioxamine is covalently bound to heparin via three different coupling reagents.

EXAMPLE 12

Preparation of a Covalent Ferrioxamine-Heparin Conjugate by 1-ethyl-3-(3-dimethylaminopropyl) Carbodiimide (EDC) Linkage Aqueous ferrioxamine, 2.0 g, as prepared in Example 1, is adjusted to pH 4.75 by addition of 0.10M HCl. Beef-lung heparin (Hepar-Kabi-Pharmacia, Franklin, Ohio), 0.75 g, is dissolved 5.0 mL of pharmaceutical-grade water and added to the ferrioxamine with constant stirring. The pH of the resulting solution is readjusted to 4.75 with 0.10M HCl. The water-soluble carbodiimide, 1-ethyl-3-(3-dimethylaminopropyl) carbodiimide HCl (EDC), 2 g, is weighed into a scintillation vial, solubilized in a minimum amount of water, and the pH adjusted to 4.75 with 0.10M HCl. Aliquots of EDC solution are pipetted into the mixture of ferrioxamine-heparin over a one hour period. After each addition of EDC the 0.10M HCl is added to maintain the pH at 4.75. After addition of all EDC, the reaction is allowed to proceed for an additional two hours with constant stirring. The ferrioxamine-heparin conjugate is precipitated by addition of 3 volumes of absolute ethanol. This precipitate is collected by centrifugation at 4500 rpm (≈2500×g) for 15 minutes and washed three times with 20 mL aliquots of ethanol plus centrifugation. The complex is further purified by redissolving in water and reprecipitating with 3 volumes of ethanol plus centrifugation. The final product is collected and dried over nitrogen. Ferrioxamine derivatization of heparin is confirmed by UV-visible absorbance spectroscopy of the ferrioxamine chelate at 430 nm and heparin analysis by size-exclusion HPLC chromatography.

EXAMPLE 13

Preparation of a Covalent Ferrioxamine-Heparin Conjugate by N-Ethoxycarbonyl-2-ethoxy-1,2-dihydroquinoline (EEDQ) Linkage Beef-lung heparin (Hepar-Kabi-Pharmacia, Franklin, Ohio), 0.50 g, is weighed into a 3-necked 100 mL round bottom flask fitted with an inlet and outlet for $N_2$ purge. Anhydrous dimethylformamide (DMF), 20 mL, is added with constant stirring and the resulting suspension warmed to 50° C. under a constant flow of nitrogen. A 30 mole excess (≈463.7 mg) of N-ethoxycarbonyl-2-ethoxy-1,2-dihydroquinoline (EEDQ) is added and the resulting suspension stirred at 50° C. for 3 hours. The activated EEDQ-activated heparin is collected by centrifugation at 4500 rpm (≈2500×g) for 10 minutes. The pellet is washed repeatedly with anhydrous DMF and then 3 times with acetone. The activated intermediate is dried under a stream of nitrogen.

An aliquot of ferrioxamine solution containing 766.3 mg of the iron complex, as prepared in Example 1, is pipetted into a 50 mL beaker and diluted to 25 mL with anhydrous DMF. In a separate 50 mL beaker, a known amount of EEDQ-activated heparin is suspended in 50 mL of anhydrous DMF with constant stirring. The DMF solution of ferrioxamine is pipetted slowly into the EEDQ-heparin suspension over a 5 minute period. The resulting suspension is stirred continuously for 3 hours at 40° C. After cooling to room temperature, the final product is collected by centrifugation, washed three times with anhydrous DMF, washed three times with acetone, and dried under nitrogen. Confirmation of conjugate formation is performed as in Example 12.

EXAMPLE 14

Preparation of a Covalent Ferrioxamine-Heparin Conjugate by Carbonyldiimidazole (CDI) Linkage An activated intermediate of beef-lung heparin (Hepar-Kabi-Pharmacia, Franklin, Ohio) is prepared by weighing 3.0 g of heparin into a 50 mL round bottom flask and adding 25 mL of anhydrous dimethylformamide (DMF) with constant stirring. Carbonyldiimidazole (CDI), 608.1 mg, (10 mole excess relative to heparin) is weighed into a separate vial and dissolved in 20 mL of anhydrous DMF. The DMF solution of CDI is added to the DMF-heparin suspension and stirred at 30° C. for one hour. The CDI-activated heparin is collected by centrifugation, washed repeatedly with acetone to remove unreacted CDI and residual DMF, and dried under nitrogen.

The deferoxamine-heparin conjugate is prepared by weighing 1.0 g of the CDI-activated heparin into a 50 mL round bottom flask and suspending this in 25 mL of anhydrous DMF. Deferoxamine, 250 mg, prepared as in Example 1, is weighed into a separate round bottom flask and dissolved in 20 mL of anhydrous DMF. The deferoxamine free base solution is added slowly to the CDI-heparin suspension and stirred continuously for 16 hours at 75° C. The deferoxamine-heparin conjugate is collected by centrifugation at 4500 rpm (≈2500×g) for 15 minutes, washed repeatedly with anhydrous DMF, washed repeatedly with acetone, and dried under nitrogen. The resulting product is dissolved in water, and its concentration determined by UV-Visible spectroscopy. A stoichiometric quantity of aqueous $FeCl_3$ is added and the resulting solution adjusted gradually to pH 6.5 and stirred for 2 hours. This results in a deep brown-red product. This ferrioxamine-heparin conjugate is separated from any residual substrates and intermediates by dialysis through a 2,000 MW cutoff bag against 150 volumes of water. The retentate is collected and concentrated by rotary evaporation. Confirmation of derivatization is performed as in Examples 12 and 13.

EXAMPLE 15

Preparation of a Covalent Heparin-Diethylenetriaminepentaacetate Conjugate (DTPA-heparin)

DTPA-functionalized carriers are prepared in aqueous media from the reaction of diethylenetriaminepentaacetic dianhydride (cDTPAA; Calbiochem-Bhering Corp.) and a molecule containing a nucleophilic functional group. Beef-lung heparin (Hepar-Kabi-Pharmacia, Franklin, Ohio), 1.5 g, is dissolved in 75.0 mL of 0.05M HEPES buffer and the pH adjusted to 7.0 with 0.10M NaOH. cDTPAA, 4.5 g ($\approx$100 mole excess relative to heparin), is weighed out and divided into 20 equal (225 mg) aliquots. An aliquot of cDTPAA is added to the heparin solution every 3–5 minutes until all cDTPAA has been added. The pH of the solution is monitored continuously throughout cDTPAA addition and maintained at pH 7.0 with 0.10M NaOH. After addition of the last aliquot of cDTPAA, the solution is stirred for an additional 30 minutes. The DTPA-heparin solution is dialyzed through 1000 MW bags against 150 volumes to remove non-conjugated DTPA. The resulting conjugate is concentrated by nitrogen-evaporation at 37° C. and stored at 4° C.

EXAMPLE 16

Preparation of Gadolinium(III) and Iron(III) Chelates of DTPA-heparin Covalent Conjugate The DTPA-heparin conjugate of Example 15 is further prepared in the form of paramagnetic metal chelates of the DTPA group with gadolinium(III) or Fe(III), by pipetting the required volume of DTPA-heparin into a 125 mL Erlenmeyer flask, adding a 1.5-to-10 mole excess of the paramagnetic metal ion oxide, as $Gd_2O_3$ or Fe(O)OH, and stirring for 24 to 36 hours at 37° C. to obtain solubilization of the metal oxides sufficient for complete occupancy of the DTPA groups. The residual metal oxides are precipitated by centrifugation at 4500 rpm ($\approx$2500 g), and the product separated from unreacted metal oxides by filtration through a Millipore 0.22 μm GV-type filter, followed by dialysis against 150 volumes. The concentrations of chelated metal ion and heparin are determined by inductively coupled plasma (ICP) and size-exclusion HPLC, respectively. In the case of Gd(III), stoichiometric chelation is also confirmed by standard xylenol orange titration [Lyle et al. (1963)].

EXAMPLE 17

Toxicity Studies of Ferrioxamine:Dermatan Sulfate

Acute intravenous Toxicity Studies with 14-day recovery and necropsy are performed in male and female rats and male and female dogs. At standard i.v. injection rates of 0.075 mmol/Kg/min., significant signs generally occur only after 5–12.5 1 times the effective imaging dose of 0.155 mmol/Kg. The LD50 is much greater than 4.5 mmol/Kg and is limited by technical aspects of tail-vein infusion. At this rate, some rats can be infused with 10 mmol/Kg without untoward effects. At an artificially accelerated i.v. injection rate of 0.080 mmol/Kg, deaths in rats can be obtained, and the LD50 is between 2.5 and 3.0 mmol/Kg. Terminal necropsy reveals no abnormalities in any rats after i.v. injection of 2.2, 3.0 and 4.5 mmol/Kg (n=5 males and 6 females per dose level).

A pyramid acute i.v. toxicity study is performed in dogs at escalating doses of 0.5, 1.2 and 2.25 mmol/Kg and an infusion rate of 0.012 mmol/Kg/min in protocol studies. An acute symptom complex of hypotension can be obtained, which is minimal and reversible. No deaths occurred and terminal necropsy at 14 days revealed no abnormalities (n=2 males and 2 females, all administered each of the three dose levels, with a 72-hour rest interval).

EXAMPLE 18

Figure 2A:
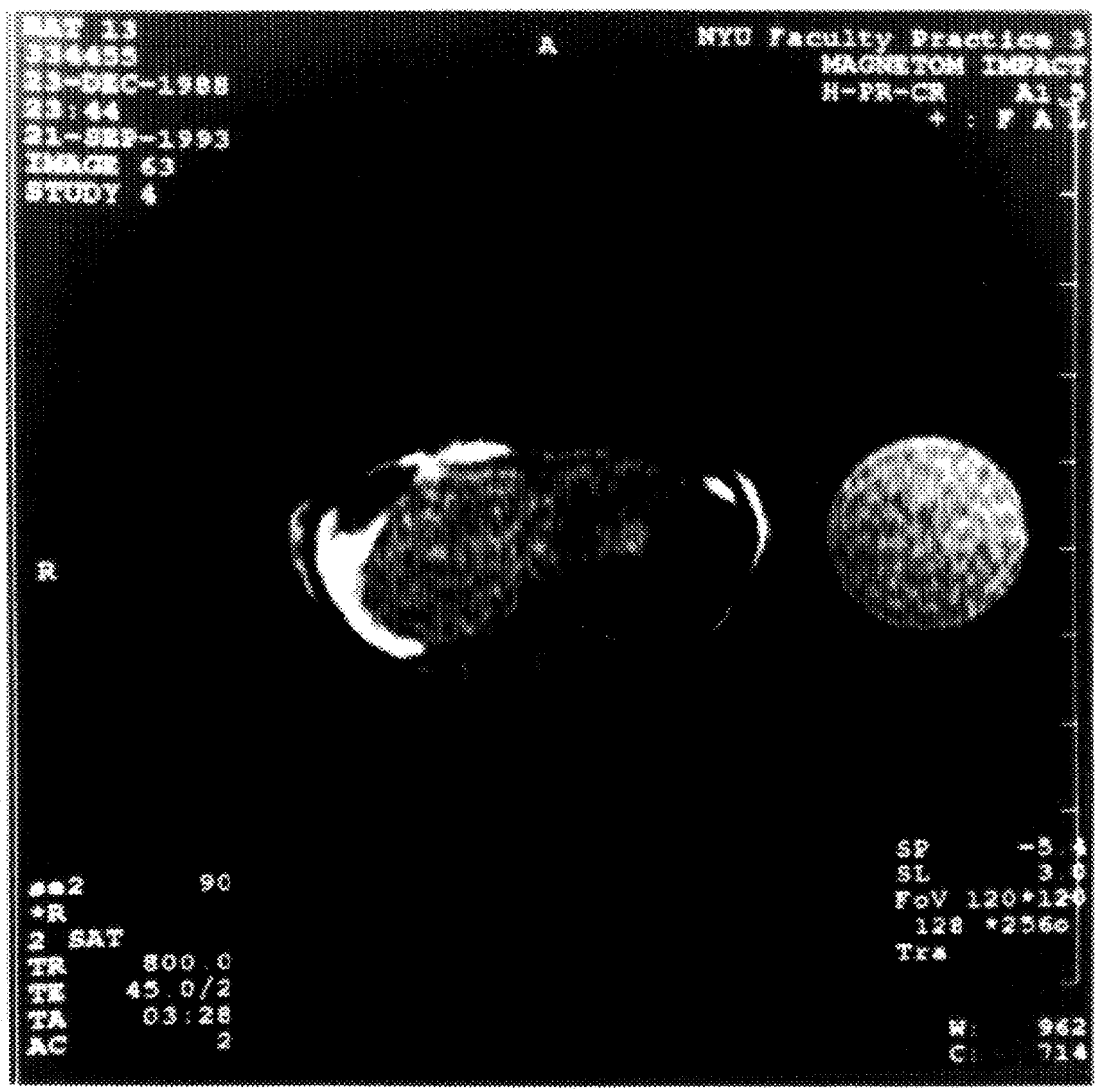
Figure 2B:
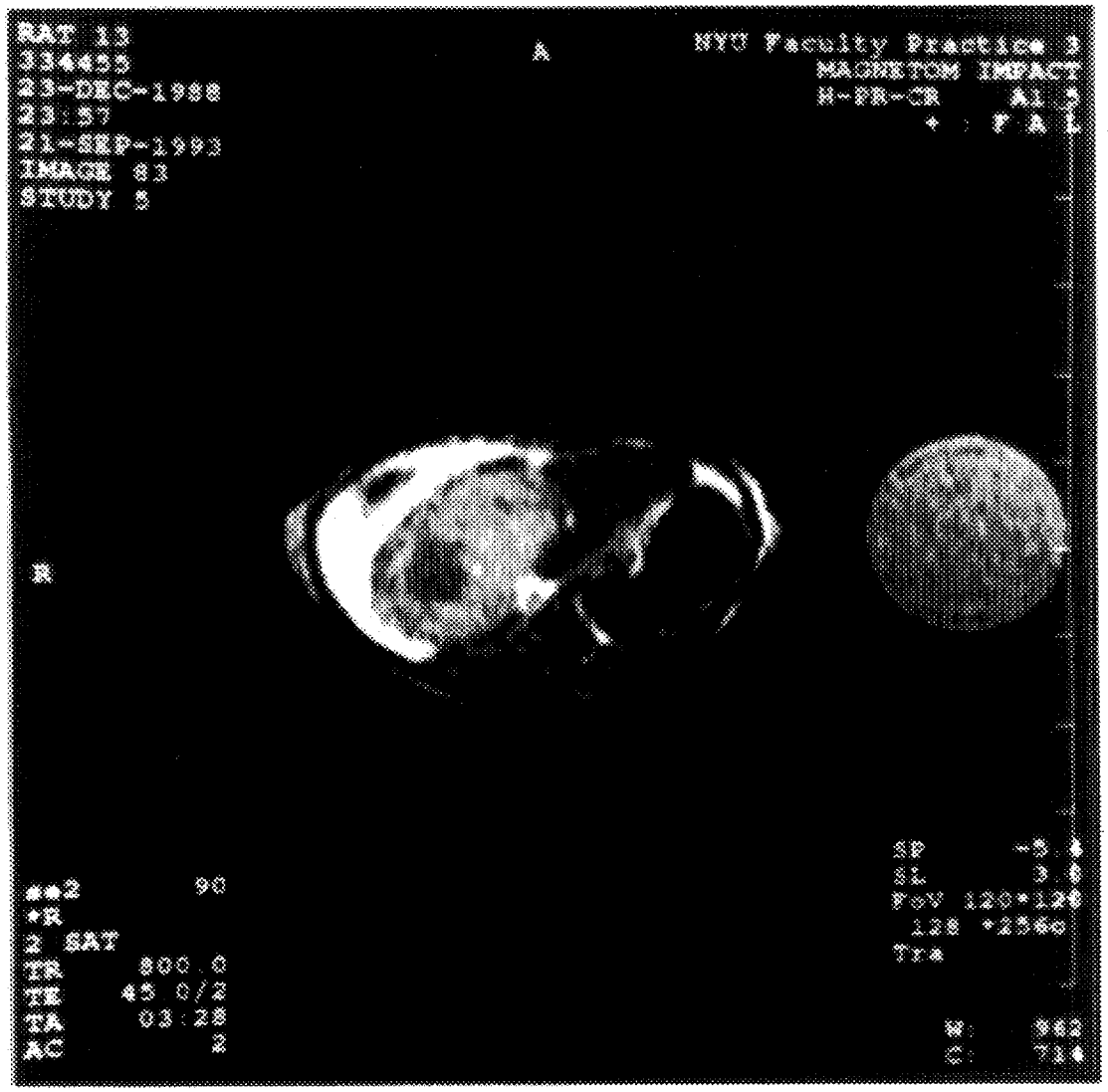
FIG. 2B Liver image at 7 min postinjection (MPI) of the Selective Paramagnetic Contrast Agent, Ferrioxamine:Dermatan Sulfate (0.155 mmol/Kg) i.v., showing marked contrast enhancement of tumor in right lobe of liver, very sharp tumor boundaries against surrounding liver, and discretely demarcated darker central region of tumor necrosis—allowing tumor perfusion and function to be spatially resolved and assessed within different, very small anatomical subregions.
Figure 3A:
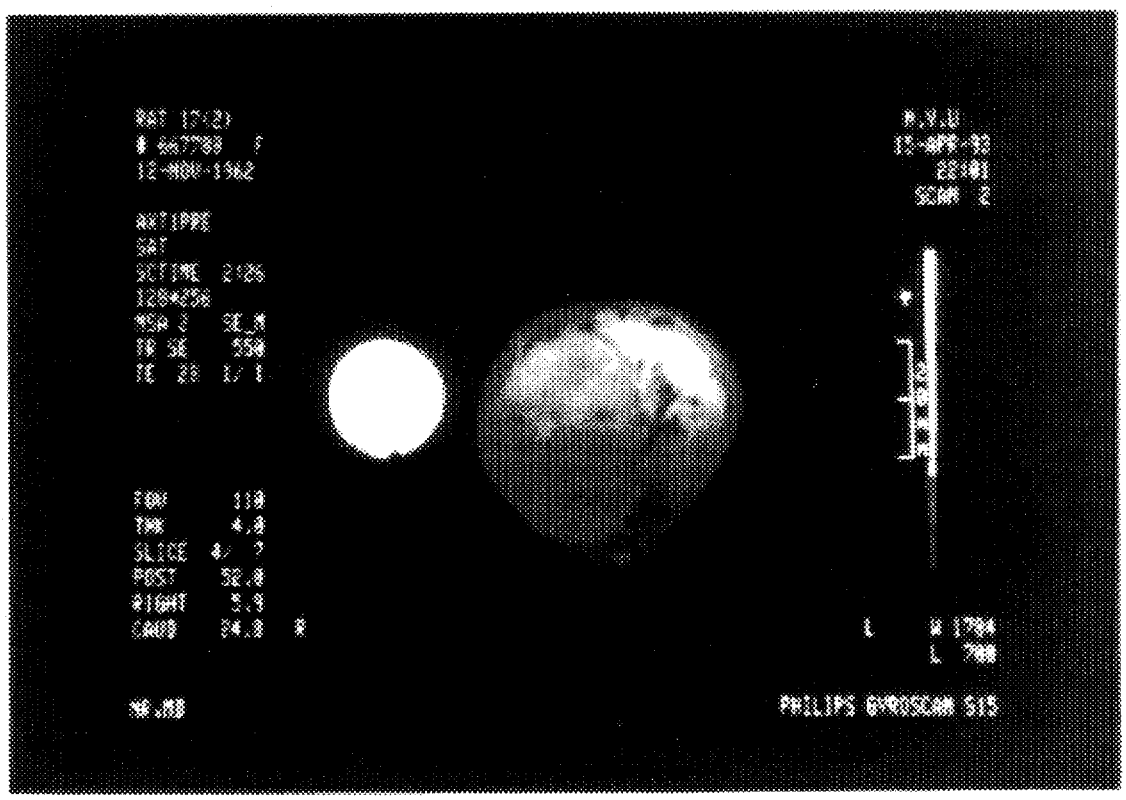
FIG. 3A Precontrast image of liver (tumor is present but not conspicuous).
Figure 3B:
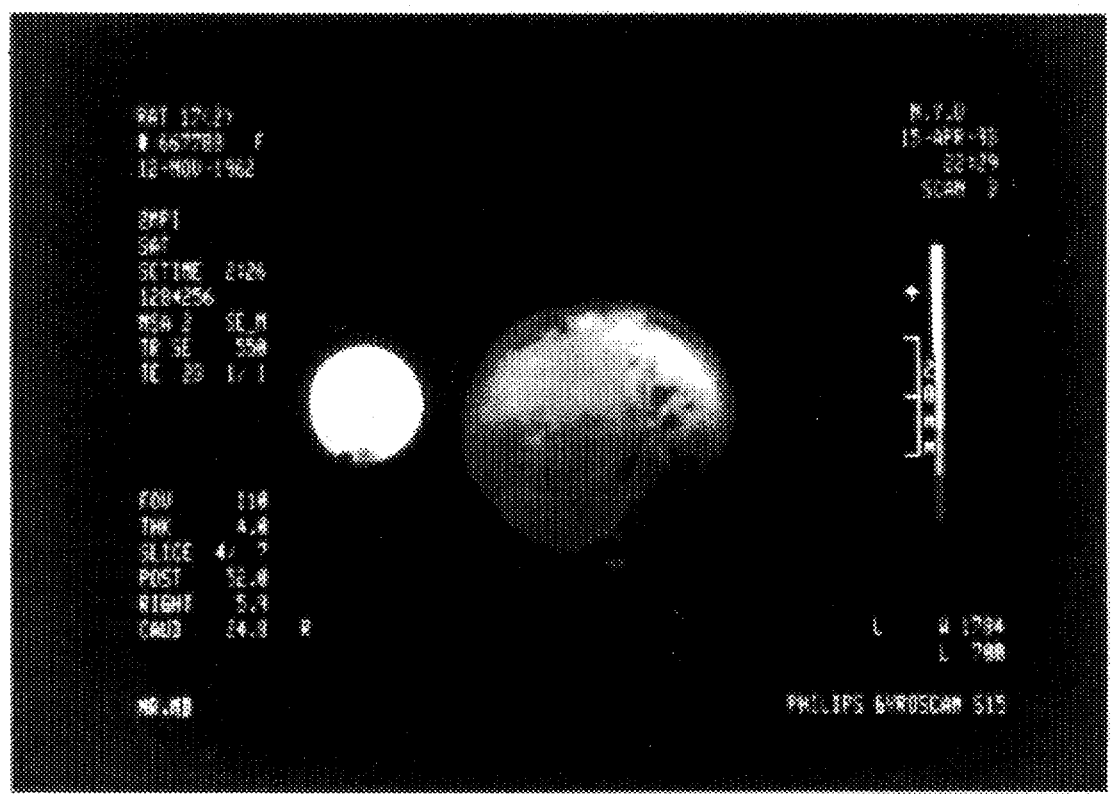
FIG. 3B Liver image at 7 MPI of Ferrioxamine Active Alone (without any Dermatan Sulfate Carrier). Note that acute contrast enhancement is only very slight or nonexistent. This differs markedly from the pronounced tumor enhancement seen in FIG. 2B; and it indicates that binding of the Ferrioxamine active by the Dermatan Sulfate carrier is a requirement for tumor-site localization and tumor uptake of Ferrioxamine active.
Figure 4A:
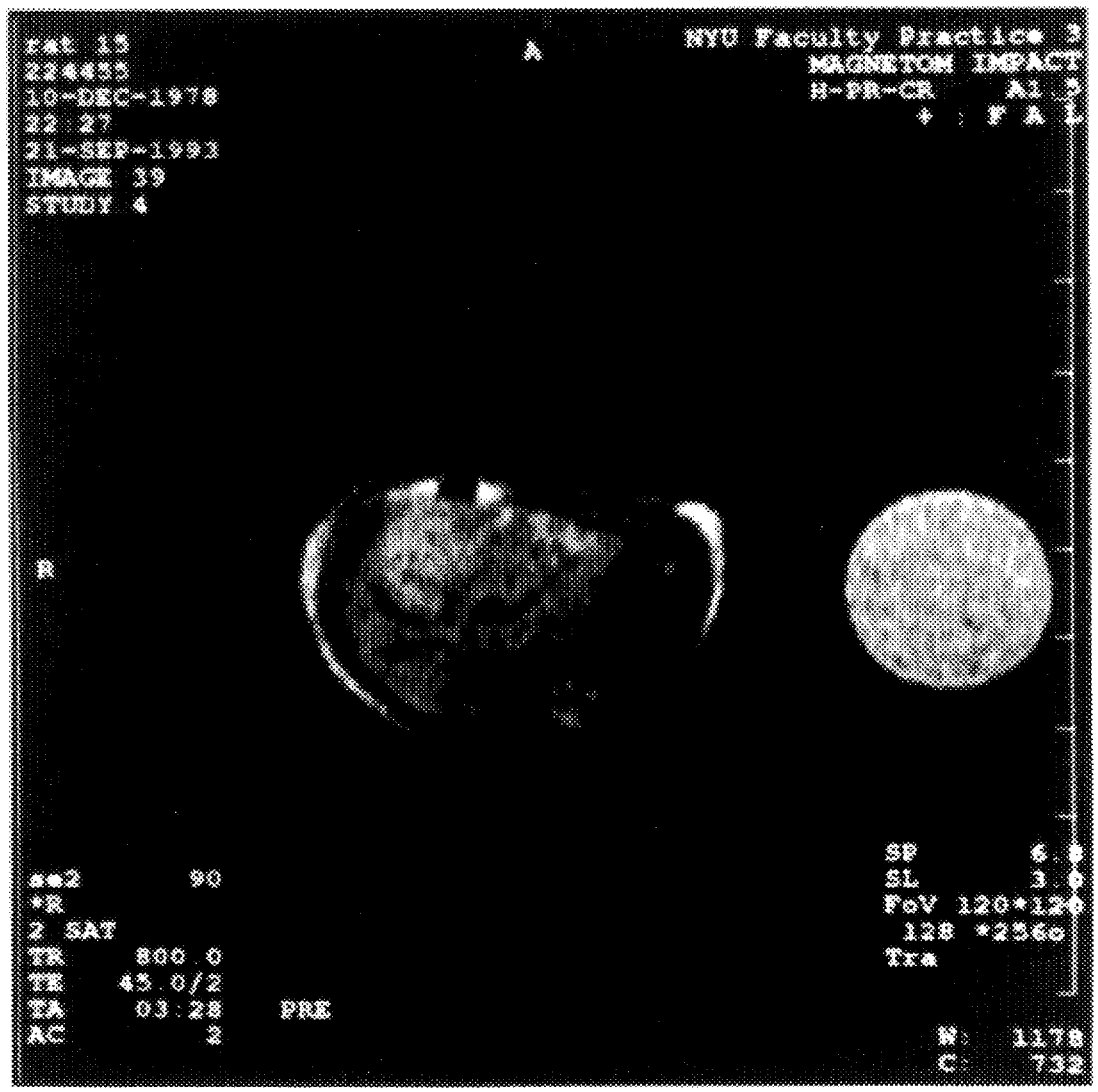
FIG. 4A Precontrast T1 image (TR/TE =800/45) of liver (breast tumor is present but not conspicuous).
Figure 4B:
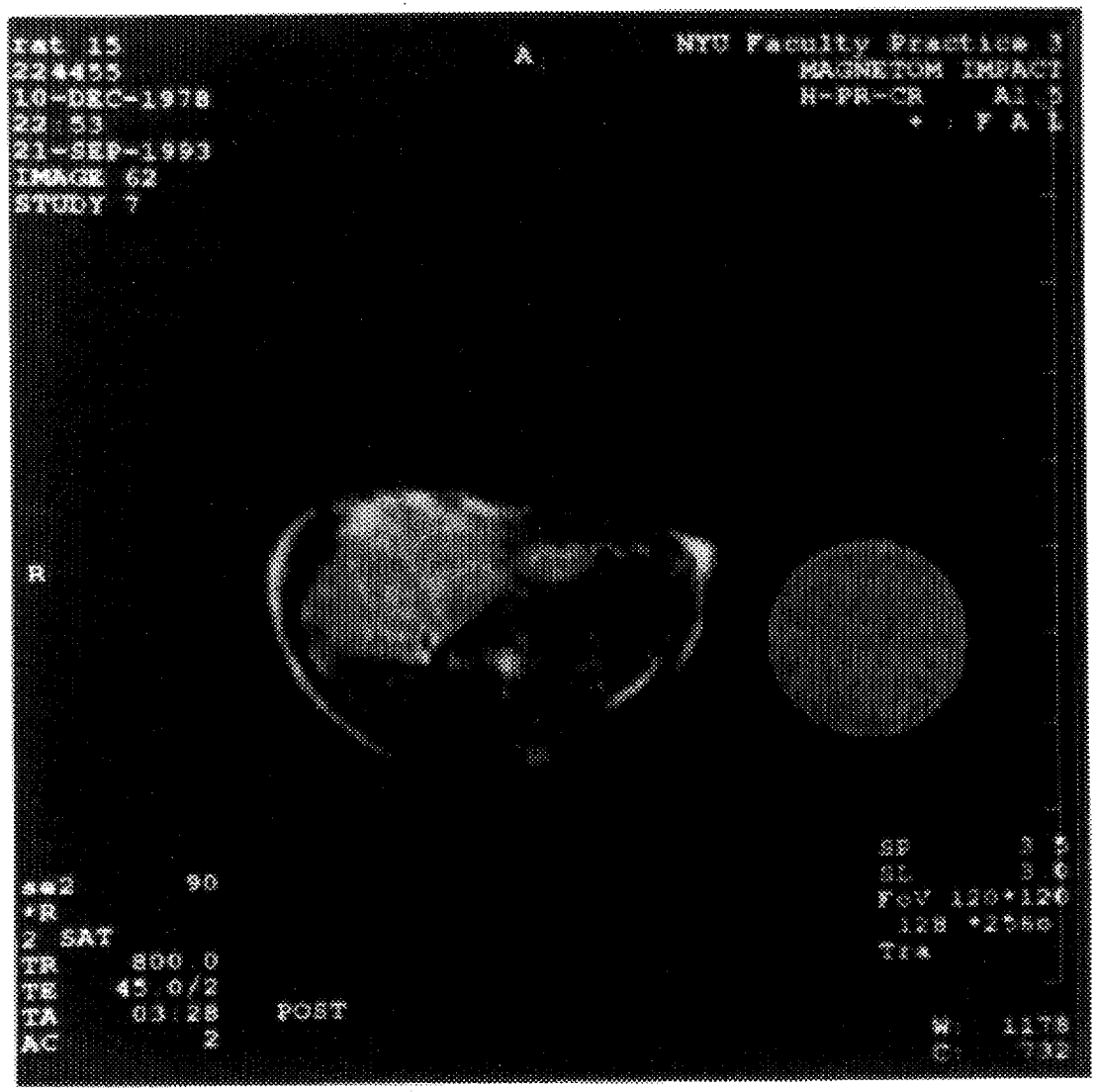
FIG. 4B Liver image at 21 MPI of Ferrioxamine:Dermatan Sulfate Selective MRI Contrast Agent. Note the marked enhancement of main tumor mass and distinct tumor borders. Also note the small, 2-mm, bright enhancement of tumor metastasis in left lobe of liver. This metastasis is completely non-visualized in the Precontrast T1 images.
Figure 4C:
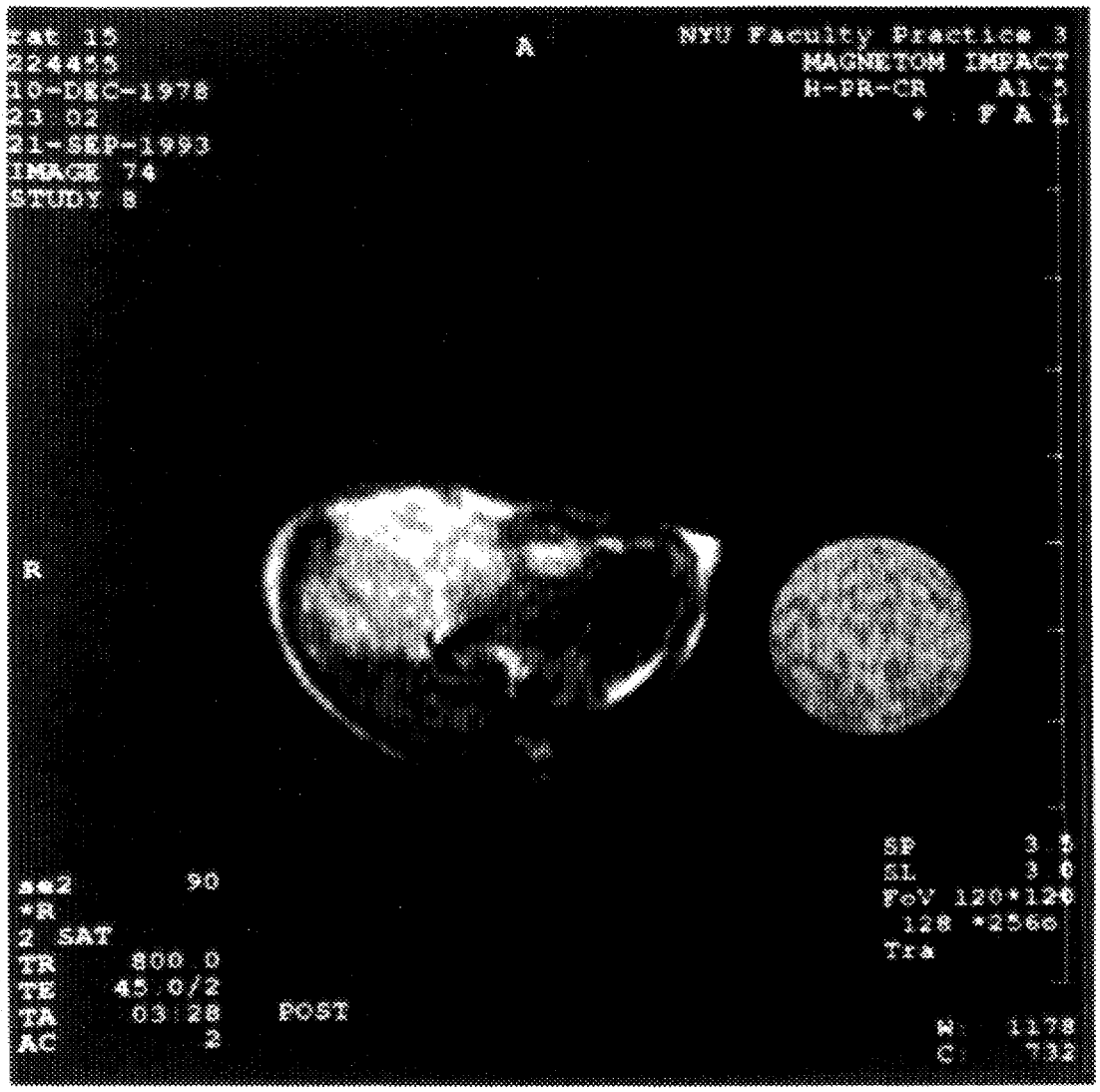
FIG. 4C Liver image at 30 MPI of Ferrioxamine:Dermatan Sulfate Selective MRI Contrast Agent. Note the sustained enhancement of main tumor and metastasis.
Figure 4D:
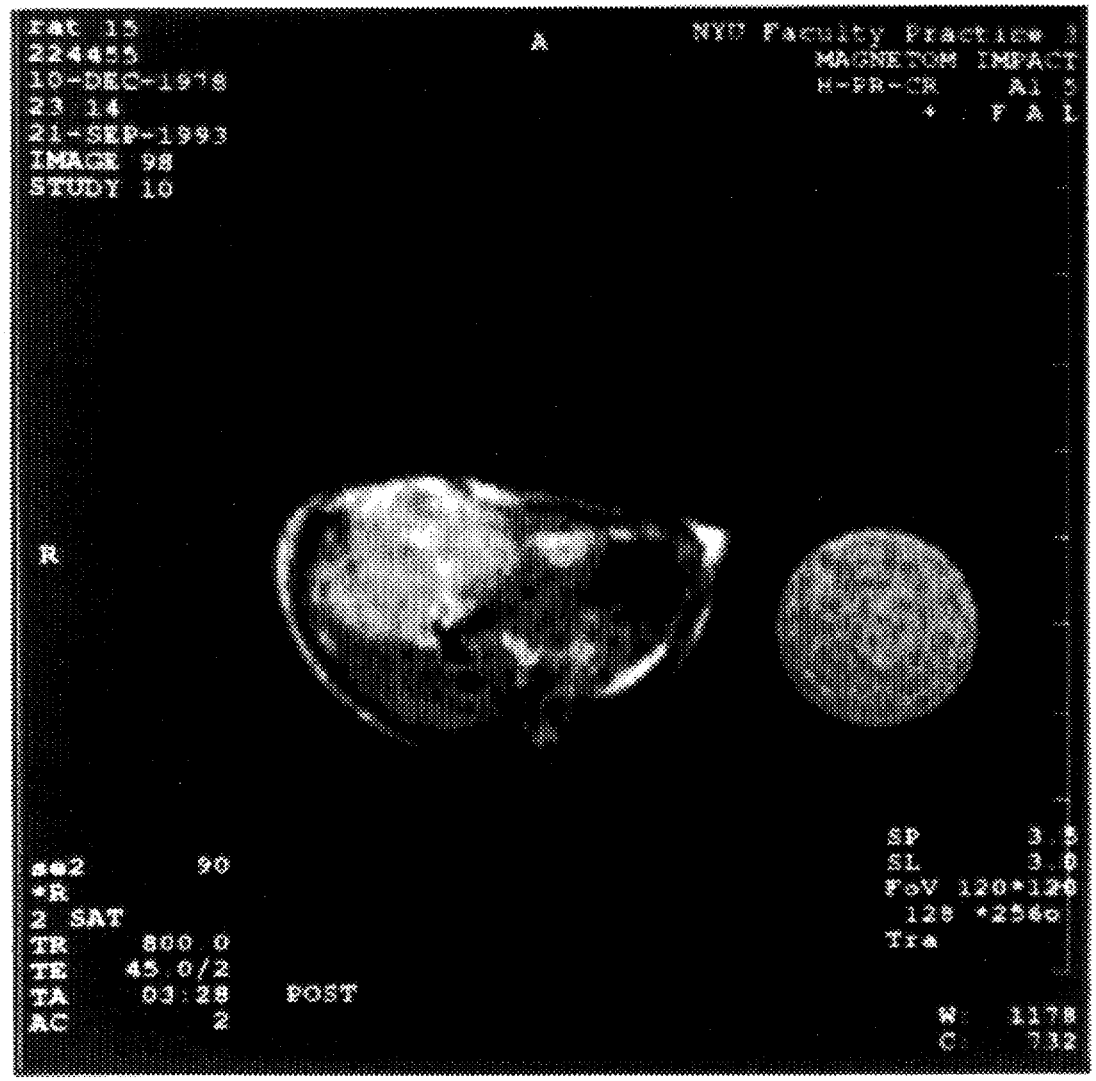
Figure 5:
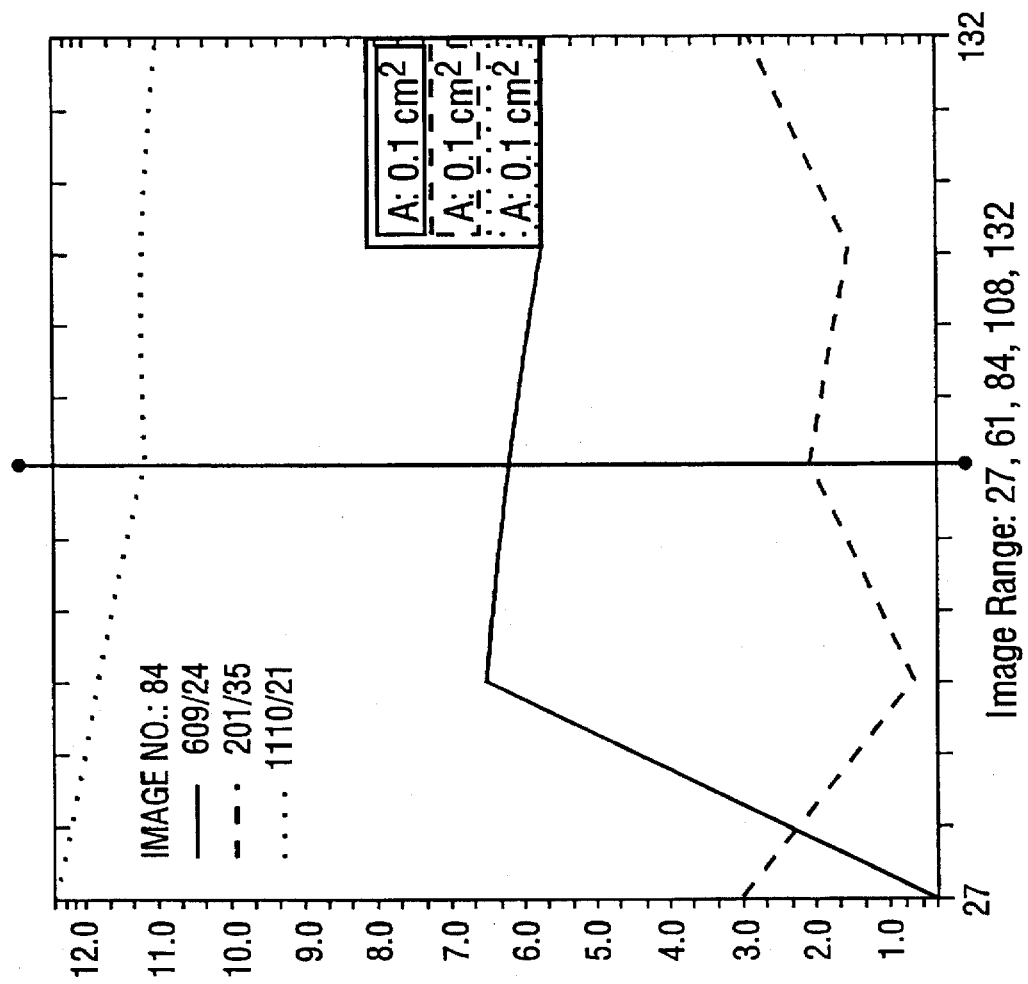
FIG. 5 Region-of-interest (ROI) analyses of MRI image intensities from a tumor animal analogous to that shown in FIGS. 4A–D. Upper line=tumor ROI's; Lower line=liver ROI's; time points=Precontrast; and 12, 27, 44 and 64 MPI of Ferrioxamine:Dermatan Sulfate Selective MRI Contrast Agent. Note the Intensity Ratios of Tumor to Liver are: (a) at the Peak time of 12 MPI=11:1; (b) as an average over the 27–64 MPI=3.2:1—both (a) and (b) additionally indicating very good selectivity for tumor versus liver. Intensity fades only very gradually with time, unlike the kinetics reported for Gd:DTPA, which are very rapid and have a t1/2 at the site of ca. 12–20 min (images not shown).
Figure 6:
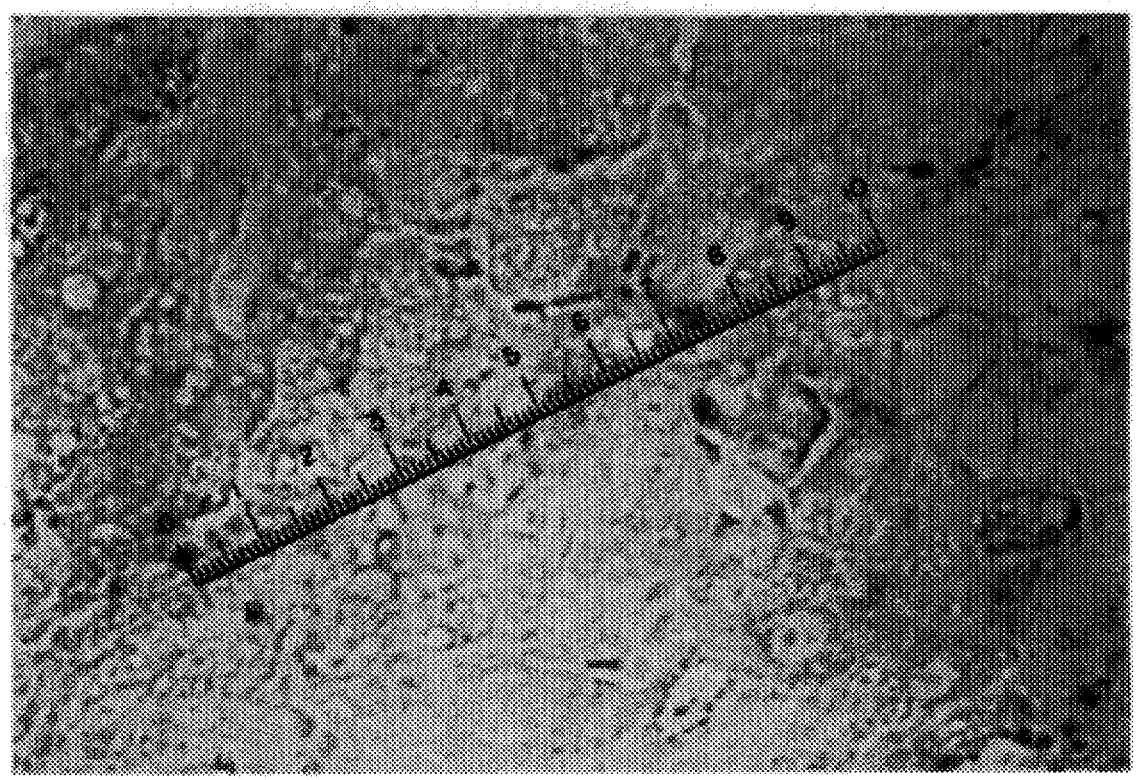
FIG. 6 Special histologic stain (heated ferroferricyanide reaction) of formalin-fixed section of Outer Tumor Rim 7–10 MPI of Ferrioxamine:Dermatan Sulfate Selective MRI Contrast Agent. Note selective staining for ferrioxamine iron (a) strongly positive on and within tumor endothelium, (b) strongly positive in the subendothelia, (c) moderately positive in the extracellular matrix of tumor, and (d) lightly to moderately positive within tumor intracellular sites.
Figure 7A:
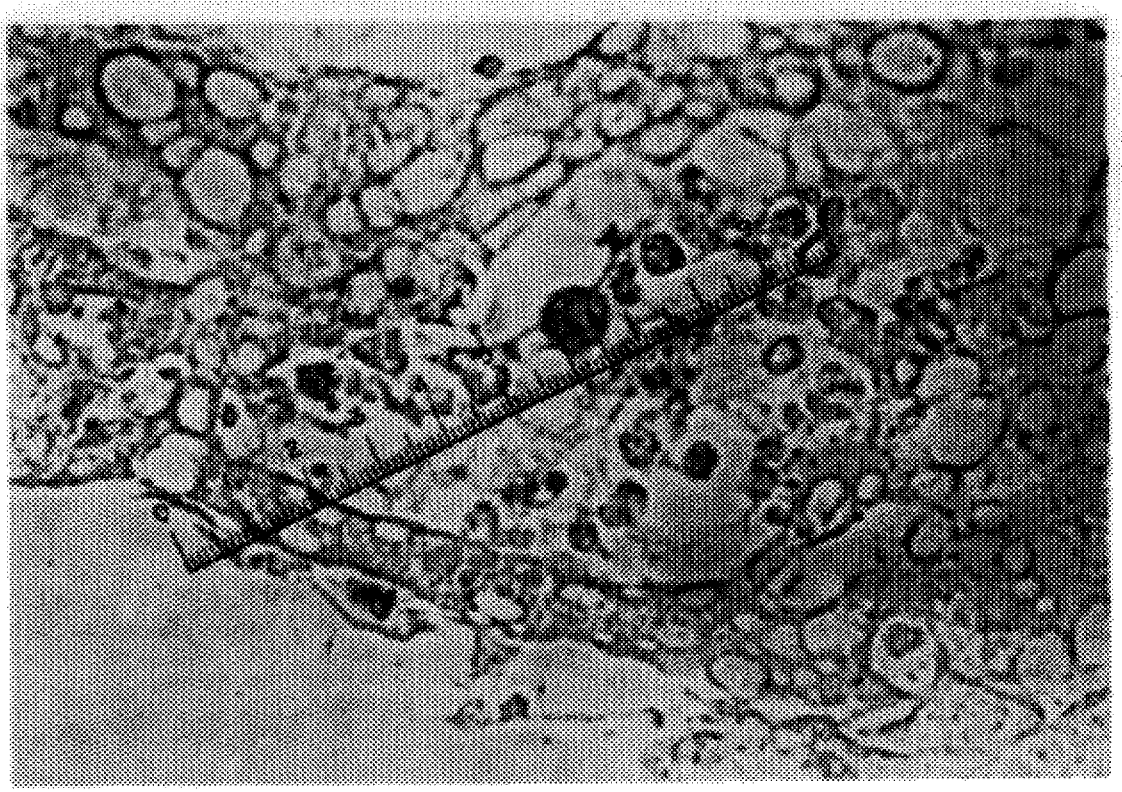
FIG. 7A Same stain, conditions, and post-contrast time as FIG. 6, except tissue section is taken from Central Tumor, 7–10 MPI of Ferrioxamine:Dermatan Sulfate Selective MRI Contrast Agent. Significant staining positivity is present at all sites as in FIG. 6.
Figure 7B:
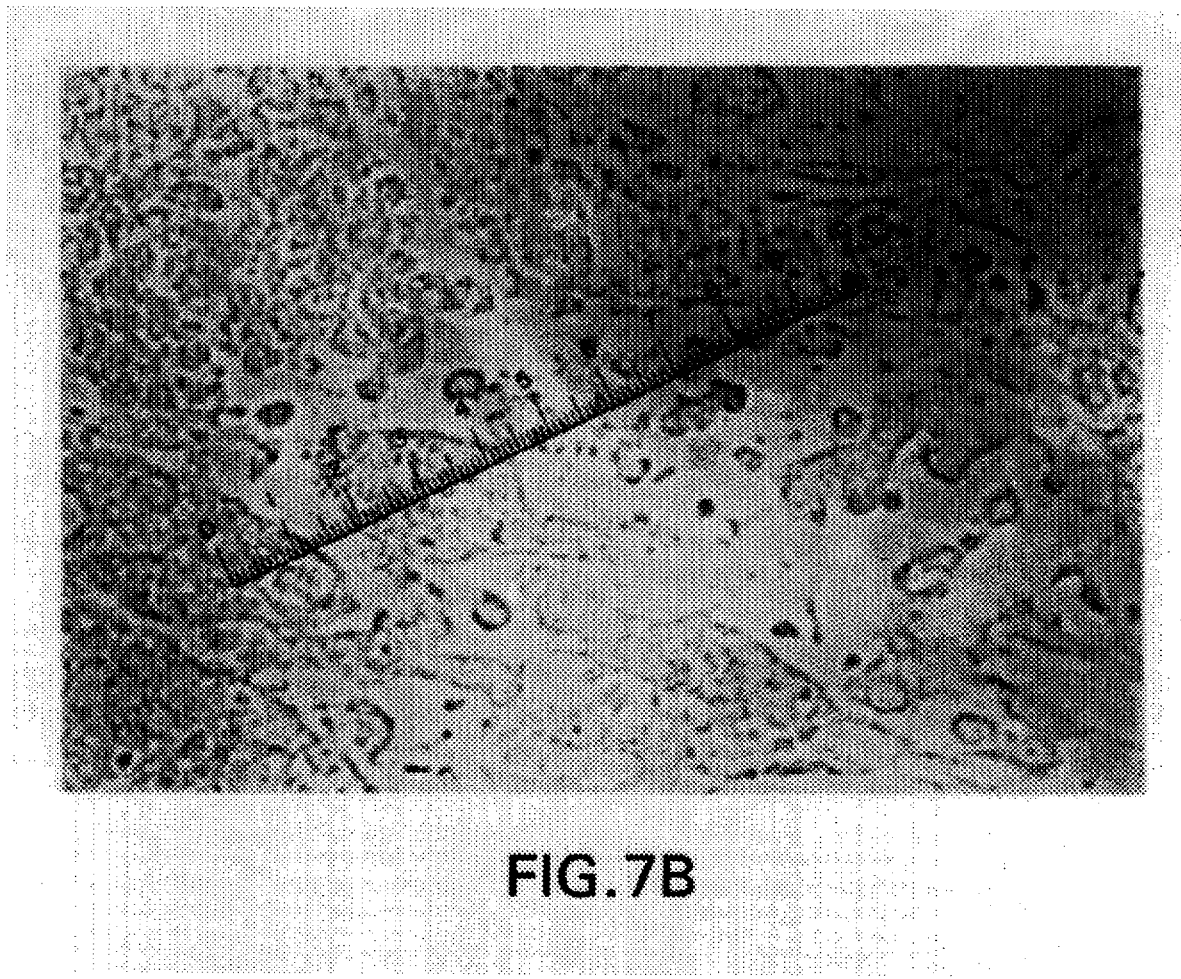
FIG. 7B Identical to 7A, except 7–10 MPI of Ferrioxamine Active Alone. Note the complete absence of staining positivity. This correlates directly with the results of MRI imaging with the full Agent (Active bound to Carrier) versus that with Active Alone (Active in free form)—(refer to FIGS. 2A and B versus 3).
Figure 8A:
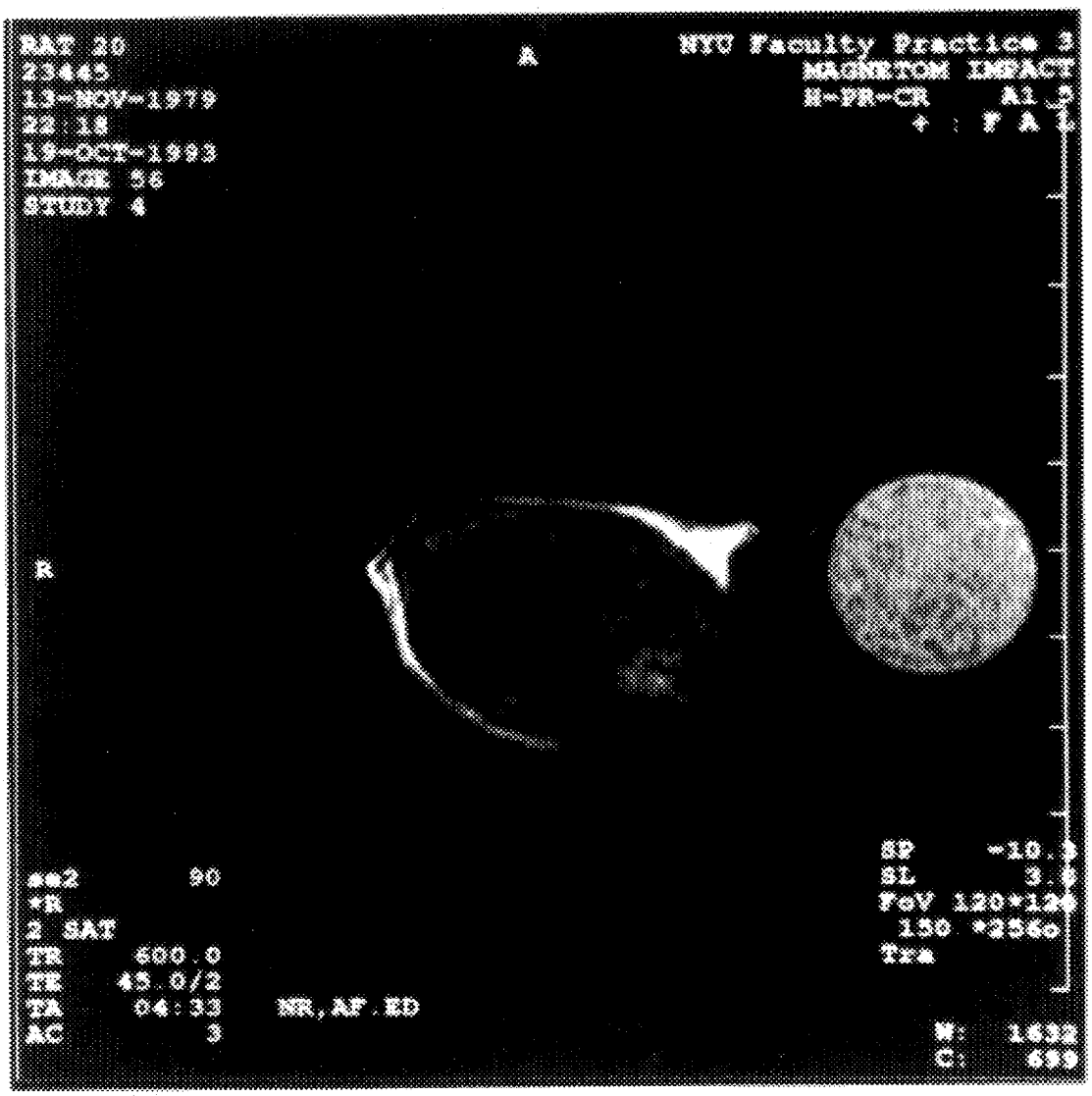
Figure 8B:
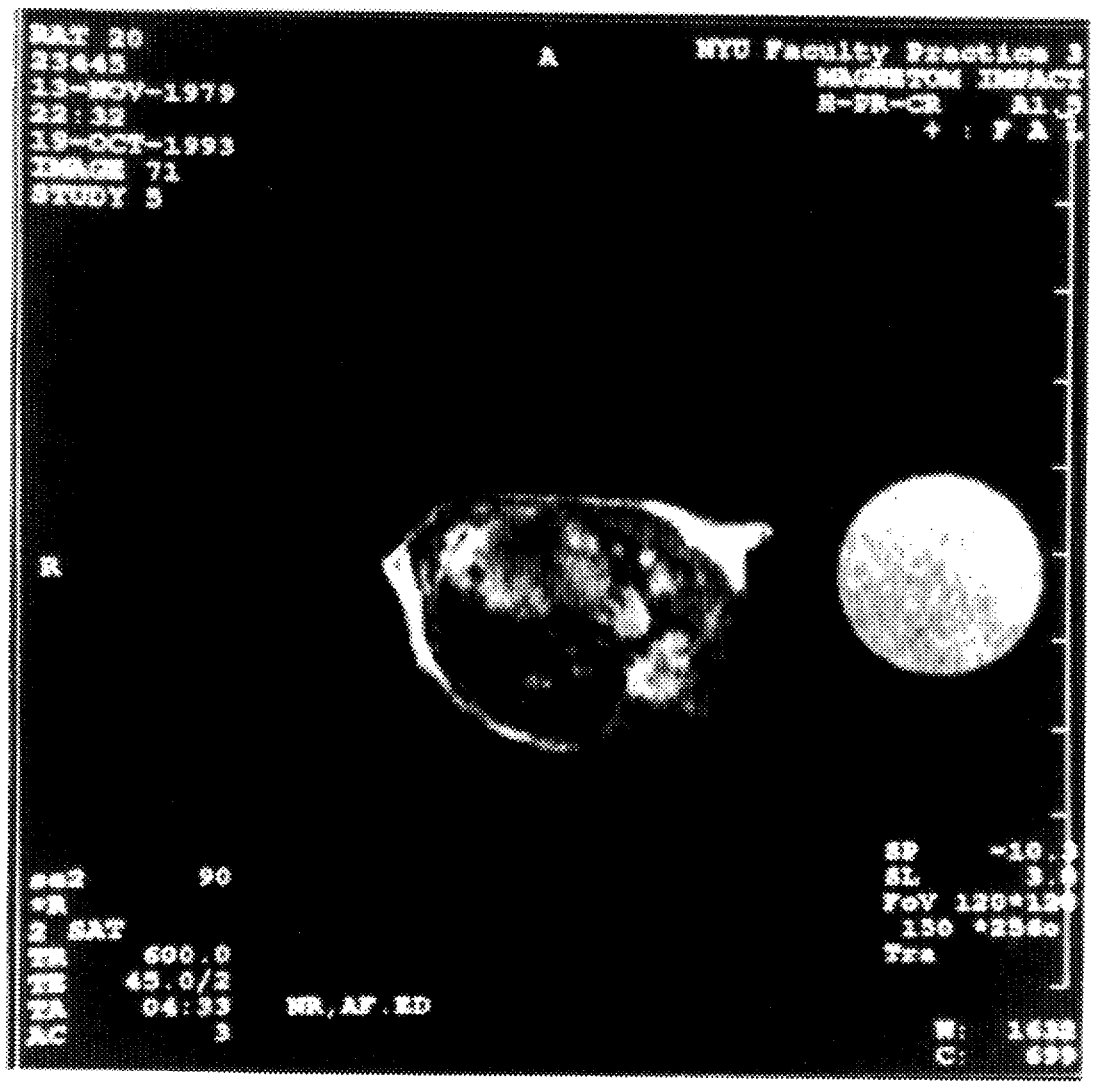
Figure 8C:
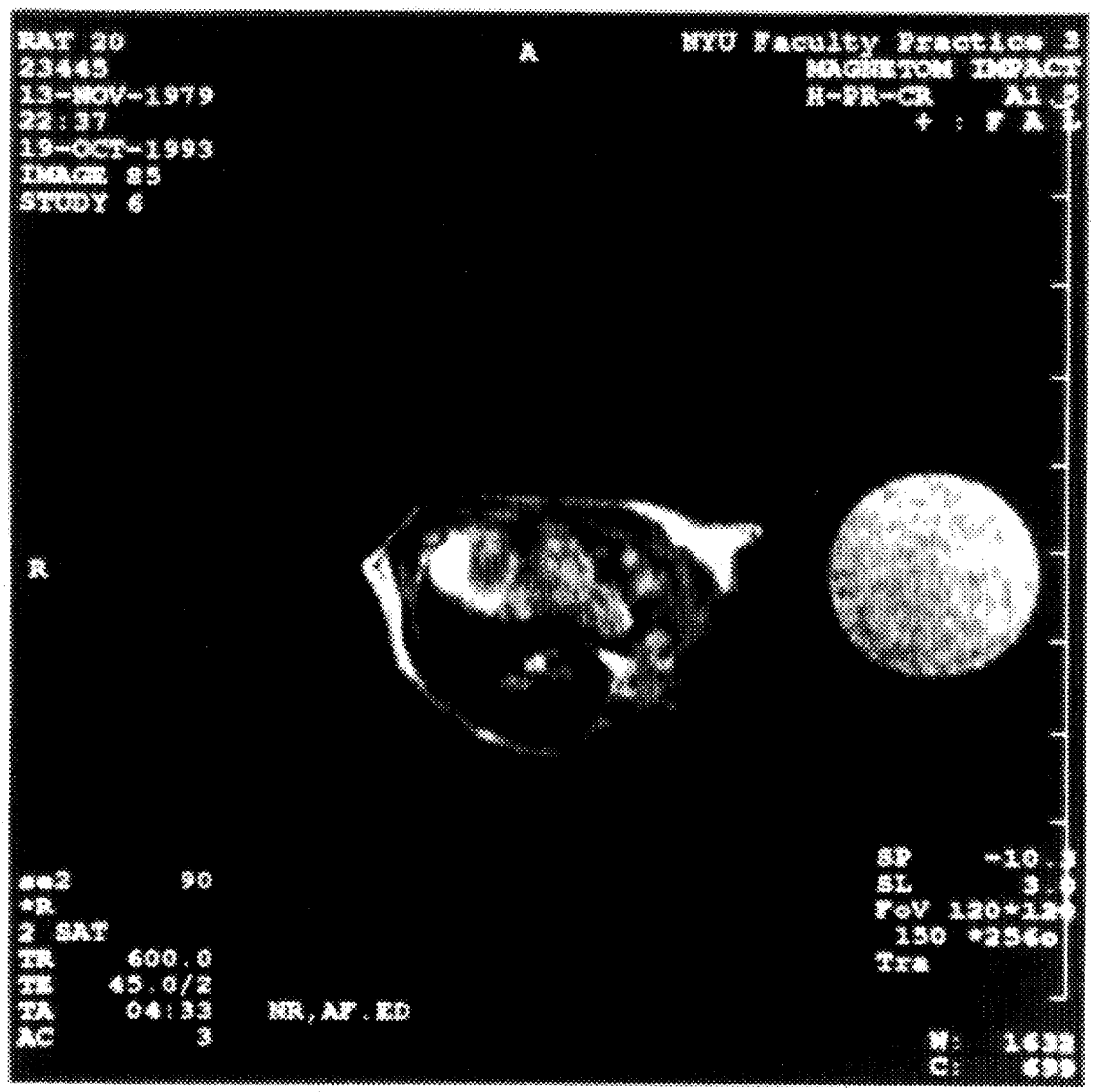
Figure 9A:
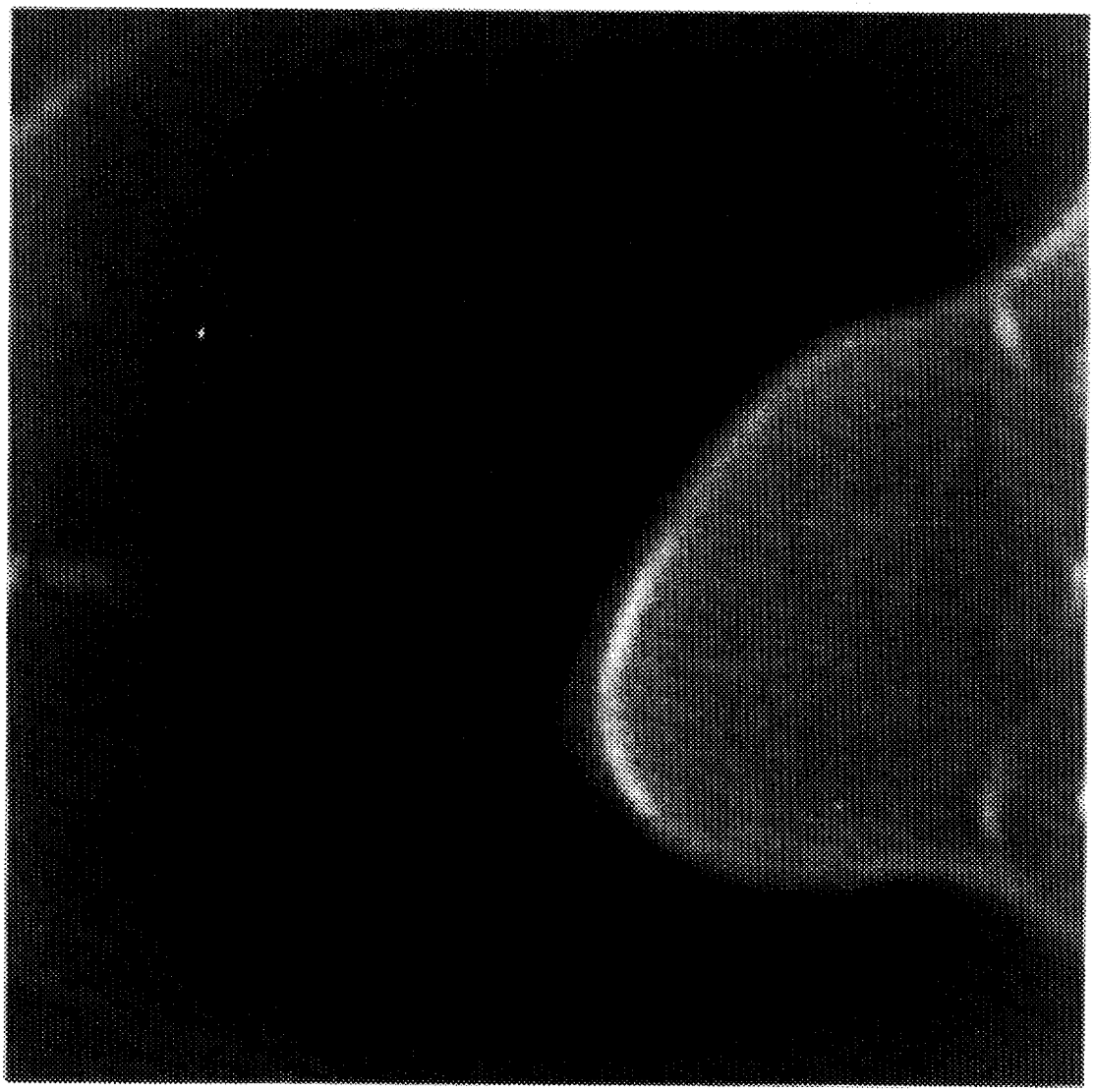
FIGS. 9A–E and 10A–E show T1-weighted MRI images (TR/TE=250/80) performed at 4.7 Tesla, before (Pre) and after (Post) intravenous (i.v.) injection of Ferrioxamine:D-ermatan Sulfate Selective Paramagnetic Contrast Agent (FIGS. 9A–E) prepared as in Examples 2 and 5, and injected i.v. at an Iron(III) dose of 0.155 mmol/Kg; compared to Gadolinium DTPA dimeglumine (FIGS. 10A–E), injected i.v. at a Gd(III) dose of 0.100 mmol/Kg; each of these agents being administered to Copenhagen rats with syngeneic AT-1 prostate adenocarcinoma inoculated into previously prepared skin pouches [Hahn et al. (1993)], such that tumor diameters at the time of imaging are between 1.0 cm and 2.5 cm.
Figure 9B:
Figure 9C:
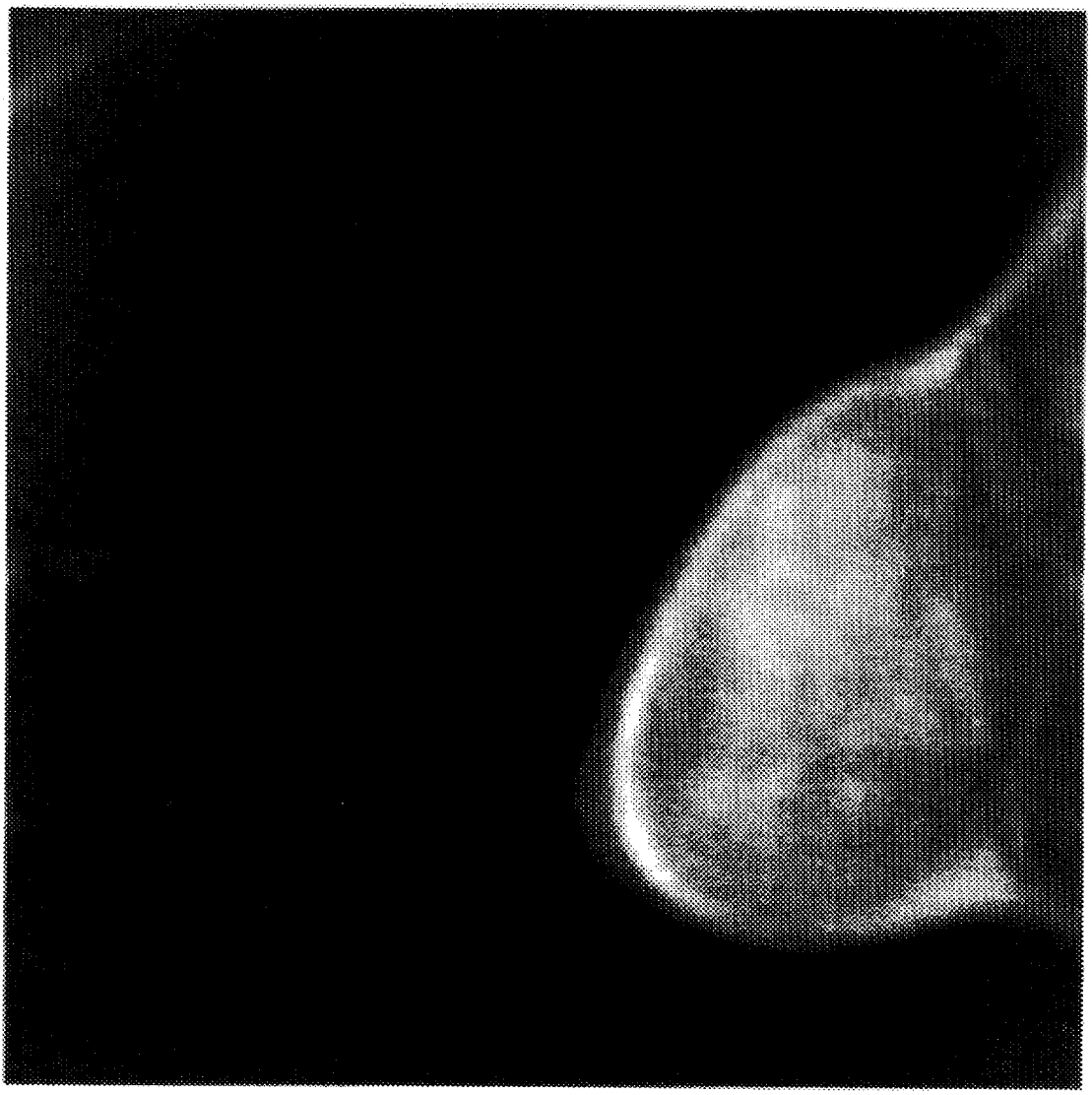
Figure 9D:
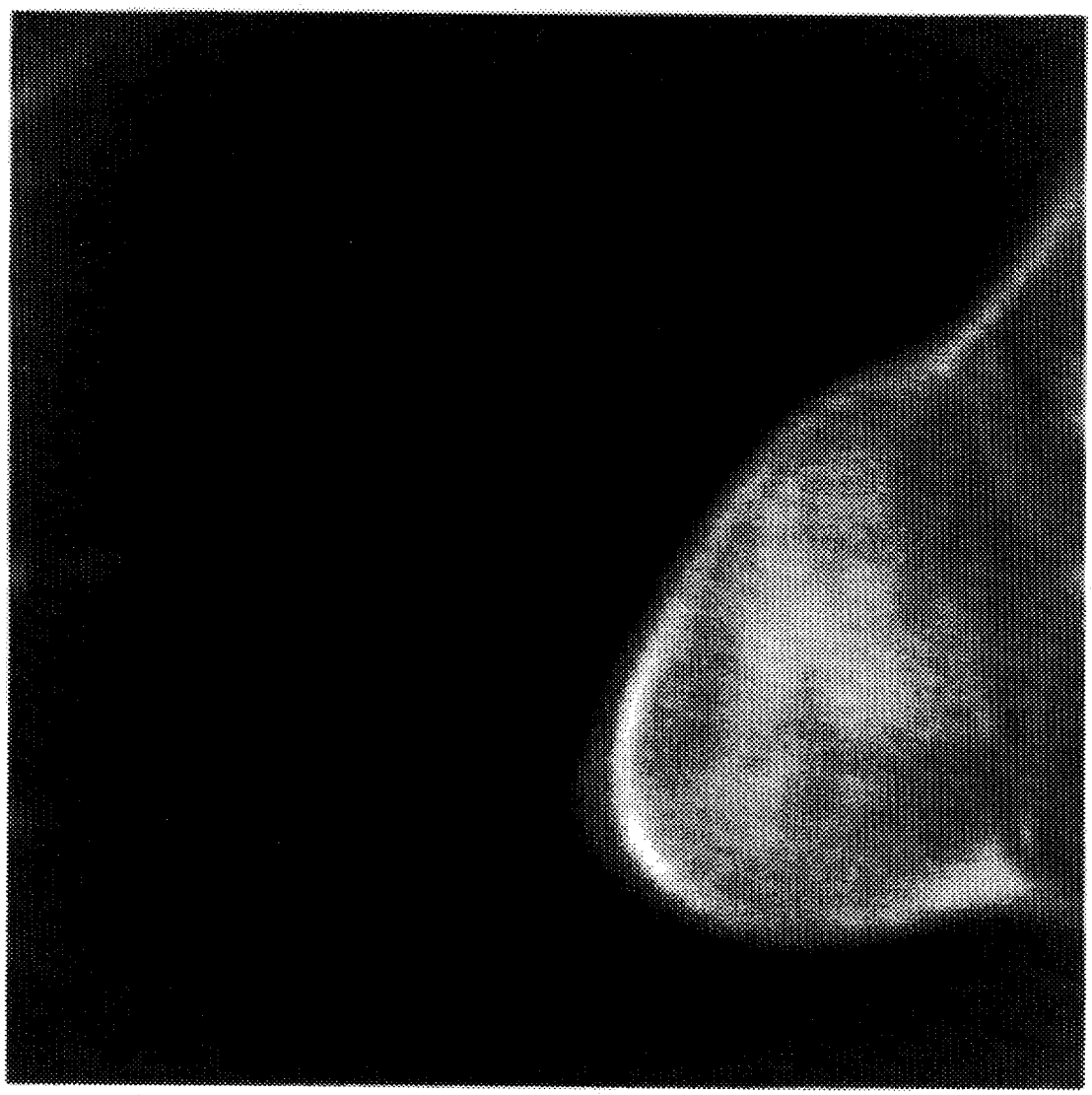
Figure 9E:
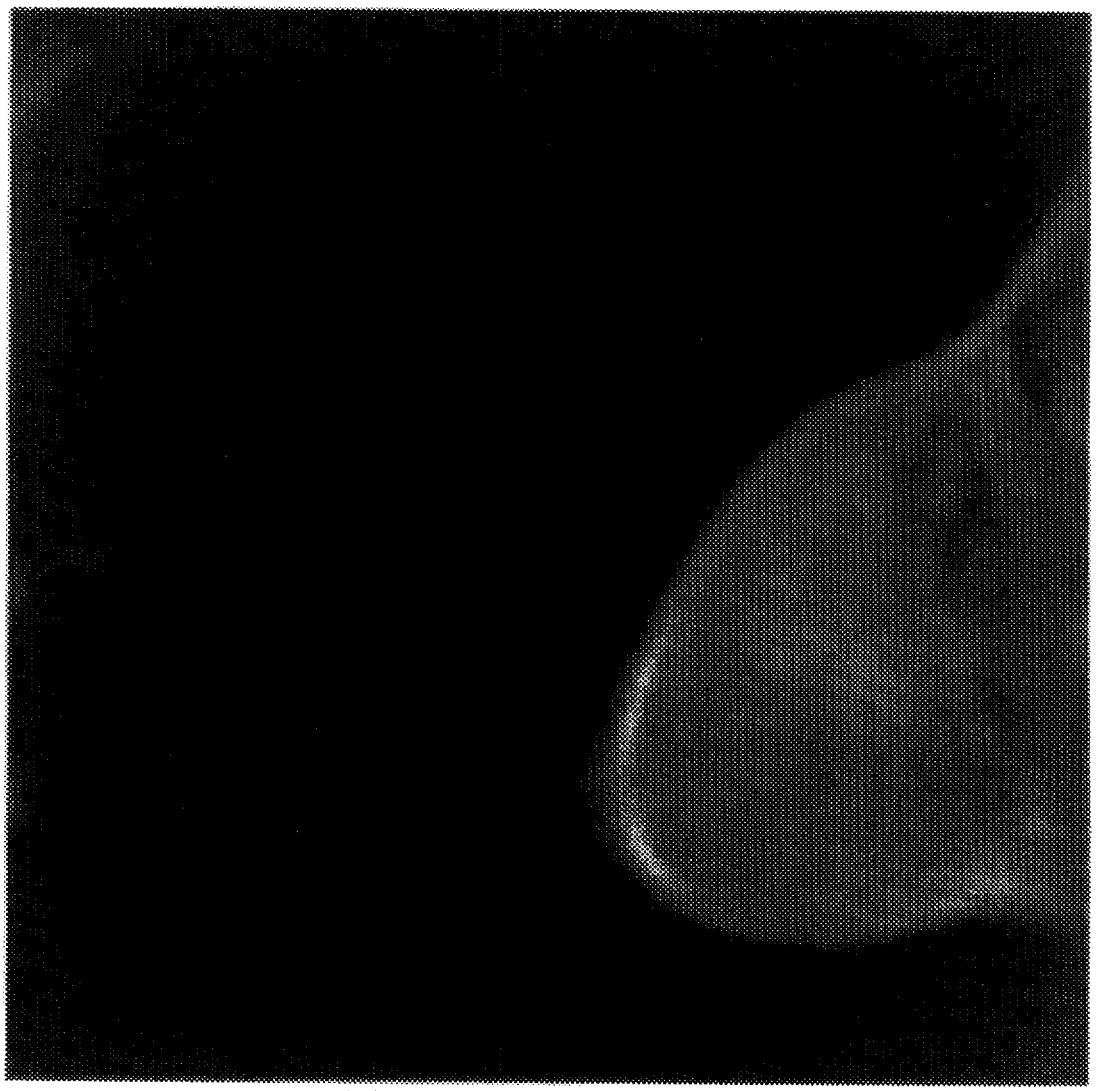
Figure 10A:
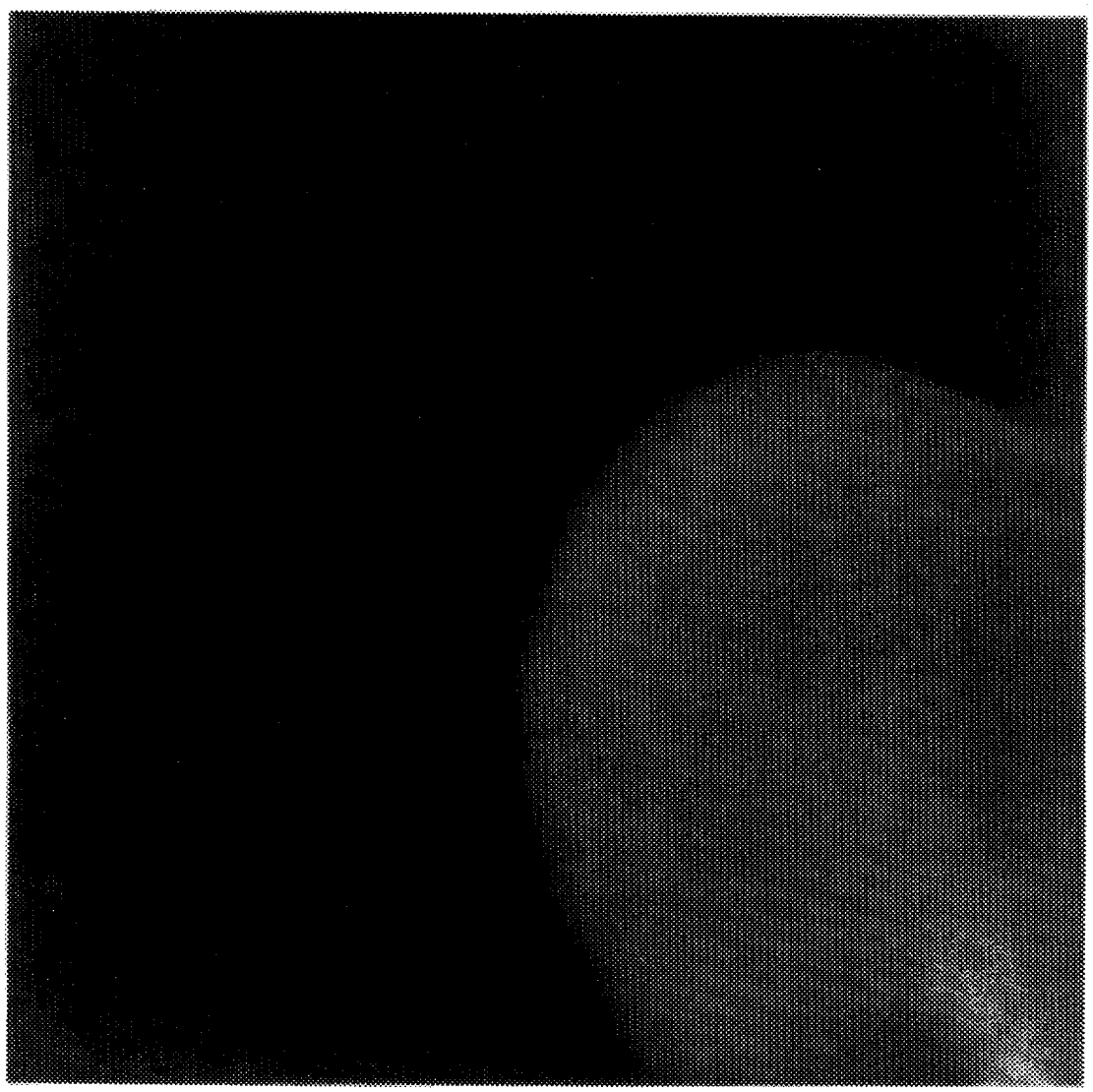
Figure 10B:
Figure 10C:
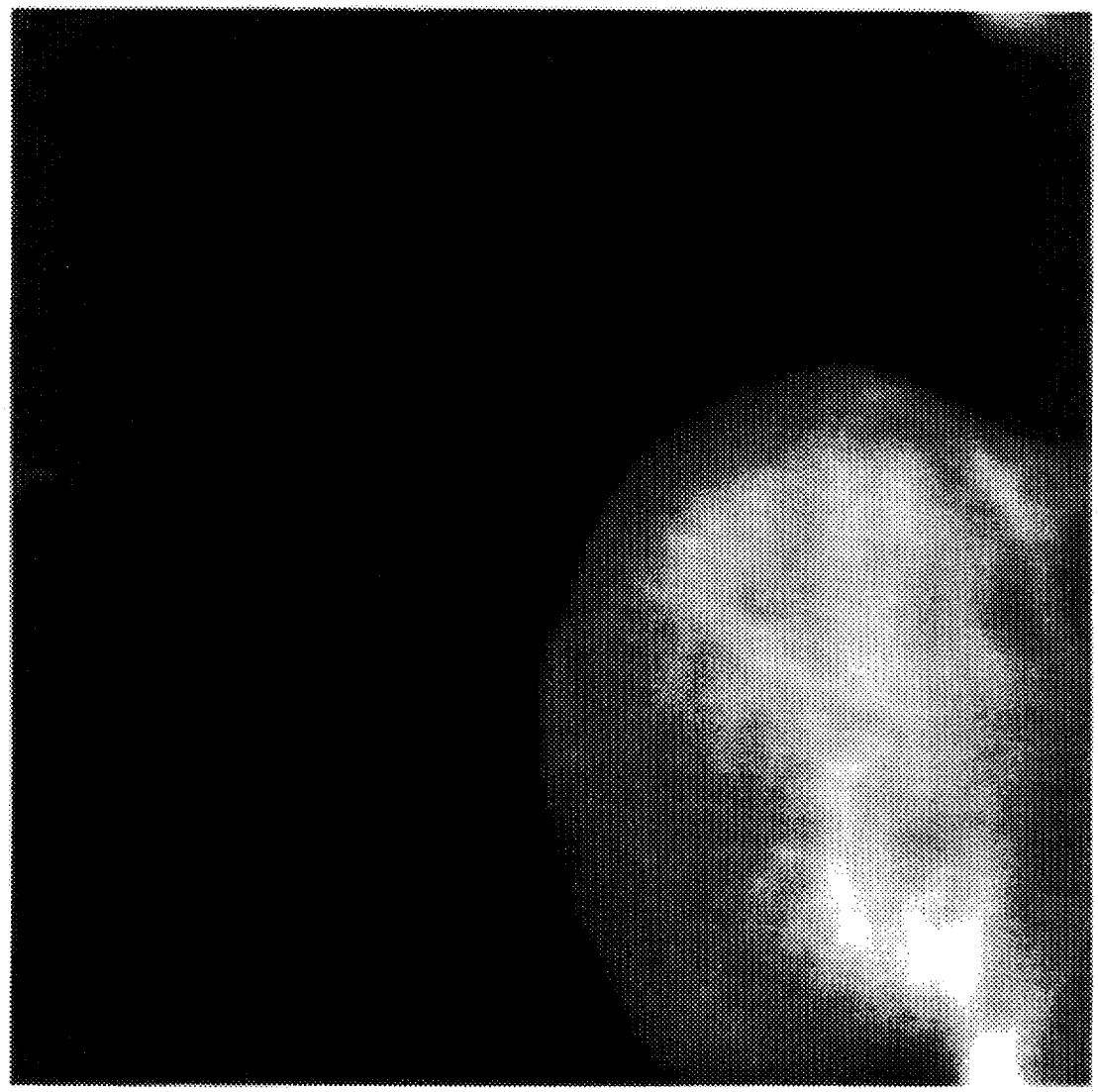
Figure 10D:
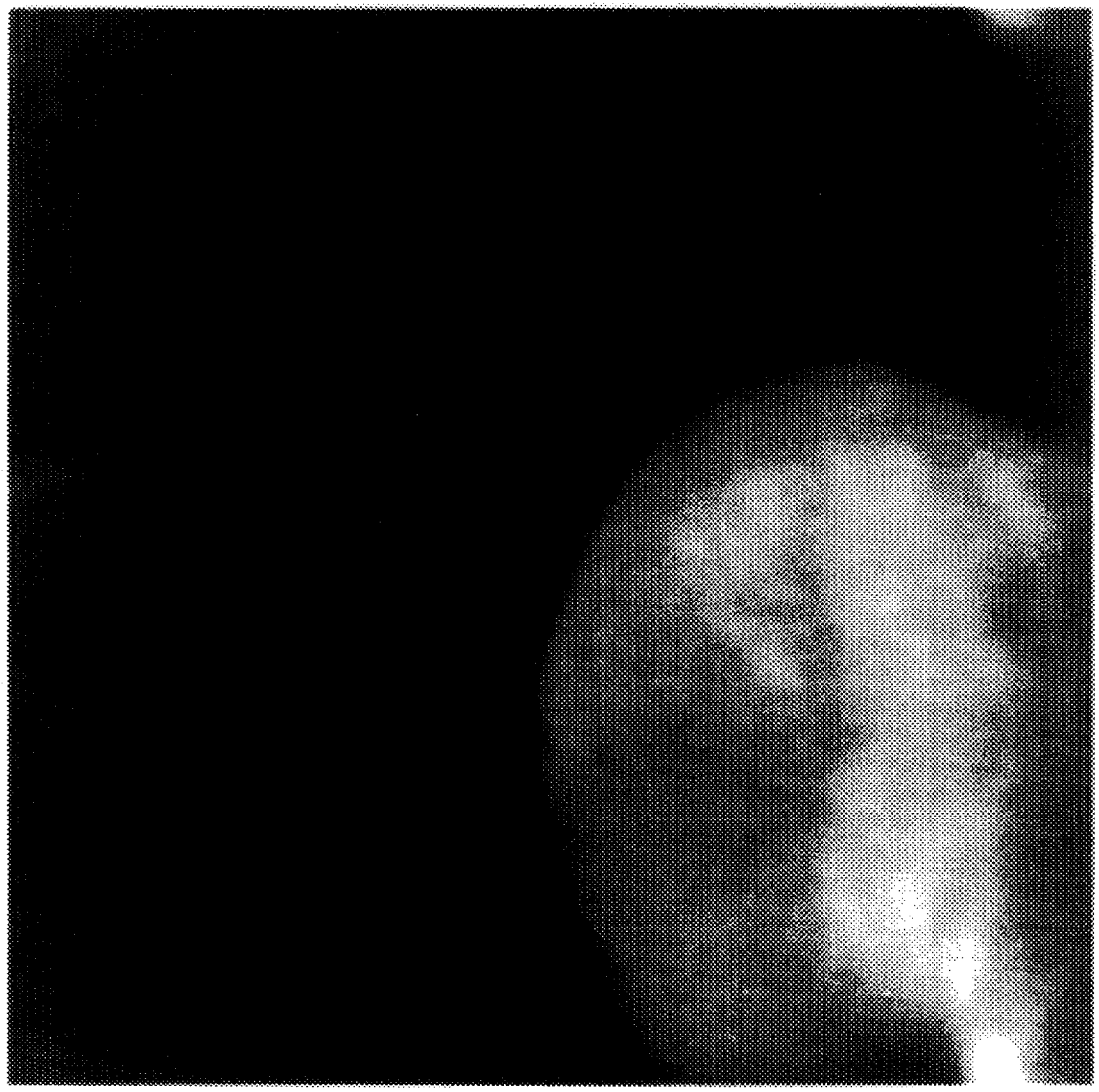
Figure 10E:
Figure 11A:
FIGS. 11A–D show T1-weighted MRI ECG-gated cardiovascular images performed at 0.5 Tesla, before (Pre) and after (Post) rapid intravenous (i.v.) infusion of Ferrioxamine:Dermatan Sulfate Selective Paramagnetic Contrast Agent prepared as in Examples 2 and 5, and injected i.v. at an Iron(III) dose of 0.155 mmol/Kg into German Shepherd dogs with acute, 90-min myocardial infarcts (ligature of proximal left anterior descending coronary artery) followed by reperfusion for ca. 90 minutes prior to contrast agent infusion.
Figure 11B:
Figure 11C:
Figure 11D:
Figure 12A:
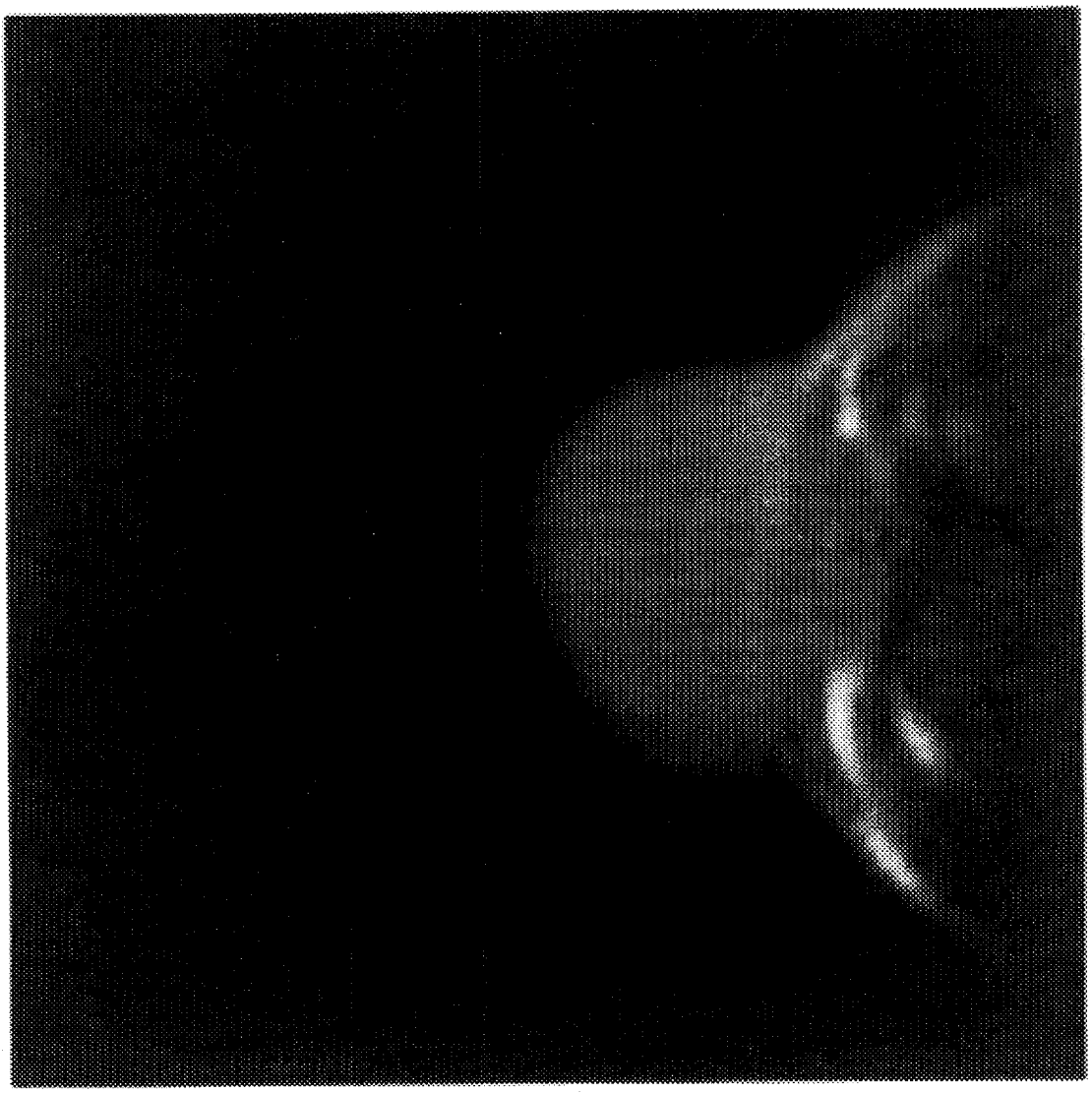
FIGS. 12A–D show MRI 4.7 Tesla, T1-weighted images of Copenhagen rats with the AT-1 prostate tumor model (as in FIGS. 9A–E and 10A–E), but rats are injected i.v. with Ferrioxamine:Dermatan Sulfate Selective Contrast Agent in the lyophilized (versus liquid) form, and the Agent is reconstituted with water just prior to administration at a higher concentration of 0.415 mmol/mL Fe(III) and administered at the usual dose of 0.155 mmol of Fe(III) per Kg.
Figure 12B:
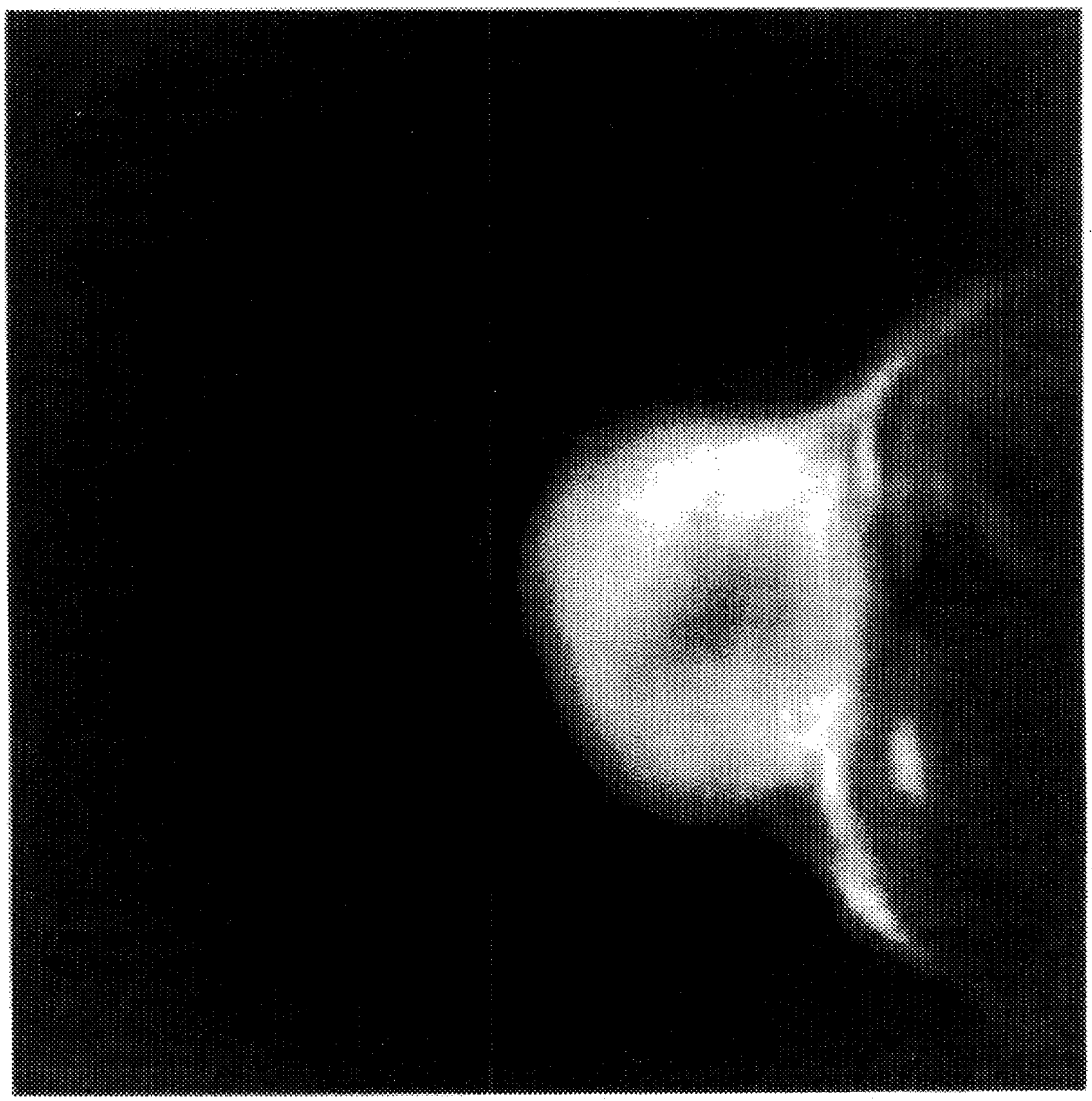
Figure 12C:
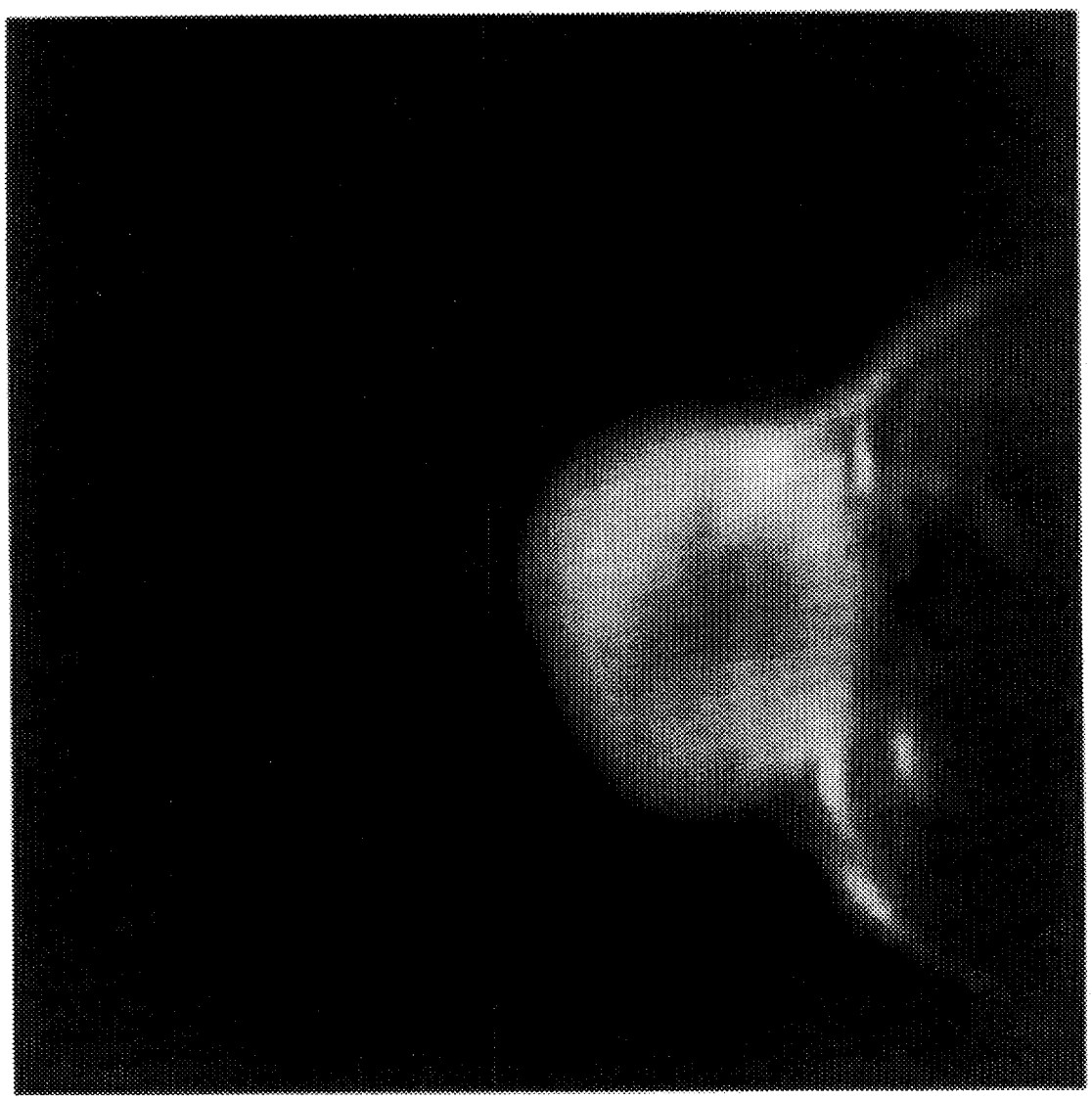
Figure 12D:
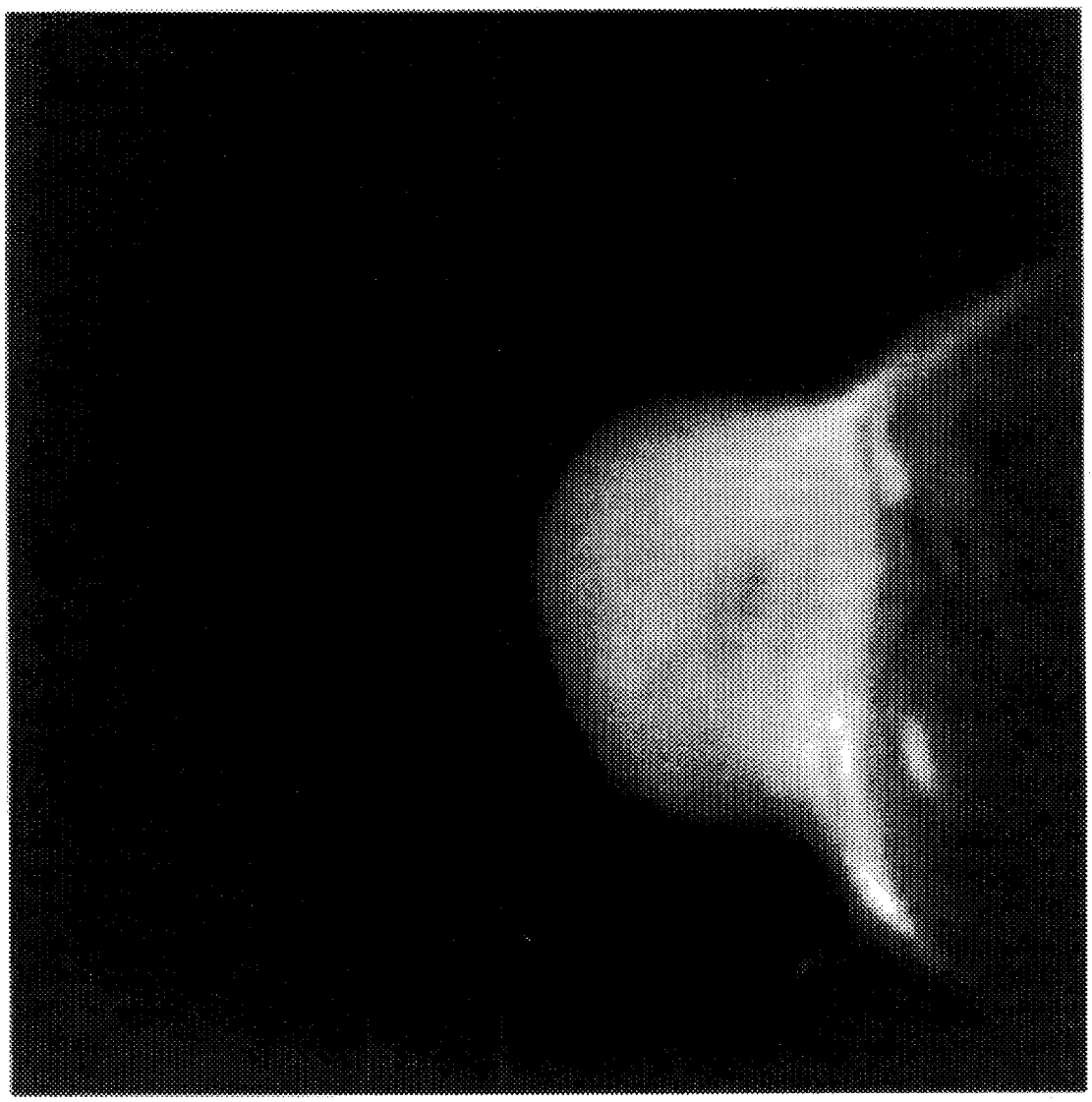
Figure 13A:
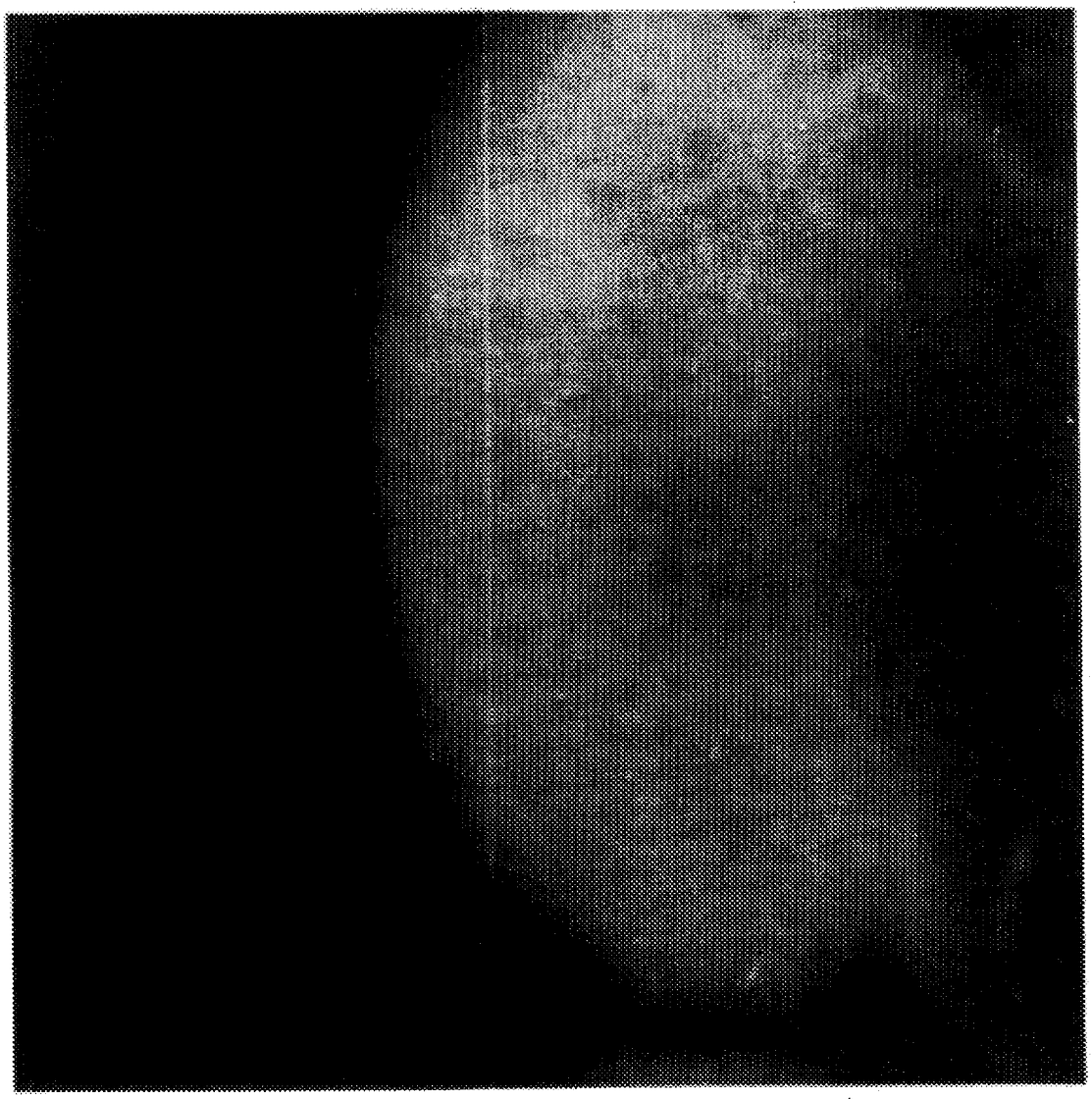
FIGS. 13A–D show MRI 4.7 Tesla, T1-weighted images of Copenhagen rats with the AT-1 prostate tumor model (as in FIGS. 12A–D), but rats are injected i.v. with Gd(III):DTPA-Lys:Dermatan Sulfate Selective Contrast Agent in liquid form pre-concentrated to 0.415 mmol/mL Gd(III) and administered at the usual dose of 0.155 mmol of Gd(III) per Kg.
Figure 13B:
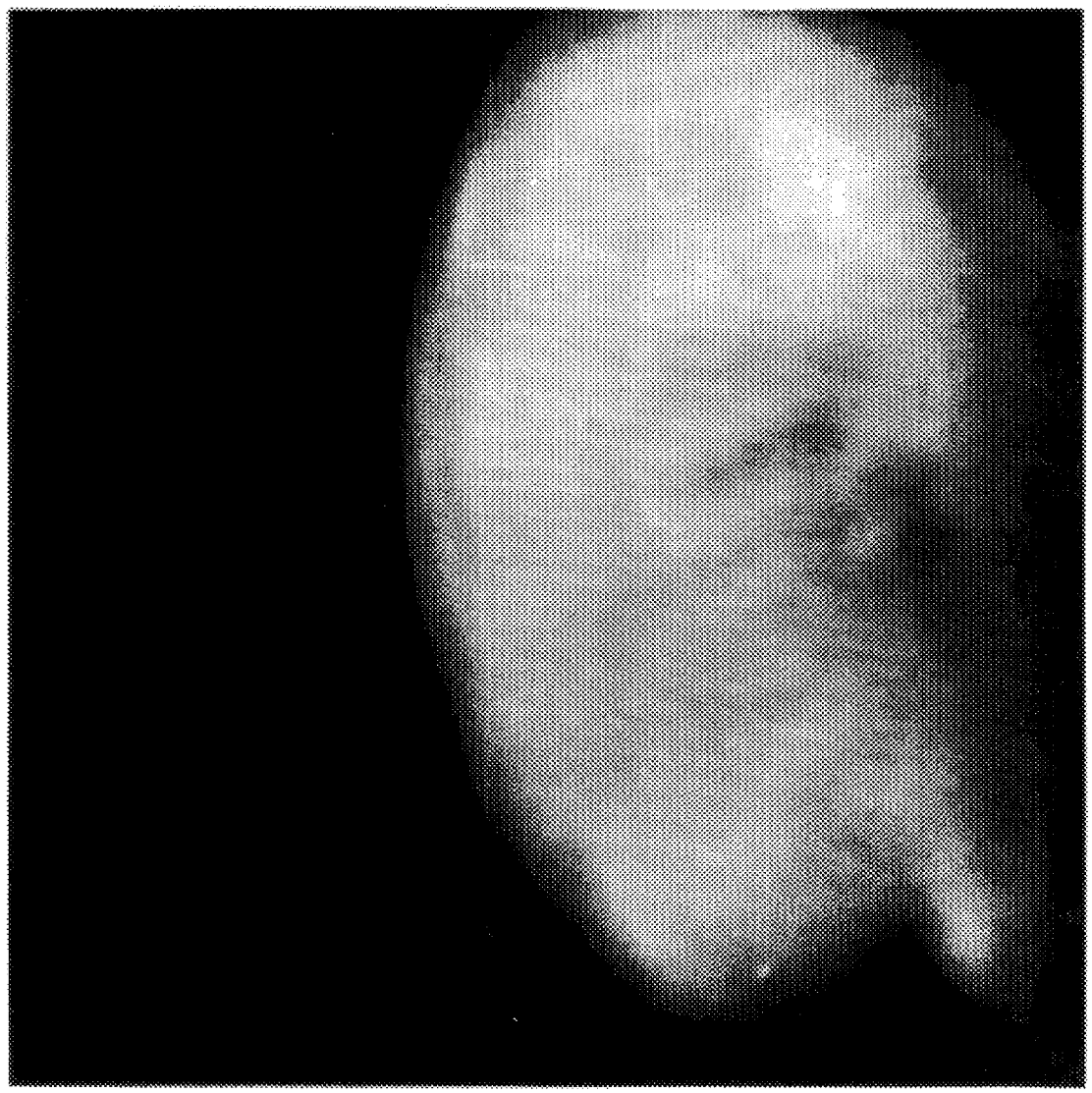
Figure 13C:
Figure 13D:
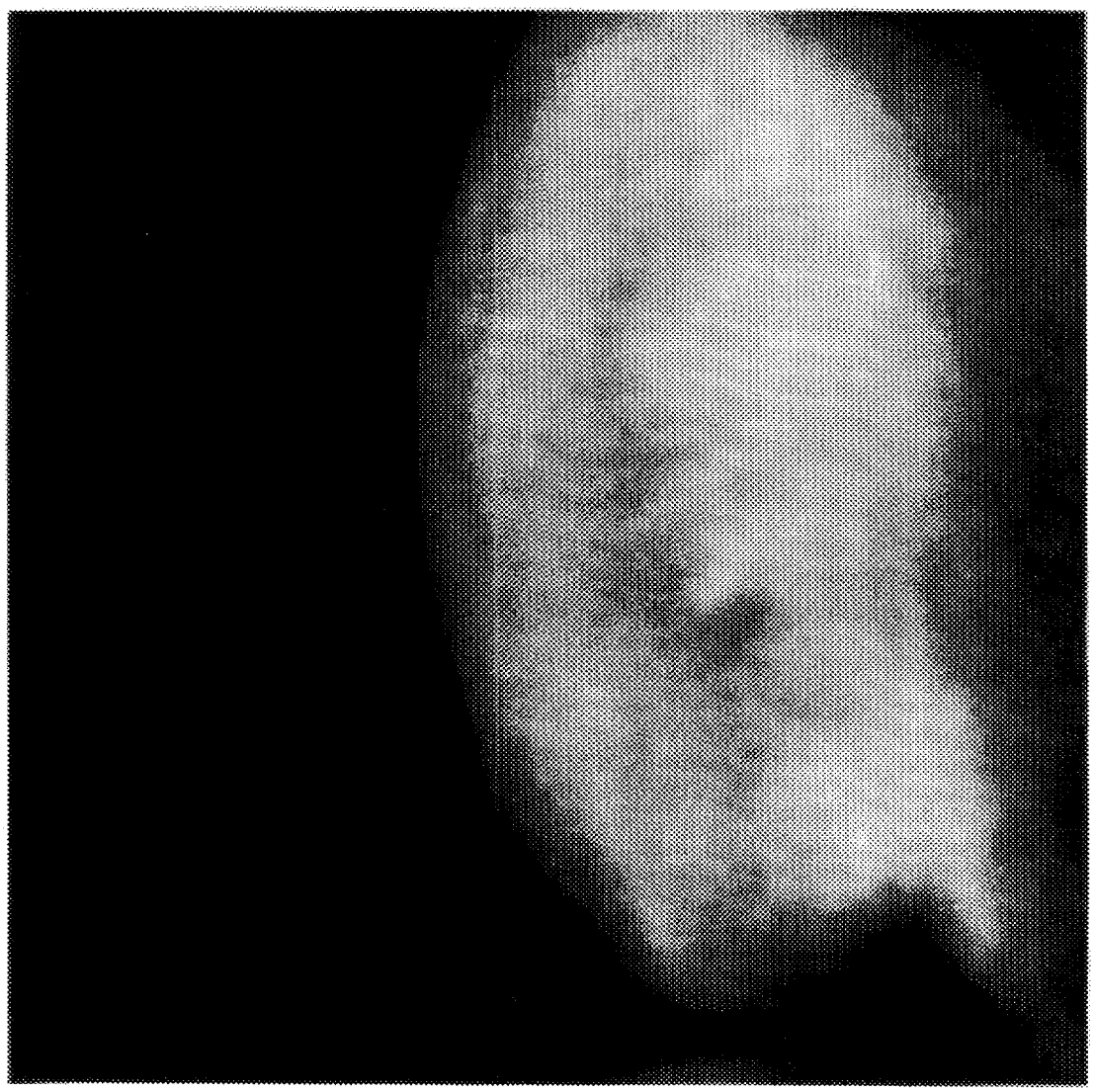
Figure 14A:
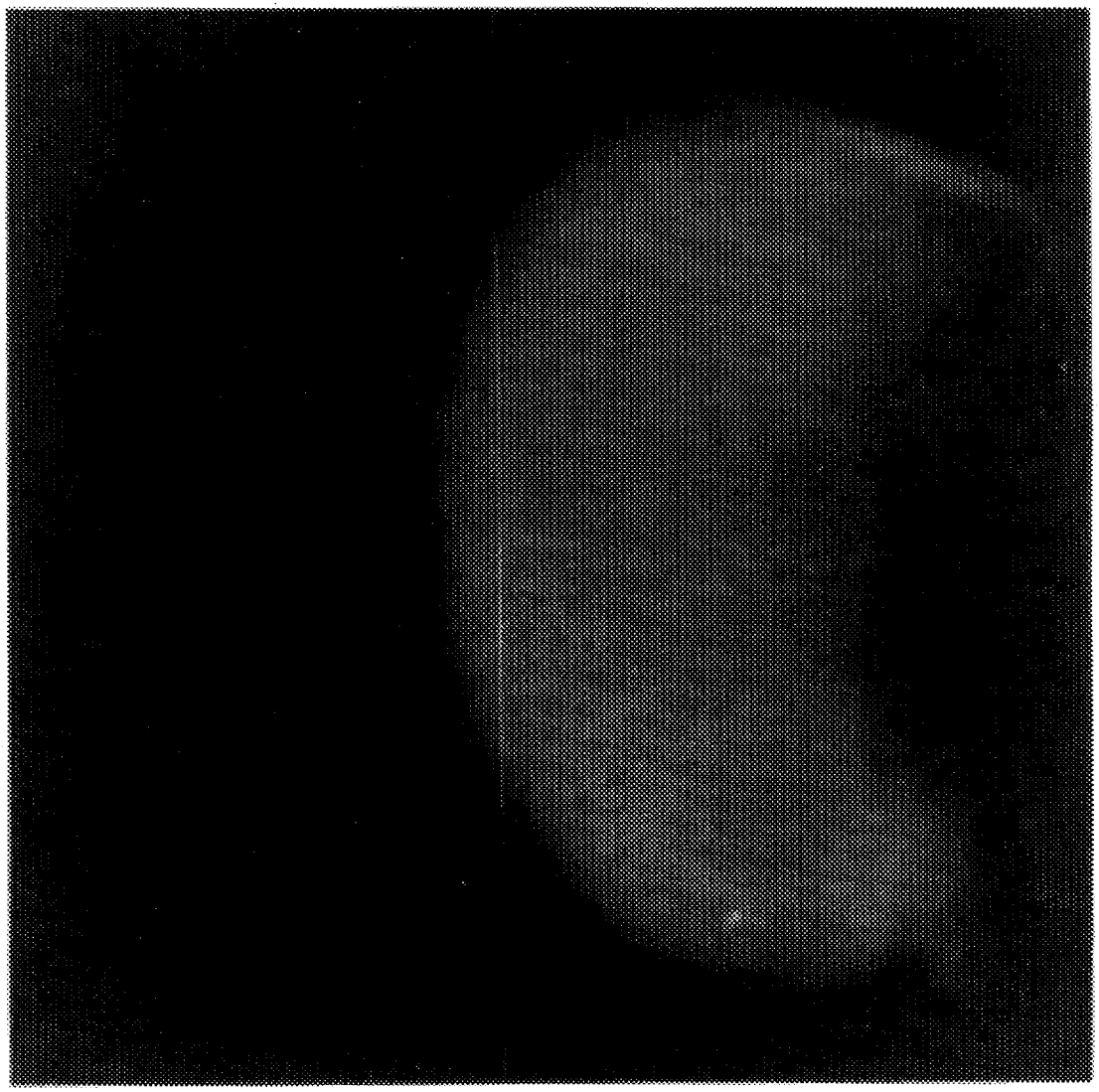
FIGS. 14A–D show MRI 4.7 Tesla, T1-weighted images of Copenhagen rats with the AT-1 prostate tumor model (as in FIGS. 13A–D), but rats are injected i.v. with Ferrioxamine Selective Contrast Agent, wherein the Active is non-covalently bound to Oversulfated Dermatan Sulfate, the Agent lyophilized and reconstituted with water just prior to administration at a concentration of 0.332 mmol/mL Fe(III) and administered at the usual dose of 0.155 mmol of Fe(III) per Kg.
Figure 14B:
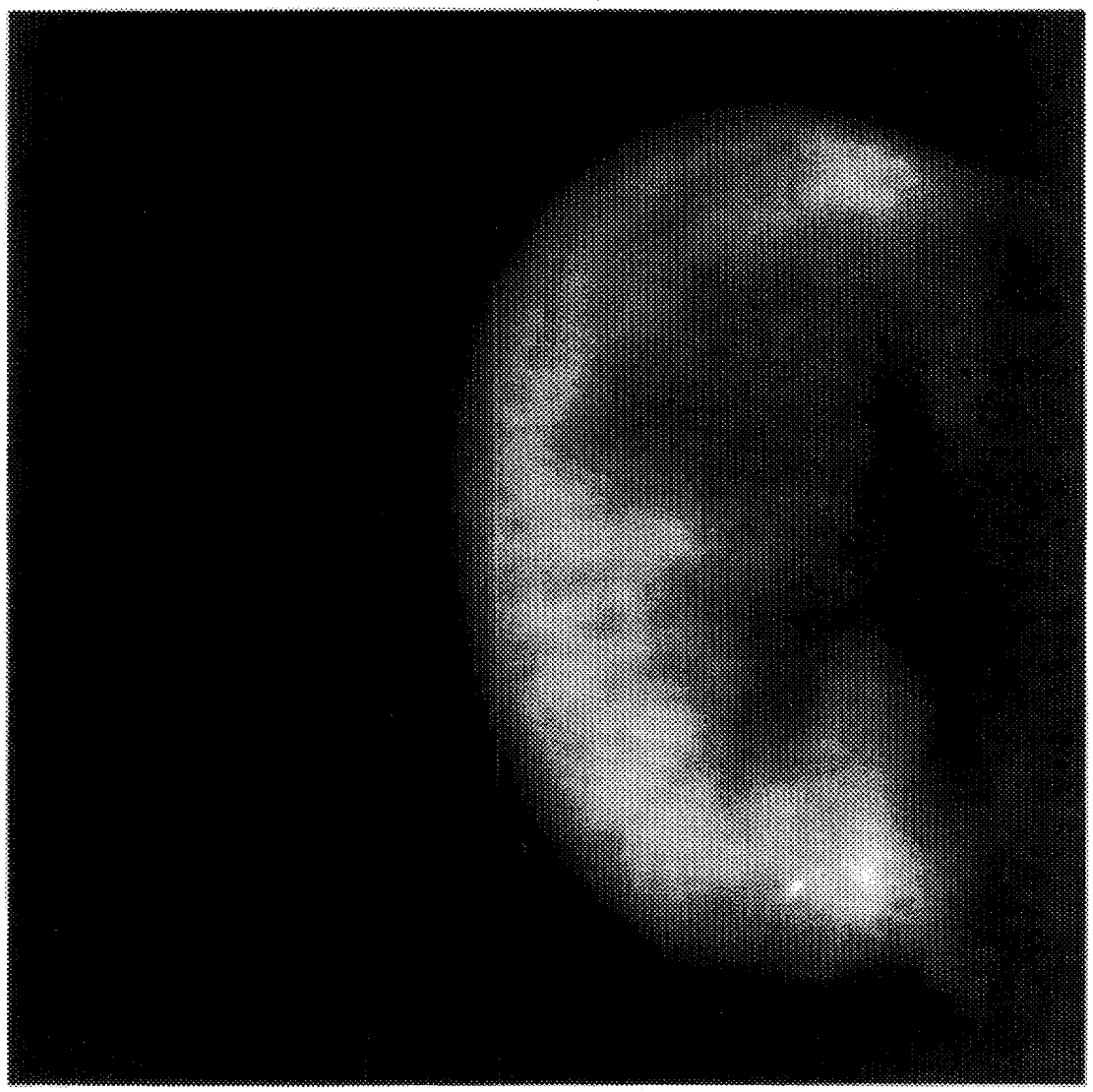
Figure 14C:
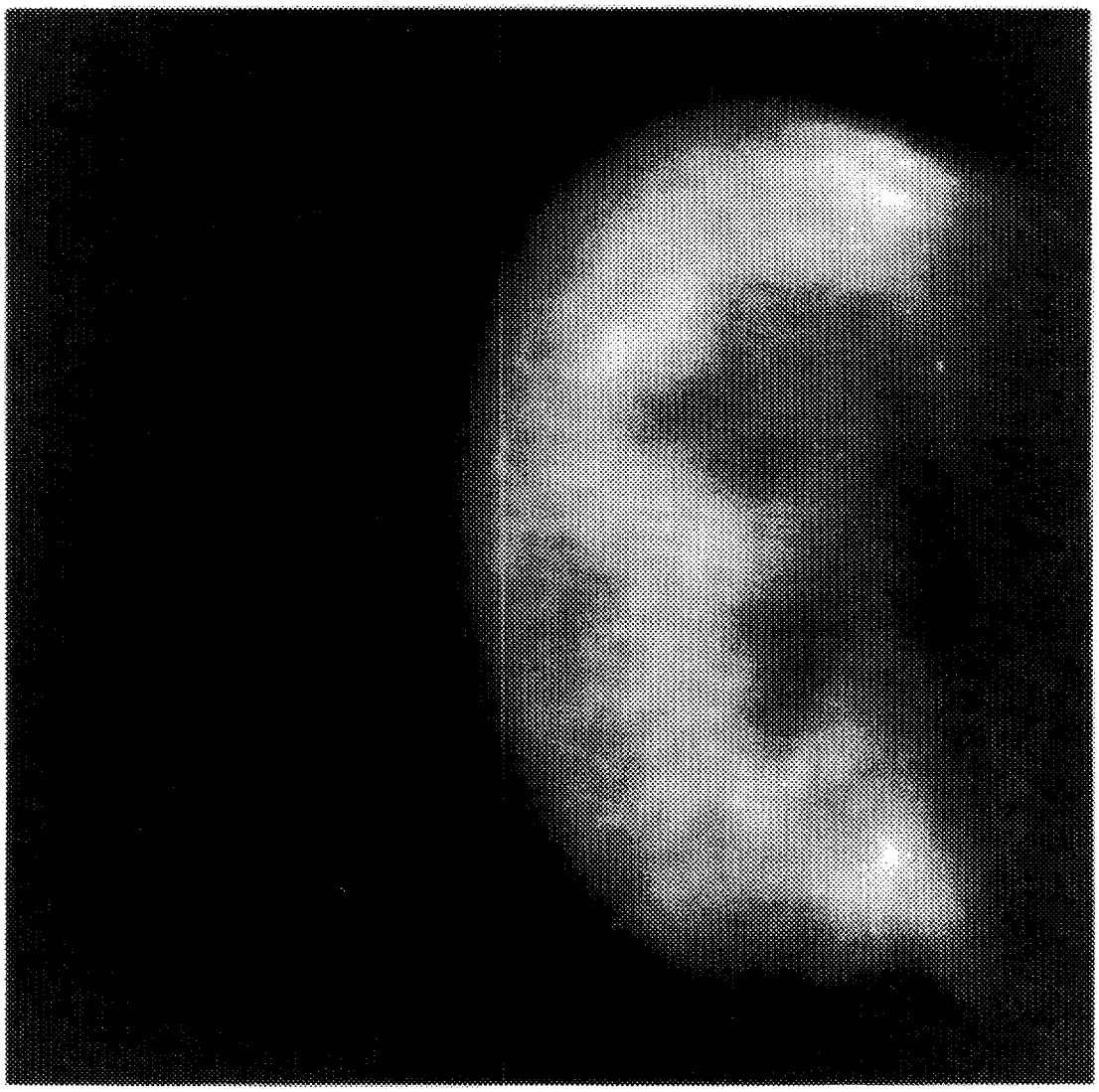
Figure 14D:
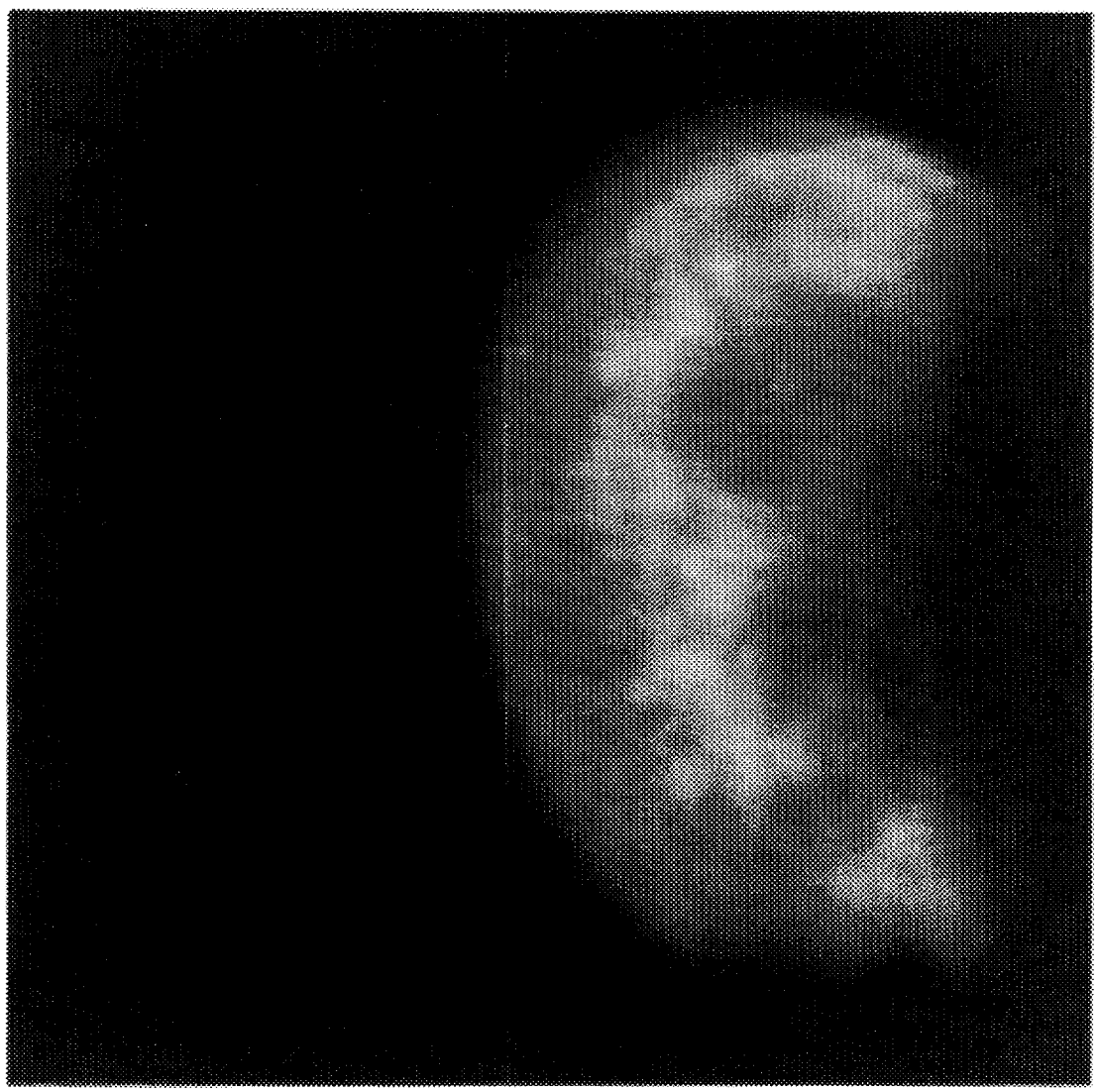
Figure 15A:
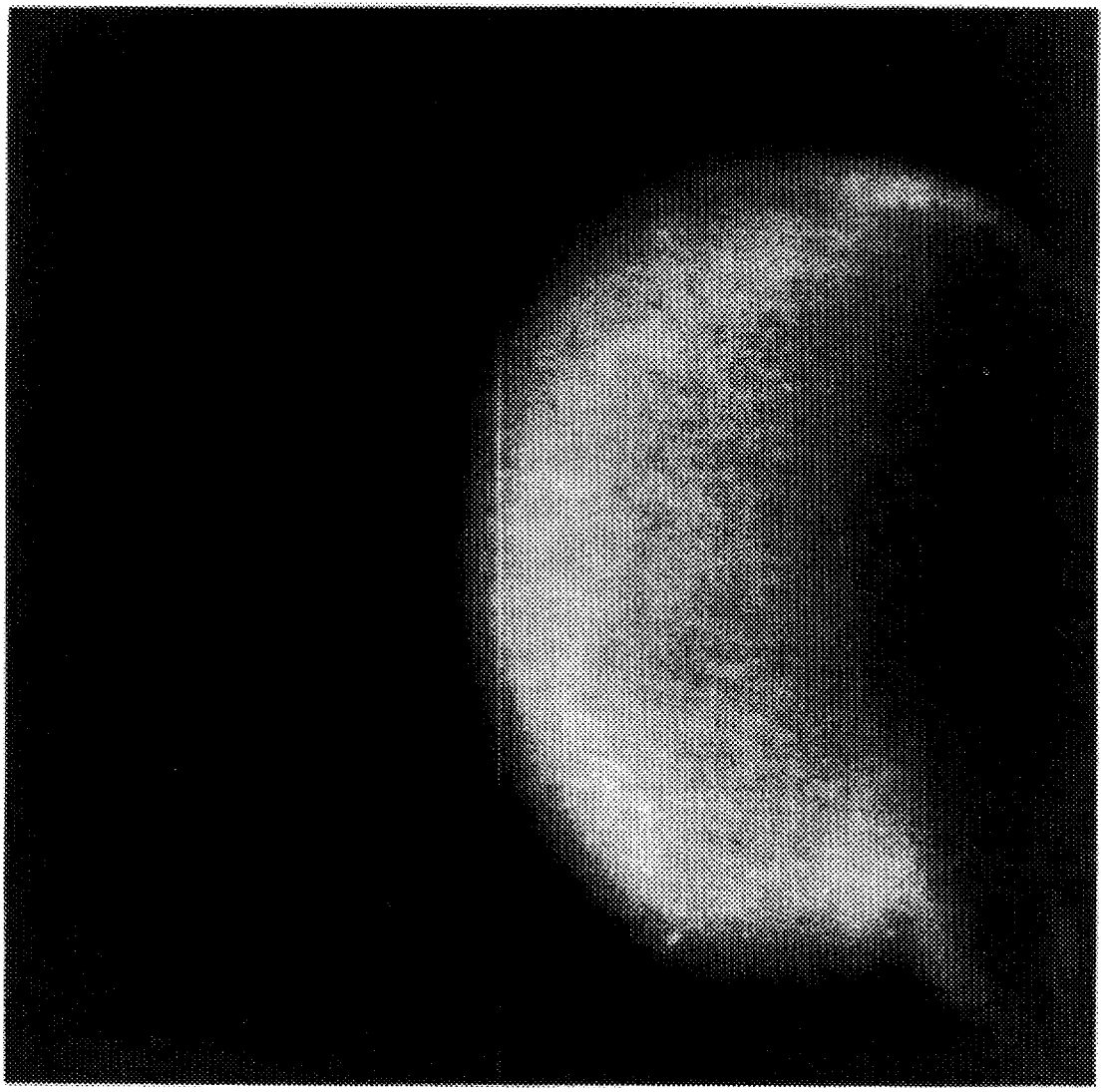
FIGS. 15A–D show MRI 4.7 Tesla, T1-weighted images of Copenhagen rats with the AT-1 prostate tumor model (as in FIGS. 13A–D), but rats are injected i.v. with Ferrioxamine Selective Contrast Agent, wherein the Active is non-covalently bound to Oversulfated Chondroitin Sulfate, the Agent lyophilized and reconstituted with water just prior to administration at a concentration of 0.332 mmol/mL Fe(III) and administered at the usual dose of 0.155 mmol of Fe(III) per Kg.
Figure 15B:
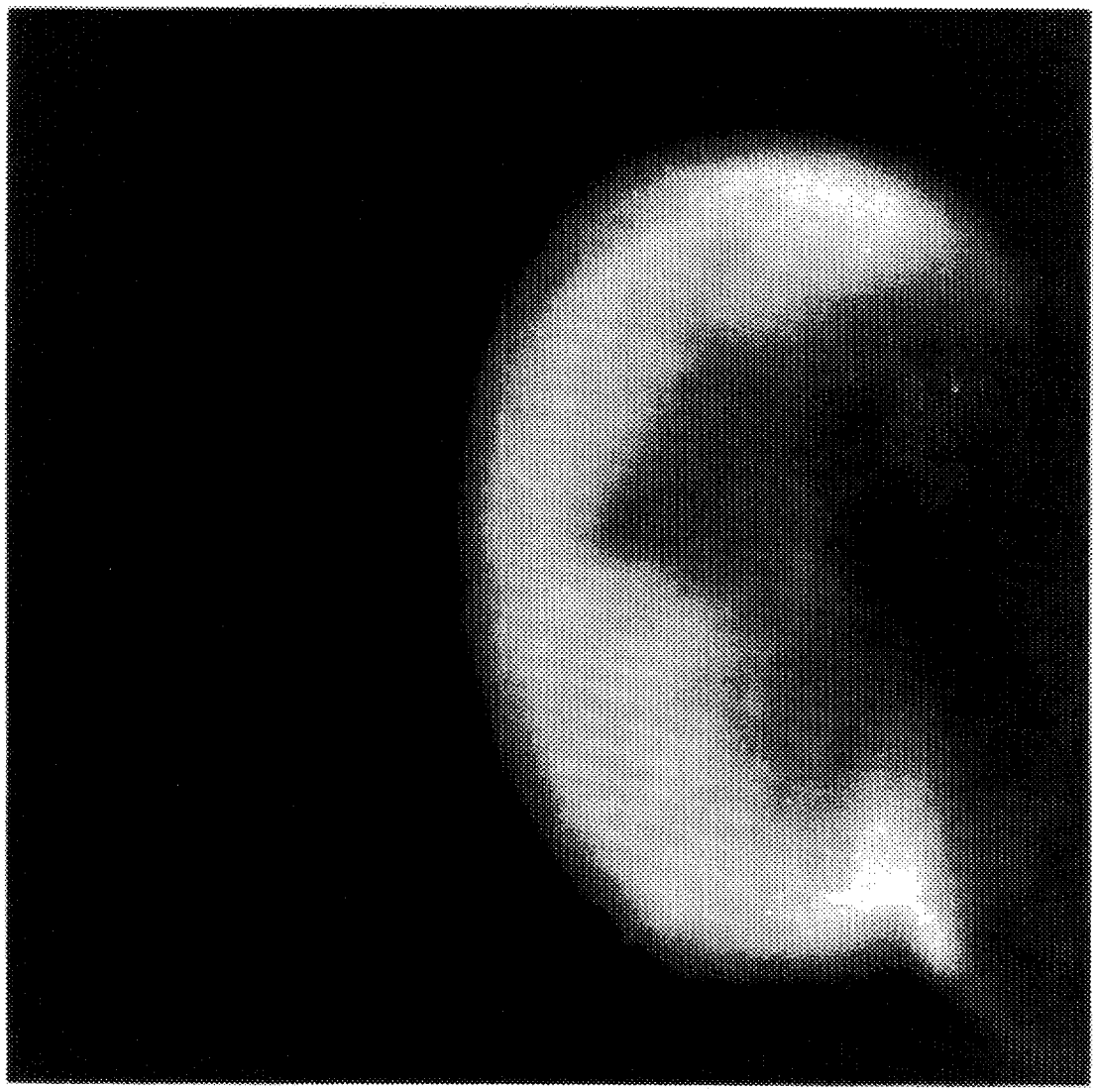
Figure 15C:
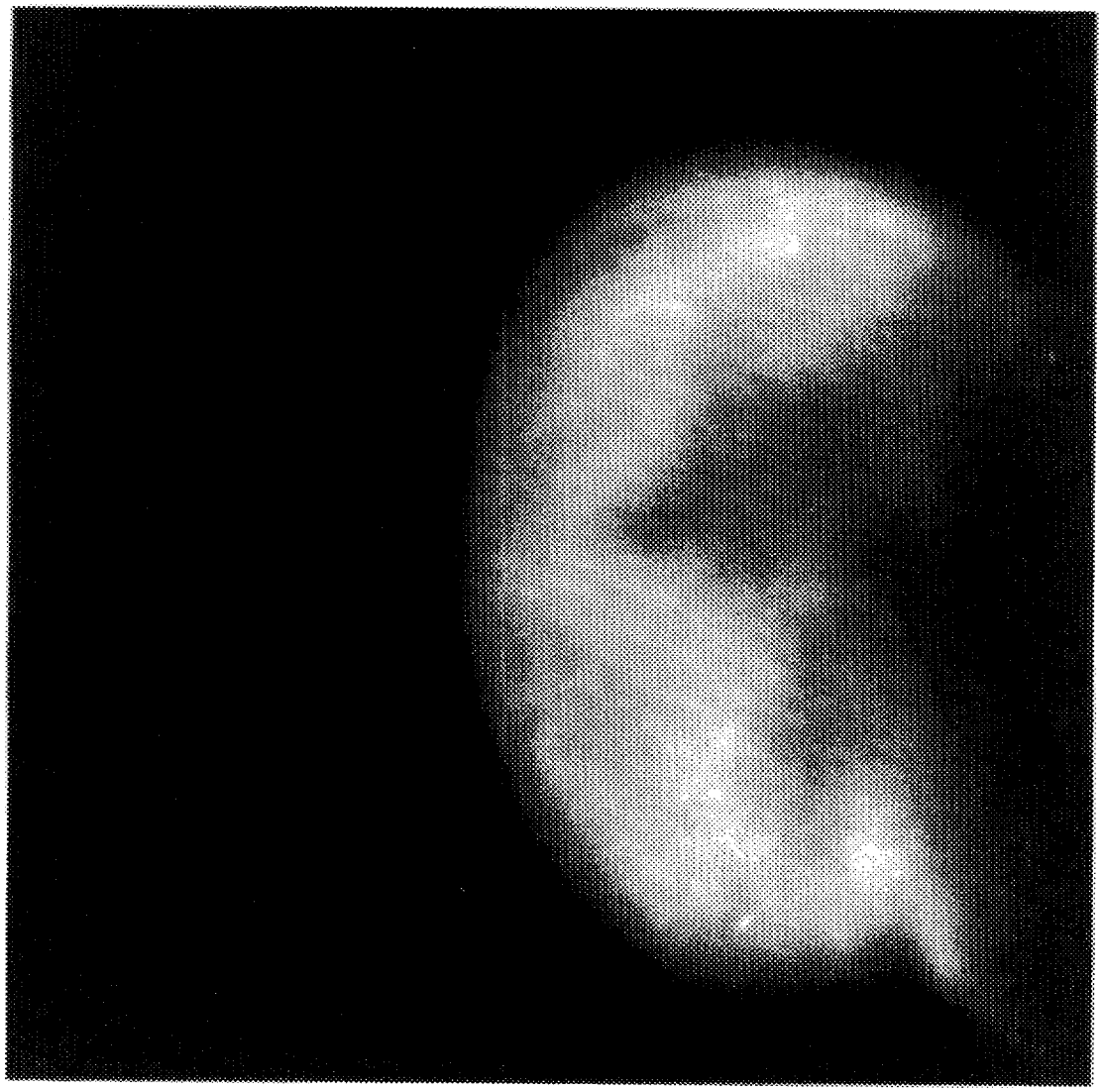
Figure 15D:
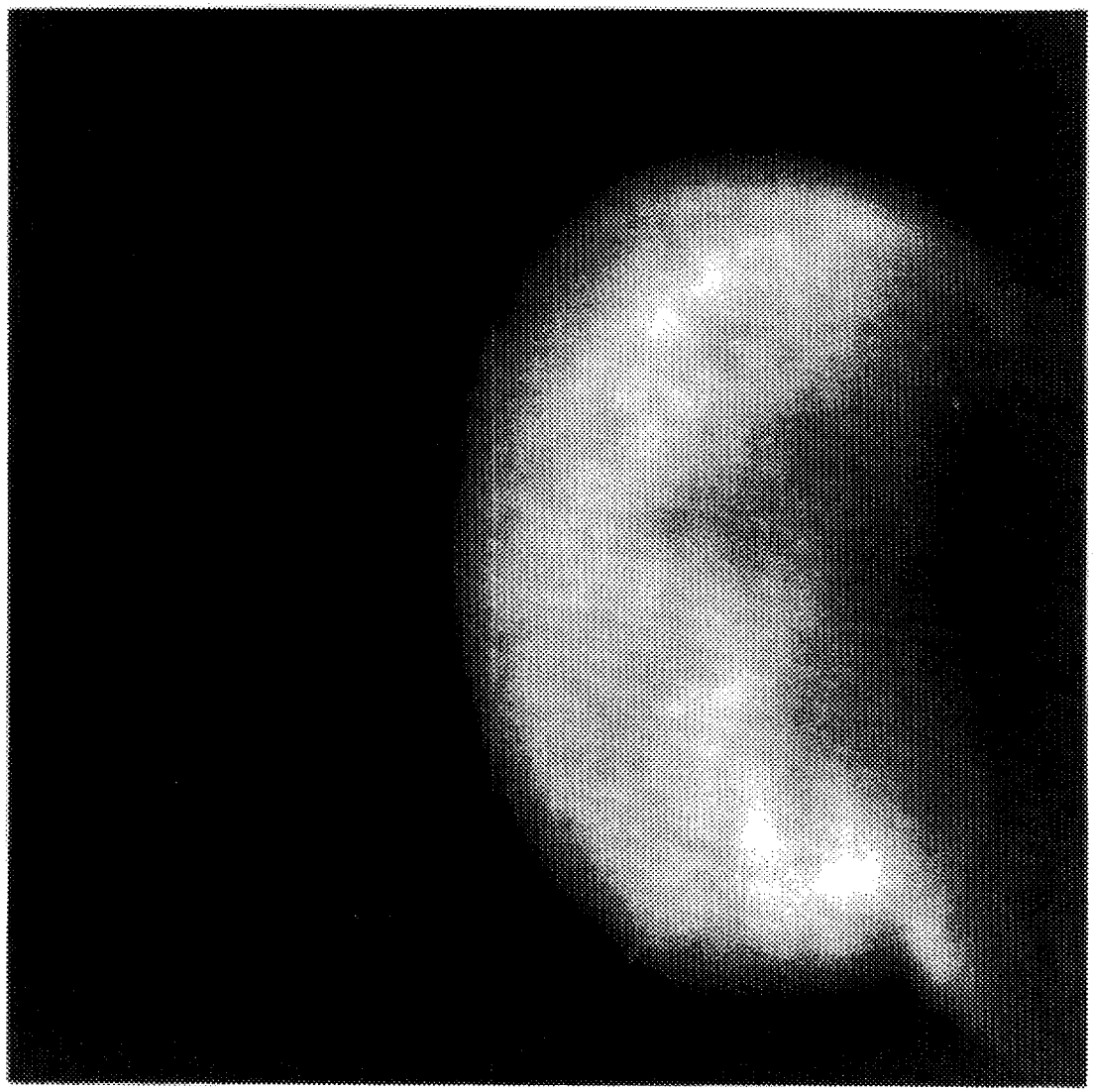
Figure 16A:
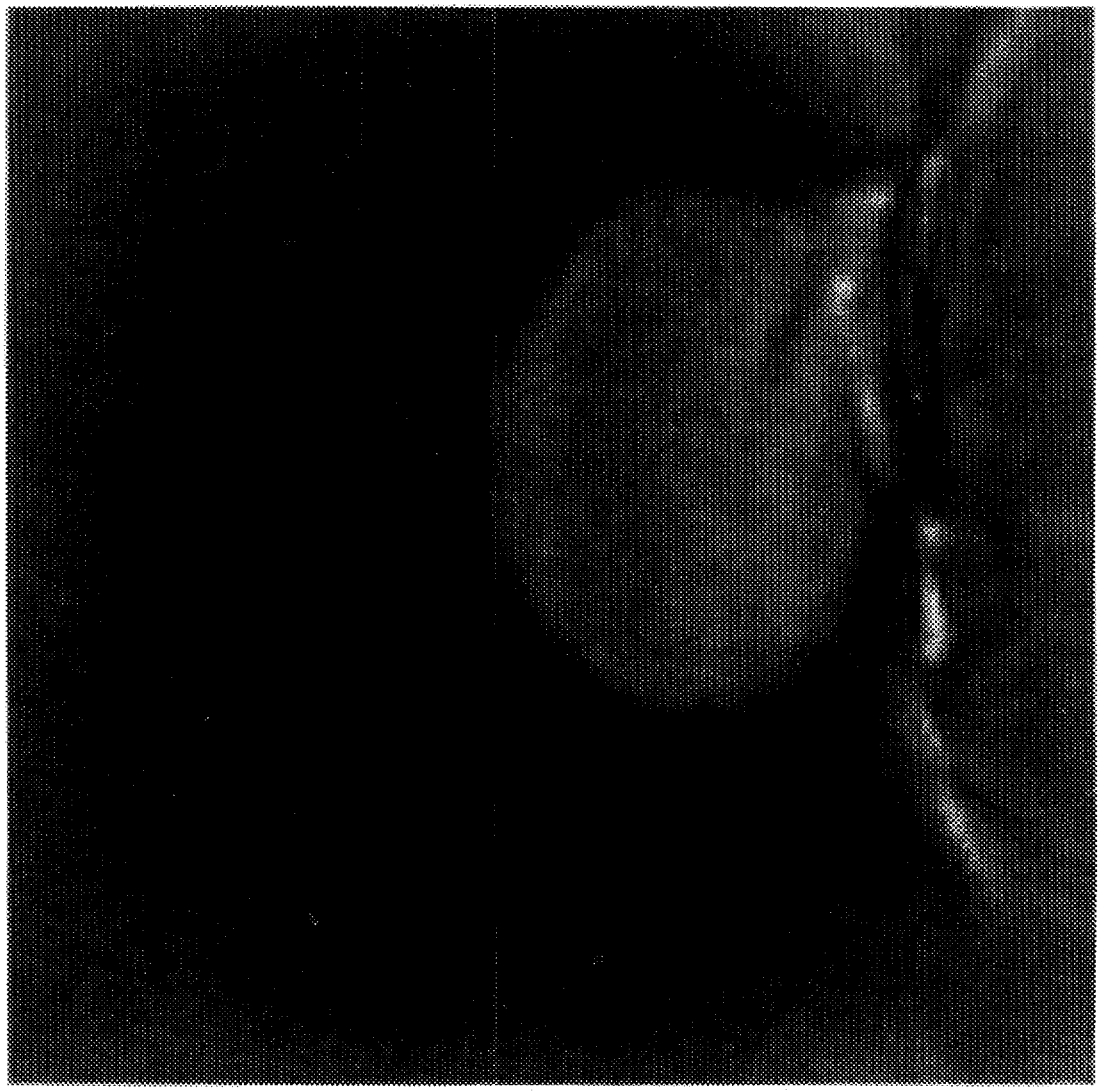
FIGS. 16A–D show MRI 4.7 Tesla, T1-weighted images of Copenhagen rats with the AT-1 prostate tumor model (as in FIGS. 13A–D), but rats are injected i.v. with Ferrioxamine Selective Contrast Agent, wherein the Active is non-covalently bound to a non-anticoagulant GAG, Heparan Sulfate, the Agent lyophilized and reconstituted with water just prior to administration at a concentration of 0.332 mmol/mL Fe(III) and administered at the usual dose of 0.155 mmol of Fe(III) per Kg.
Figure 16B:
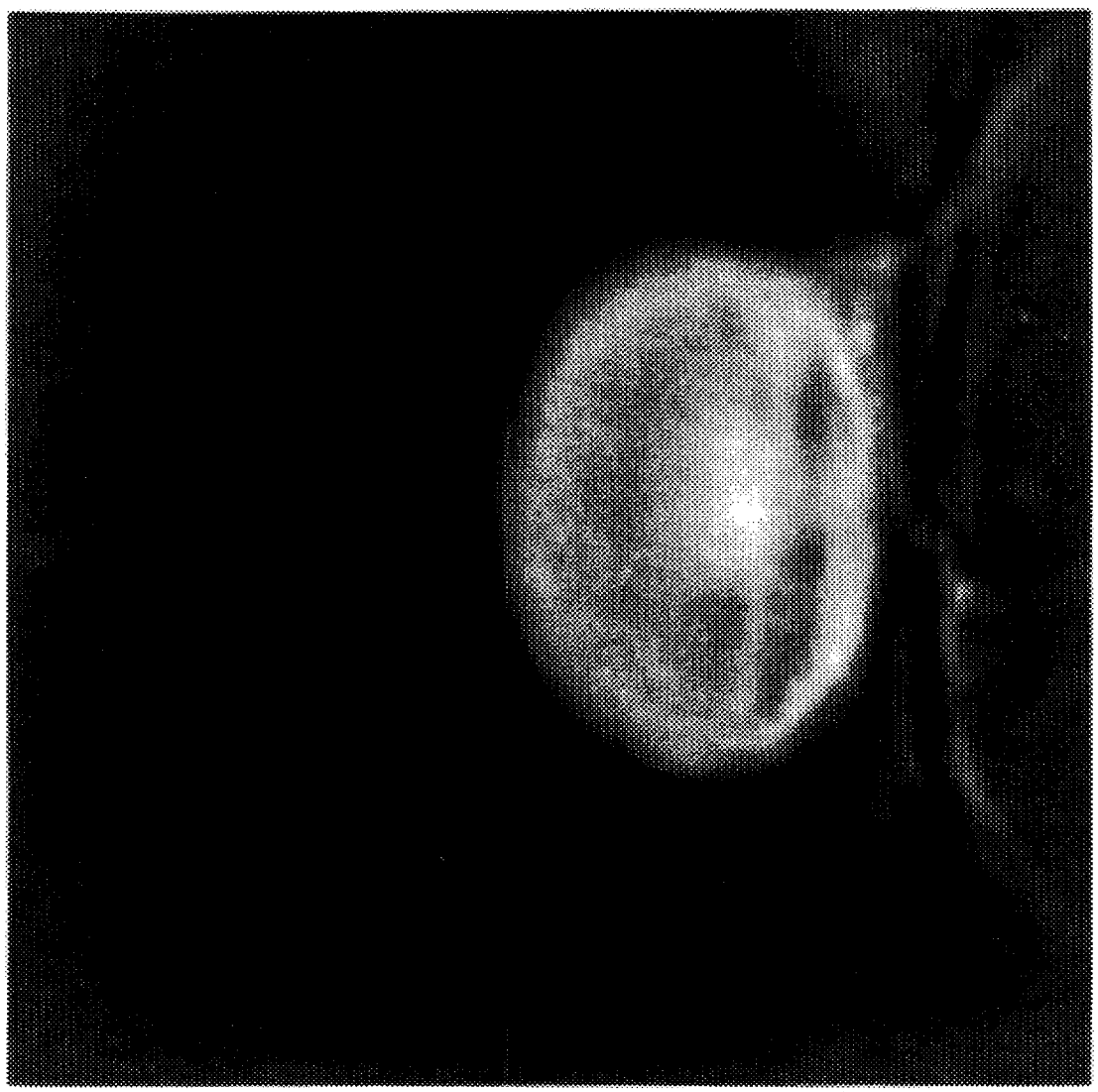
Figure 16C:
Figure 16D:
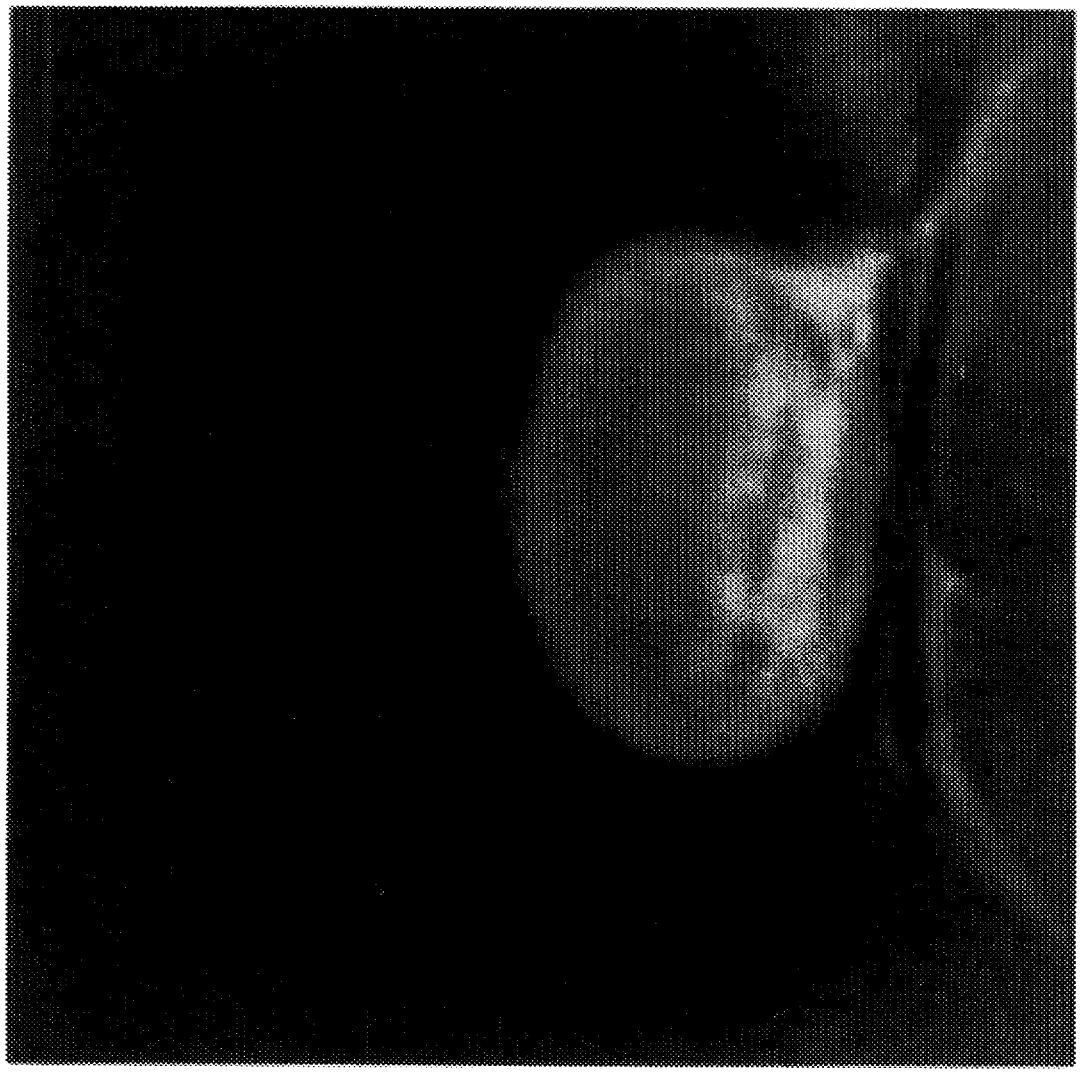

Ferrioxamine:Dermatan Sulfate Selective Contrast Agent: MRI Imaging of Lactating Breast Adenocarcinomas in Syngeneic Fisher 344 Female Rats As shown in FIGS. 2A–4d, T1-weighted MRI images (TR/TE-800/45 and 550/23) are performed at 1.0 and 1.5 Tesla, before (Pre) and after (Post) intravenous (i.v.) injection of Ferrioxamine:Dermatan Sulfate Selective Paramagnetic Contrast Agent (Example 5), at a Ferrioxamine dose of 0.155 mmol/Kg into Fisher 344 female rats, with syngeneic breast adenocarcinomas inoculated by trocar into the livers, such that tumor diameters at the time of imaging are between 1.0 cm and 2.5 cm. Tumors are not conspicuous on standard T1-weighted Precontrast images. Following injection of Ferrioxamine:Dermatan Sulfate Agent, the tumors (a) become rapidly and markedly enhanced at an early postinjection time (7 mins) (FIGS. 2A–B); (b) display very sharp tumor boundaries against surrounding liver (FIGS. 2A–B and 4A–D), and discretely demarcated, darker central region of tumor necrosis (FIGS. 2A–B) (allowing tumor perfusion and function to be spatially resolved and assessed within different, very small anatomical subregions); (c) exhibit sustained contrast for longer than 64 minutes postinjection (MPI) (FIGS. 4A–D, MRI images; FIG. 5, quantitative region-of-interest, ROI, analysis) with continued very well defined tumor borders at prolonged imaging intervals. MRI images and microwave augmented iron stains of the freshly excised, 7 MPI tumors, indicate that tumor-site localization of the Ferrioxamine active occurs only when it is bound (non-covalently) to carrier (FIGS. 2A–B and 4A–D) and not when administered in free form (Active alone) (FIGS. 3A–B). As shown in FIGS. 8A–C, lung metastases of the liver tumor are rapidly and sensitively enhanced in very small 2-mm to 3-mm nodules at an early post-contrast interval; and this enhancement of the tumor at lung sites is also sustained for a prolonged period with high sensitivity plus retention of very sharp tumor boundaries against normal lung. The sustained intervals shown in FIGS. 8A–C are much longer than those typically reported for Gd:DTPA dimeglumine contrast enhancement at body organ sites.

EXAMPLE 19

Ferrioxamine:Dermatan Sulfate Selective Contrast Agent: MRI Imaging of Prostate AT-1 Carcinomas in Syngeneic Copenhagen Rats and Comparison with Gd(III)DTPA As shown in FIGS. 9A–E and 10A–E, T1-weighted MRI images (TR/TE-250/80) performed at 4.7 Tesla, before (Pre)

and after (Post) intravenous (i.v.) injection of Ferrioxamine-:Dermatan Sulfate Selective Paramagnetic Contrast Agent prepared as in Examples 2 and 5, and injected i.v. at an Iron(III) dose of 0.155 mmol/Kg (FIGS. 9A–E); compared to Gadolinium DTPA dimeglumine, injected i.v. at a Gd(III) dose of 0.100 mmol/Kg (FIGS. 10A–E); each of these agents being administered to Copenhagen rats with syngeneic AT-1 prostate adenocarcinomas inoculated into previously prepared skin pouches [Hahn, et al. ], such that tumor diameters at the time of imaging are between 1.0 cm and 2.5 cm. Ferrioxamine:Dermatan Sulfate produces a rapid large enhancement of the Outer Rim of tumor and also of the Vascular Array which fans out from the tumor pedicle which carries a high majority of the tumor vasculature. Sustained contrast and delineation of these elements remains present through kinetic time points of 40 minutes. By comparison, following Gd:DTPA dimeglumine, the outer rim is not well delineated, even at the earliest post-contrast interval (7 MPI). Marked early contrast fading occurs overall in the tumor at 20 MPI, and some agent sequesters in the central, poorly perfused (cystic) regions of tumor (as is typically reported for Gd:DTPA when used for imaging at body sites). At 40 MPI, enhancement reverts to essentially background levels, and at 60 MPI, there is no residual contrast, except for central cystic regions.

EXAMPLE 20

MRI Contrast Enhancement of Acute Dog Myocardial Infarcts by Ferrioxamine:Dermatan Sulfate As shown in FIGS. 11A–D, T1-weighted MRI ECG-gated cardiovascular images are performed at 0.5 Tesla, before (Pre) and after (Post) rapid intravenous (i.v.) infusion of Ferrioxamine:Dermatan Sulfate Selective Paramagnetic Contrast Agent injected i.v. at an Iron(III) dose of 0.155 mmol/Kg into German Shepherd dogs with acute, 90-min myocardial infarcts (ligature of proximal left anterior descending coronary artery) followed by reperfusion for ca. 90 minutes prior to contrast agent infusion. At 7 MPI, Ferrioxamine:Dermatan gives strong enhancement of the infarct zone, and in particular distinguishes the outer boundary of the infarct, which represents the putative marginal zone of the infarct amenable to potential recovery, from the central darker region, which represents the putative irreversible central infarct. Sustained strong enhancement and zonal demarcation is present through 40 MPI. Ferrioxamine injected without carrier at 0.155 mmol/Kg, gives no detectible enhancement. In these studies, infarct sizes and positions are documented by double dye infusion performed immediately after MRI imaging.

EXAMPLE 21

Comparison of MRI Tumor-imaging Potency In Vivo with Ferrioxamine Active Bound to Various Sulfated Glycosaminoglycans Based on low anticoagulant activity, safety and projected site-localization potential, certain alternative glycosaminoglycan carriers and certain alternative physical forms of the resulting Selective MRI Contrast Agents are compared for their relative in vivo potencies of carrier-mediated tumor localization of bound Ferrioxamine. Because of its high spatial resolution and capacity to detect subtle quantitative differences in agent localization, the AT-1 prostate tumor model of Example 19 is used.

TABLE 2

| FIG. NO. | Agent | Form (Liquid/ Lyo) | Concentration (metal, mmol/mL) | Relative Potency (scale of 1–6) |
|---|---|---|---|---|
| 12A–D | Ferrioxamine Dermatan-$SO_3^-$ | Lyo | 0.415 | 3.5 |
| 13A–D | Gd:DTPA-Lys Dermatan-$SO_3^-$ | Liquid | 0.415 | 6 |
| 14A–D | Ferrioxamine Oversulfated Dermatan-$SO_3^-$ | Lyo | 0.332 | 4.5 |
| 15A–D | Ferrioxamine Oversulfated Chondroitin-$SO_3^-$ | Lyo | 0.332 | 5 |
| 16A–D | Ferrioxamine Heparan Sulfate | Lyo | 0.332 | 3.5 |

Carriers of shorter chain length than the glycosaminoglycans, namely pentosan polysulfate, are found to be less potent (typically only 2/6 on the scale above) and remain at the tumor site for intervals of less than about 20 minutes, whereas the GAGs shown in the table above, are much more potent and have considerably longer tumor site localization intervals. In comparing these carriers, there is a slight-to-moderate trend towards increased carrier potency based on carrier sulfate charge density.

Lyo=Lyophilized powder form $SO_3^-$=Sulfate (e.g. $SO_3^-$=dermatan sulfate)

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following references are incorporated in pertinent part by reference herein for the reasons cited above.

REFERENCES

Axen (1974) *Prostaglandins*, 5(1):45.
Bacchi et al. (1993) *Am. J. Pathol.*, 142:579.
Bartling et al. (1974) *Biotechnology and Bioengineering*, 16:1425.
Bevilacqua et al. (1993) *J. Clin. Invest.*, 91:91.
Bevilaqua et al. (Jul. 10, 1993) *Congress of Intl. Soc. of Thrombosis and Hemostasis*.
Boneu et al. (1992) *Heparin and Related Polysaccharides*, Plenum Press, NY, pg. 237.
Brechbiel et al. (1986), *Inorg. Chem.*, Vol 25, p. 2772–2781.
Crumbliss et al. (1991), HANDBOOK OF MICROBIAL IRON CHELATES, Chapter 7, CRC Press.
Danishefsky et al. (1972) *Thrombosis Research*, 1:173.
Danishefsky et al. (1971) *Carbohydrate Research*, 16:199.
Elices et al. (1990) *Cell*, 60:577–584.
Geraldes et al. (1985) *Proc. Soc. Mag. Res. Med.*, Vol. 2, p. 860.
Hahn et al. (1993) *Mag. Res. Imaging*, 11:1007.
Hashimoto et al. (1983) *J. Nucl. Med.* Vol. 24, p. 123.
Huber et al. (1991) *Science*, 254:99–102.
Janoki et al. 1983) *Int. J. Appl. Radiat. Isot.*, 34(6):871.

Kjellen et al. (1977) *Biochem. and Biophys. Res. Comm.,* 74:126–133.
Levine (1993) *FASEB Journal,* 7:1242.
Li et al. (1993) *Bioconjugate Chem.* Vol. 4, p. 275–283.
Lin et al. (1975) *Analytical Biochemistry,* 63:485.
Lindahl and Hook (1978) *Ann. Rev. Biochem.,* 47:385.
Lorant et al. (1993) *J. Clin. Invest.,* 92:559.
Lyle et al. (1963) *Talanta,* 10:1177.
Montrucchio et al. (1993) *Am. J. Pathol.,* 142:471.
Munro et al. (1992) *Am. J. Pathol.,* 141:1397.
Nikkari et al. (1993) *Am. J. Pathol.,* 143:1019.
Ramirez et al. (1973) *J. Macromol. Sci-Chem.,* A7(5):1035.
Ranney (1990) U.S. Pat. No. 4,925,678.
Ranney (1992) U.S. Pat. No. 5,108,759.
Ranney, patent application Ser. No. 07/642,033.
Ranney, patent application Ser. No. 07/803,595.
Ranney, patent application Ser. No. 07/880,660.
Ransohoff et al. (1993) *FASEB Journal,* 7:592.
Rice et al. (1991) *Am. J. Pathol.,* 138:385.
Sasseville et al. (1992) *Am. J. Pathol.,* 141:1021.
Sessler et al., U.S. Pat. No. 5,159,065.
Sessler et al., U.S. Pat. No. 5,252,720.
Sessler et al., U.S. Pat. No. 4,935,498.
Sharon et al. (January 1993) *Scientific American,* pg. 83.
Steinhoff et al. (1993) *Am. J. Pathol.* 142:481.
Strieter et al. (1992) *Am. J. Pathol.,* 141:1279.
Travis (1993) *Science,* 260:906.

What is claimed is:

1. An agent comprising at least about 15 weight percent chelator for paramagnetic metal ions, and a sulfated oligosaccharide, sulfated polysaccharide or glycosaminoglycan carrier, said chelator having a cationic group and being bound to said carrier by non-covalent binding.

2. The agent of claim 1 wherein said chelator has a net positive ionic charge at physiological pH.

3. The agent of claim 1 further comprising a chelated paramagnetic metal ion.

4. The agent of claim 2 further comprising a chelated paramagnetic metal ion.

5. The agent of claim 1 further comprising a chelated metal ion selected from the group consisting of iron, manganese, chromium, copper, nickel, gadolinium, erbium, europium, dysprosium and holmium.

6. The agent of claim 1 wherein said carrier is a sulfated glycosaminoglycan or sulfatoid.

7. The agent of claim 1, wherein the carrier is heparin, desulfated heparin, glycine-conjugated heparin, heparan sulfate, dermatan sulfate, chondroitin sulfate, pentosan polysulfate or dextran sulfate.

8. The agent of claim 1, wherein said chelator has a formation constant for paramagnetic metal ions of at least about $10^{14}$.

9. The agent of claim 1, wherein said chelator is a chelator of iron ions.

10. The agent of claim 1, wherein said chelator is a hydroxamate.

11. The agent of claim 3, wherein said chelator together with said metal ion is ferrichrome, ferrioxamine, enterobactin, ferrimycobactin or ferrichrysin.

12. The agent of claim 1, wherein said chelator is deferoxamine.

13. The agent of claim 1, wherein said chelator is deferoxamine, said carrier is heparin, or a heparin fragment and the agent further comprises iron(III).

14. The agent of claim 1, wherein said chelator is deferoxamine and said carrier is dermatan sulfate or a dermatan sulfate fragment.

15. The agent of claim 14, wherein said agent further comprises chelated iron(III).

16. An agent for magnetic resonance imaging comprising deferoxamine non-covalently bound to a carrier selected from the group consisting of heparin, heparan sulfate, dermatan sulfate and chondroitin sulfate.

17. The agent of claim 16, further comprising a paramagnetic metal ion.

18. The agent of claim 1, wherein said chelator is a porphine, porphyrin, sapphyrin or texaphyrin.

19. The agent of claim 18 further defined as comprising a paramagnetic metal ion.

20. The agent of claim 18, further defined as comprising an iron ion or a gadolinium ion.

21. The agent of claim 1, wherein said chelator is 5,10,15,20-Tetrakis(1-methyl-4-pyridyl)-21H,23-porphine, said carrier is heparin and the agent further comprises a chelated iron ion.

22. The agent of claim 1, wherein said chelator is a polyaminocarboxylate or macrocyclic.

23. The agent of claim 22, further defined as comprising a paramagnetic metal ion.

24. The agent of claim 22, wherein said chelator is an amine derivative of diethylenetriaminetetraacetate or is a derivative of diethylenetriaminetetraacetate having a net positive charge at physiological pH.

25. The agent of claim 22, wherein said chelator is an amine derivative of 1,4,7,10-tetraazacyclododecane-N,N',N",N"'-tetraacetate (DOTA) or is a derivative of 1,4,7,10-tetraazacyclododecane-N,N',N",N"'-tetraacetate having a net positive charge at physiological pH.

26. The agent of claim 1, wherein said carrier is defined further as being complementary to endothelial determinants selectively induced at disease sites.

27. An agent for in vivo magnetic resonance imaging, the agent comprising a chelator having a net positive charge at physiological pH, a chelated metal ion and a sulfated hydrophilic carrier, said chelator/metal ion chelate being bound by non-covalent binding at a weight percentage of at least about 15% to said carrier, and said carrier being selected from the group consisting of heparin, desulfated heparin, glycine-conjugated heparin, heparan sulfate, dermatan sulfate, chondroitin sulfate, pentosan polysulfate and dextran sulfate.

28. An agent for enhancing body imaging, the agent comprising diethylenetriaminepentaacetate-lysine, chelated Gd(III) and a glycosaminoglycan carrier non-covalently bound to said diethylenetriaminepentaacetate-lysine.

29. An agent for enhancing body imaging, the agent comprising DOTA-lysine, chelated Gd(III) and a glycosaminoglycan carrier non-covalently bound to said 1,4,7,10-tetraazacyclododecane-N,N',N",N"'-tetraacetate-lysine (DOTA-lysine).

30. An agent for magnetic resonance imaging comprising ferrioxamine bound by non-covalent binding to dermatan sulfate.

31. The agent of claims 1, 16, 27, 28 or 29 defined further as being in a combination with at least one of a buffer, saccharide, sulfated saccharide, or salt, to produce an osmotic strength suitable for parenteral administration, and as being an aqueous solution or a lyophilized or dry preparation suitable for aqueous reconstitution having the desired osmotic strength, and wherein said agent is aseptic or sterile.

32. A method of enhancing magnetic resonance images or spectra in vertebrate animals comprising administering to said animal an effective amount of the agent of claim 4.

33. A method of enhancing in vivo images arising from induced magnetic resonance signals, comprising the steps of:

(a) administering to a subject an effective amount of the agent of claim 1;
(b) exposing the subject to a magnetic field and radiofrequency pulse; and
(c) acquiring an induced magnetic resonance signal to obtain a contrast effect.

* * * * *

UNITED STATES PATENT AND TRADEMARK OFFICE
CERTIFICATE OF CORRECTION

PATENT NO. : 5,672,334

DATED : September 30, 1997

INVENTOR(S) : David F. Ranney

It is certified that error appears in the above-identified patent and that said Letters Patent is hereby corrected as shown below:

In the title page, item [63], line 2, delete "Dec. 9, 1991, Pat. No. 5,214,661" and insert -- Apr. 3, 1992, abandoned --

Column 20, line 11, delete "U.S. Pat. No. 5,214,661" and inserting -- abandoned --.

Signed and Sealed this

Third Day of March, 1998

*Attest:*

BRUCE LEHMAN

*Attesting Officer*    *Commissioner of Patents and Trademarks*